United States Patent
von Eynatten et al.

(10) Patent No.: US 12,263,153 B2
(45) Date of Patent: *Apr. 1, 2025

(54) PHARMACEUTICAL COMPOSITION, METHODS FOR TREATING AND USES THEREOF

(71) Applicant: Boehringer Ingelheim International GmbH, Ingelheim am Rhein (DE)

(72) Inventors: Maximilian von Eynatten, Wiesbaden (DE); Uli Christian Broedl, Oakville (CA); Hans-Juergen Woerle, Grandvaux VD (CH)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 220 days.

This patent is subject to a terminal disclaimer.

(21) Appl. No.: 17/831,460

(22) Filed: Jun. 3, 2022

(65) Prior Publication Data

US 2022/0288012 A1 Sep. 15, 2022

Related U.S. Application Data

(63) Continuation of application No. 17/094,045, filed on Nov. 10, 2020, now abandoned, which is a continuation of application No. 16/738,116, filed on Jan. 9, 2020, now abandoned, which is a continuation of application No. 15/806,389, filed on Nov. 8, 2017, now abandoned.

(60) Provisional application No. 62/514,249, filed on Jun. 2, 2017, provisional application No. 62/420,062, filed on Nov. 10, 2016.

(51) Int. Cl.
  *A61K 31/7048* (2006.01)
  *A61K 9/20* (2006.01)
  *A61K 31/351* (2006.01)
  *A61K 45/06* (2006.01)
  *A61P 13/12* (2006.01)

(52) U.S. Cl.
  CPC .......... *A61K 31/351* (2013.01); *A61K 9/2018* (2013.01); *A61K 31/7048* (2013.01); *A61K 45/06* (2013.01); *A61P 13/12* (2018.01)

(58) Field of Classification Search
  None
  See application file for complete search history.

(56) References Cited

U.S. PATENT DOCUMENTS

| | | |
|---|---|---|
| 3,174,901 A | 3/1965 | Sterne |
| 3,884,906 A | 5/1975 | Van Der Meer et al. |
| 4,379,785 A | 4/1983 | Weyer et al. |
| 4,602,023 A | 7/1986 | Kiely et al. |
| 4,639,436 A | 1/1987 | Junge et al. |
| 4,786,023 A | 11/1988 | Harris et al. |
| 4,786,755 A | 11/1988 | Kiely et al. |
| 5,145,684 A | 9/1992 | Liversidge et al. |
| 5,516,530 A | 5/1996 | Lo et al. |
| 5,807,580 A | 9/1998 | Luber |
| 5,880,289 A | 3/1999 | Kaneko et al. |
| 6,414,126 B1 | 7/2002 | Ellsworth et al. |
| 6,498,193 B2 | 12/2002 | Beisswenger et al. |
| 6,515,117 B2 | 2/2003 | Ellsworth et al. |
| 6,613,806 B1 | 9/2003 | Corporation |
| 6,627,611 B2 | 9/2003 | Tomiyama et al. |
| 6,774,112 B2 | 8/2004 | Gougoutas |
| 6,794,480 B2 | 9/2004 | Goto et al. |
| 6,936,590 B2 | 8/2005 | Washburn et al. |
| 6,972,283 B2 | 12/2005 | Fujikura et al. |
| 6,995,183 B2 | 2/2006 | Hamann et al. |
| 7,101,856 B2 | 9/2006 | Glombik et al. |
| 7,169,761 B2 | 1/2007 | Tomiyama et al. |
| 7,202,350 B2 | 4/2007 | Imamura et al. |
| 7,294,618 B2 | 11/2007 | Fushimi et al. |
| 7,371,732 B2 | 5/2008 | Eickelmann et al. |
| 7,375,087 B2 | 5/2008 | Teranishi et al. |
| 7,375,090 B2 | 5/2008 | Himmelsbach et al. |
| 7,375,213 B2 | 5/2008 | Deshpande et al. |
| 7,393,836 B2 | 7/2008 | Eckhardt et al. |
| 7,407,955 B2 | 8/2008 | Himmelsbach et al. |
| 7,417,032 B2 | 8/2008 | Eckhardt et al. |
| 7,419,959 B2 | 9/2008 | Eckhardt et al. |
| 7,541,341 B2 | 6/2009 | Fushimi et al. |
| 7,579,449 B2 | 8/2009 | Eckhardt et al. |
| 7,589,193 B2 | 9/2009 | Washburn et al. |
| 7,662,790 B2 | 2/2010 | Himmelsbach et al. |
| 7,674,486 B2 | 3/2010 | Bhaskaran et al. |
| 7,683,160 B2 | 3/2010 | Eckhardt et al. |
| 7,687,469 B2 | 3/2010 | Eckhardt et al. |

(Continued)

FOREIGN PATENT DOCUMENTS

| | | |
|---|---|---|
| CA | 2382480 A1 | 3/2001 |
| CA | 2388818 A1 | 4/2001 |

(Continued)

OTHER PUBLICATIONS

Valentine, Virginia "The Role of the Kidney and Sodium-Glucose Cotransporter-2 Inhibition in Diabetes Management" (2012) Clinical Diabetes, vol. 30, No. 4, 151-155.
Valk, Harold W. de "DPP-4 Inhibitors and Combined Treatment in Type 2 Diabetes: Re-evaluation of Clinical Success and Safety" (2007) The Review of Diabetic Studies, vol. 4, No. 3, 126-133.
Vallon, Volker et al. "Glomerular Hyperfiltration in Experimental Diabetes Melliutes: Potential Role of Tubular Reabsorption" (1999) J. Am. Soc. Nephrol., V 10: pp. 2569-2576.
Vallon, Volker et al. "Knockout of Na-glucose transporter SGLT2 attenuates hyperglycemia and glomerular hyperfiltration but not kidney growth or injury in diabetes mellitus" (2012) Am J Physiol Renal Physiol, vol. 304, F156-F167.
Vallon, Volker et al. "SGLT2 inhibitor empagliflozin reduces renal growth and albuminuria in proportion to hyperglycemia and prevents glomerular hyperfiltration in diabetic Akita mice" (2013) Am J Physiol Renal Physiol, 306, F194-F204.

(Continued)

*Primary Examiner* — Traviss C McIntosh, III
(74) *Attorney, Agent, or Firm* — David L. Kershner

(57) ABSTRACT

The present invention relates to methods for treating or preventing chronic kidney disease and cardiovascular disease in patients with chronic kidney disease comprising administering empagliflozin to the patient.

30 Claims, No Drawings

(56) References Cited

U.S. PATENT DOCUMENTS

| | | | |
|---|---|---|---|
| 7,713,938 B2 | 5/2010 | Himmelsbach et al. | |
| 7,723,309 B2 | 5/2010 | Himmelsbach et al. | |
| 7,723,379 B2 | 5/2010 | Romanczyk, Jr. et al. | |
| 7,745,414 B2 | 6/2010 | Eckhardt et al. | |
| 7,772,191 B2 | 8/2010 | Eckhardt et al. | |
| 7,772,192 B2 | 8/2010 | Esko | |
| 7,772,378 B2 | 8/2010 | Himmelsbach et al. | |
| 7,772,407 B2 | 8/2010 | Imamura et al. | |
| 7,776,830 B2 | 8/2010 | Eckhardt et al. | |
| 7,847,074 B2 | 12/2010 | Eckhardt et al. | |
| 7,851,502 B2 | 12/2010 | Bindra et al. | |
| 7,851,602 B2 | 12/2010 | Himmelsbach et al. | |
| 7,858,587 B2 | 12/2010 | Eckhardt et al. | |
| 7,879,806 B2 | 2/2011 | Himmelsbach et al. | |
| 7,879,807 B2 | 2/2011 | Himmelsbach et al. | |
| 8,039,441 B2 | 10/2011 | Himmelsbach et al. | |
| 8,119,648 B2 | 2/2012 | Himmelsbach et al. | |
| 8,178,541 B2 | 5/2012 | Himmelsbach et al. | |
| 8,232,281 B2 | 7/2012 | Dugi et al. | |
| 8,283,326 B2 | 10/2012 | Eckhardt et al. | |
| 8,507,450 B2 | 8/2013 | Eckhardt et al. | |
| 8,551,957 B2 | 10/2013 | Dugi et al. | |
| 8,557,782 B2 | 10/2013 | Eckhardt et al. | |
| 8,802,842 B2 | 8/2014 | Weber et al. | |
| 9,024,010 B2 | 5/2015 | Weber et al. | |
| 9,034,883 B2 | 5/2015 | Klein et al. | |
| 9,127,034 B2 | 9/2015 | Eckhardt et al. | |
| 9,155,705 B2 | 10/2015 | Friedl et al. | |
| 9,192,616 B2 | 11/2015 | Johnson | |
| 9,192,617 B2 | 11/2015 | Mayoux et al. | |
| 9,949,997 B2 | 4/2018 | Broedl et al. | |
| 9,949,998 B2 * | 4/2018 | Broedl | A61K 31/7048 |
| 10,258,637 B2 * | 4/2019 | Broedl | A61K 31/7048 |
| 10,406,172 B2 | 9/2019 | Eickelmann et al. | |
| 10,596,120 B2 | 3/2020 | Ito et al. | |
| 10,610,489 B2 | 4/2020 | Schneider et al. | |
| 11,090,323 B2 * | 8/2021 | Broedl | A61K 9/2866 |
| 11,666,590 B2 * | 6/2023 | Broedl | A61P 3/10 |
| | | | 514/23 |
| 11,833,166 B2 * | 12/2023 | Broedl | A61K 9/0018 |
| 2001/0018090 A1 | 8/2001 | Noda et al. | |
| 2001/0041674 A1 | 11/2001 | Tomiyama et al. | |
| 2001/0044435 A1 | 11/2001 | Himmelsbach et al. | |
| 2002/0137903 A1 | 9/2002 | Ellsworth et al. | |
| 2002/0173509 A1 | 11/2002 | Himmelsbach et al. | |
| 2002/0198205 A1 | 12/2002 | Himmelsbach et al. | |
| 2003/0064935 A1 | 4/2003 | Gougoutas | |
| 2003/0087843 A1 | 5/2003 | Washburn | |
| 2003/0114390 A1 | 6/2003 | Washburn et al. | |
| 2003/0212070 A1 | 11/2003 | Schwink et al. | |
| 2004/0097510 A1 | 5/2004 | Himmelsbach et al. | |
| 2004/0138148 A1 | 7/2004 | Fushimi et al. | |
| 2004/0138439 A1 | 7/2004 | Deshpande et al. | |
| 2004/0247677 A1 | 12/2004 | Oury et al. | |
| 2004/0259819 A1 | 12/2004 | Frick et al. | |
| 2005/0065098 A1 | 3/2005 | Fujikura et al. | |
| 2005/0085680 A1 | 4/2005 | Auerbach et al. | |
| 2005/0124555 A1 | 6/2005 | Tomiyama et al. | |
| 2005/0187168 A1 | 8/2005 | Eickelmann et al. | |
| 2005/0209166 A1 | 9/2005 | Eckhardt et al. | |
| 2005/0209309 A1 | 9/2005 | Sato et al. | |
| 2005/0233982 A1 | 10/2005 | Himmelsbach et al. | |
| 2005/0234108 A1 | 10/2005 | Himmelsbach et al. | |
| 2006/0009400 A1 | 1/2006 | Eckhardt et al. | |
| 2006/0019948 A1 | 1/2006 | Eckhardt et al. | |
| 2006/0025349 A1 | 2/2006 | Eckhardt et al. | |
| 2006/0035841 A1 | 2/2006 | Eckhardt et al. | |
| 2006/0063722 A1 | 3/2006 | Washburn et al. | |
| 2006/0074031 A1 | 4/2006 | Eckhardt et al. | |
| 2006/0079541 A1 | 4/2006 | Langkopf et al. | |
| 2006/0142210 A1 | 6/2006 | Eckhardt et al. | |
| 2006/0189548 A1 | 8/2006 | Himmelsbach et al. | |
| 2006/0210627 A1 | 9/2006 | Pfeffer et al. | |
| 2006/0234953 A1 | 10/2006 | Himmelsbach et al. | |
| 2006/0251728 A1 | 11/2006 | Himmelsbach et al. | |
| 2006/0258749 A1 | 11/2006 | Eckhardt et al. | |
| 2006/0287242 A1 | 12/2006 | Ewing et al. | |
| 2007/0004648 A1 | 1/2007 | Himmelsbach et al. | |
| 2007/0027092 A1 | 2/2007 | Himmelsbach et al. | |
| 2007/0042042 A1 | 2/2007 | Jo et al. | |
| 2007/0049537 A1 | 3/2007 | Eckhardt et al. | |
| 2007/0054867 A1 | 3/2007 | Eckhardt et al. | |
| 2007/0073046 A1 | 3/2007 | Eckhardt et al. | |
| 2007/0249544 A1 | 10/2007 | Himmelsbach et al. | |
| 2007/0259821 A1 | 11/2007 | Eckhardt et al. | |
| 2007/0281940 A1 | 12/2007 | Dugi et al. | |
| 2008/0058379 A1 | 3/2008 | Eckhardt et al. | |
| 2008/0107731 A1 | 5/2008 | Kohlrausch et al. | |
| 2008/0234367 A1 | 9/2008 | Washburn et al. | |
| 2008/0287529 A1 | 11/2008 | Deshpande et al. | |
| 2009/0023913 A1 | 1/2009 | Eckhardt et al. | |
| 2009/0137499 A1 | 5/2009 | Honda et al. | |
| 2009/0281078 A1 | 11/2009 | Routledge et al. | |
| 2009/0318547 A1 | 12/2009 | Eckhardt et al. | |
| 2009/0326215 A1 | 12/2009 | Eckhardt et al. | |
| 2010/0069310 A1 | 3/2010 | Himmelsbach et al. | |
| 2010/0074950 A1 | 3/2010 | Sesha | |
| 2010/0081625 A1 | 4/2010 | Wienrich et al. | |
| 2010/0093654 A1 | 4/2010 | Himmelsbach et al. | |
| 2010/0099641 A1 | 4/2010 | Himmelsbach et al. | |
| 2010/0179191 A1 | 7/2010 | Himmelsbach et al. | |
| 2010/0209506 A1 | 8/2010 | Eisenreich | |
| 2010/0240879 A1 | 9/2010 | Eckhardt et al. | |
| 2010/0249392 A1 | 9/2010 | Eckhardt et al. | |
| 2010/0298243 A1 | 11/2010 | Manuchehri et al. | |
| 2010/0317847 A1 | 12/2010 | Eckhardt et al. | |
| 2011/0014284 A1 | 1/2011 | Eisenreich et al. | |
| 2011/0015225 A1 | 1/2011 | Murata et al. | |
| 2011/0046076 A1 | 2/2011 | Eickelmann et al. | |
| 2011/0046087 A1 | 2/2011 | Eickelmann et al. | |
| 2011/0065731 A1 | 3/2011 | Dugi et al. | |
| 2011/0077212 A1 | 3/2011 | Seed et al. | |
| 2011/0098240 A1 | 4/2011 | Dugi et al. | |
| 2011/0178033 A1 | 7/2011 | Eckhardt et al. | |
| 2011/0195917 A1 | 8/2011 | Dugi et al. | |
| 2011/0206766 A1 | 8/2011 | Friedl et al. | |
| 2011/0236477 A1 | 9/2011 | Schneider et al. | |
| 2011/0237526 A1 | 9/2011 | Weber et al. | |
| 2011/0237789 A1 | 9/2011 | Weber et al. | |
| 2012/0041069 A1 | 2/2012 | Sesha | |
| 2012/0071403 A1 | 3/2012 | Strumph et al. | |
| 2012/0094894 A1 | 4/2012 | Graefe-Mody et al. | |
| 2012/0121530 A1 | 5/2012 | Klein et al. | |
| 2012/0196812 A1 | 8/2012 | Eickelmann et al. | |
| 2012/0219622 A1 | 8/2012 | Kohlrausch et al. | |
| 2012/0283169 A1 | 11/2012 | Grempler et al. | |
| 2012/0296080 A1 | 11/2012 | Eckhardt et al. | |
| 2013/0035281 A1 | 2/2013 | Klein et al. | |
| 2013/0035298 A1 | 2/2013 | Broedl et al. | |
| 2013/0064887 A1 | 3/2013 | Ito et al. | |
| 2013/0096076 A1 | 4/2013 | Dugi et al. | |
| 2013/0137646 A1 | 5/2013 | Wienrich et al. | |
| 2013/0236543 A1 | 9/2013 | Ito et al. | |
| 2013/0252908 A1 | 9/2013 | Mayoux et al. | |
| 2014/0031301 A1 | 1/2014 | Eickelmann et al. | |
| 2014/0038911 A1 | 2/2014 | Eickelmann et al. | |
| 2014/0046046 A1 | 2/2014 | Eckhardt et al. | |
| 2014/0087996 A1 | 3/2014 | Klein et al. | |
| 2014/0088027 A1 | 3/2014 | Grempler et al. | |
| 2014/0256624 A1 | 9/2014 | Grempler et al. | |
| 2014/0303097 A1 | 10/2014 | Broedl et al. | |
| 2014/0303098 A1 * | 10/2014 | Broedl | A61K 31/7034 |
| | | | 514/23 |
| 2014/0315832 A1 | 10/2014 | Broedl et al. | |
| 2015/0272977 A1 | 10/2015 | Reiche et al. | |
| 2015/0322053 A1 | 11/2015 | Eckhardt et al. | |
| 2016/0000816 A1 | 1/2016 | Broedl et al. | |
| 2016/0030385 A1 | 2/2016 | Manuchehri et al. | |
| 2016/0038523 A1 | 2/2016 | Broedl et al. | |
| 2016/0038524 A1 | 2/2016 | Broedl et al. | |
| 2016/0038525 A1 | 2/2016 | Broedl et al. | |
| 2016/0074415 A1 | 3/2016 | Wienrich et al. | |
| 2017/0020907 A1 | 1/2017 | Eickelmann et al. | |
| 2017/0095424 A1 | 4/2017 | Ito et al. | |

(56) References Cited

U.S. PATENT DOCUMENTS

| | | |
|---|---|---|
| 2017/0106009 A1 | 4/2017 | Mayoux |
| 2017/0189437 A1 | 7/2017 | Manuchehri et al. |
| 2017/0266152 A1 | 9/2017 | Broedl et al. |
| 2017/0305952 A1 | 10/2017 | Klein et al. |
| 2017/0333465 A1 | 11/2017 | Broedl et al. |
| 2018/0104249 A1 | 4/2018 | Eisenreich |
| 2018/0104268 A1 | 4/2018 | Mayoux et al. |
| 2018/0125813 A1 | 5/2018 | von Eynatten et al. |
| 2018/0169126 A1 | 6/2018 | Broedl et al. |
| 2018/0177794 A1 | 6/2018 | Wienrich et al. |
| 2018/0185291 A1 | 7/2018 | Ito et al. |
| 2018/0193427 A1 | 7/2018 | Grempler et al. |
| 2018/0200278 A1 | 7/2018 | Broedl et al. |
| 2018/0214468 A1 | 8/2018 | Broedl et al. |
| 2018/0289678 A1 | 10/2018 | Eisenreich et al. |
| 2018/0318251 A1 | 11/2018 | Broedl et al. |
| 2018/0344647 A1 | 12/2018 | Boeck et al. |
| 2019/0015437 A1 | 1/2019 | Broedl et al. |
| 2019/0038654 A1 | 2/2019 | Broedl et al. |
| 2019/0134072 A1 | 5/2019 | Broedl et al. |
| 2019/0209596 A1 | 7/2019 | Mayoux |
| 2019/0298749 A1 | 10/2019 | Mayoux et al. |
| 2019/0309004 A1 | 10/2019 | Wirth et al. |
| 2019/0350894 A1 | 11/2019 | Broedl et al. |
| 2019/0350957 A1 | 11/2019 | Broedl et al. |
| 2020/0069713 A1 | 3/2020 | Eickelmann et al. |
| 2020/0085851 A1 | 3/2020 | Eickelmann et al. |
| 2020/0138770 A1 | 5/2020 | von Eynatten et al. |
| 2020/0138844 A1 | 5/2020 | Broedl et al. |
| 2020/0188306 A1 | 6/2020 | Schneider et al. |
| 2020/0222423 A1 | 7/2020 | Wienrich et al. |
| 2020/0268777 A1 | 8/2020 | Broedl et al. |
| 2020/0297639 A1 | 9/2020 | Ito et al. |
| 2020/0360412 A1 | 11/2020 | Broedl et al. |
| 2020/0368261 A1 | 11/2020 | Broedl et al. |
| 2020/0397809 A1 | 12/2020 | Mayoux |
| 2020/0397867 A1 | 12/2020 | Grempler et al. |
| 2021/0059974 A1 | 3/2021 | Broedl et al. |
| 2021/0228533 A1 | 7/2021 | Von Eynatten et al. |
| 2021/0228610 A1 | 7/2021 | Broedl et al. |
| 2021/0299153 A1 | 9/2021 | Broedl et al. |
| 2022/0193045 A1 | 6/2022 | Eisenreich et al. |
| 2022/0211659 A1 | 7/2022 | Broedl et al. |
| 2022/0331326 A1 | 10/2022 | Eisenreich |

FOREIGN PATENT DOCUMENTS

| | | |
|---|---|---|
| CA | 2402609 A1 | 9/2001 |
| CA | 2423568 A1 | 4/2002 |
| CA | 2432428 A1 | 6/2002 |
| CA | 2437240 A1 | 8/2002 |
| CA | 2478889 A1 | 2/2004 |
| CA | 2494177 A1 | 2/2004 |
| CA | 2496249 A1 | 3/2004 |
| CA | 2470365 A1 | 6/2004 |
| CA | 2508024 A1 | 6/2004 |
| CA | 2508226 A1 | 6/2004 |
| CA | 2526145 A1 | 9/2004 |
| CA | 2539032 A1 | 3/2005 |
| CA | 2548353 A1 | 7/2005 |
| CA | 2557269 A1 | 9/2005 |
| CA | 2557320 A1 | 9/2005 |
| CA | 2557801 A1 | 10/2005 |
| CA | 2569915 A1 | 1/2006 |
| CA | 2572149 A1 | 1/2006 |
| CA | 2572819 A1 | 1/2006 |
| CA | 2573777 A1 | 2/2006 |
| CA | 2574451 A1 | 2/2006 |
| CA | 2574500 A1 | 4/2006 |
| CA | 2586938 A1 | 5/2006 |
| CA | 2649922 A1 | 11/2007 |
| CA | 2651019 A1 | 11/2007 |
| CA | 2720450 A1 | 10/2009 |
| CA | 2812519 A1 | 10/2014 |
| CN | 1342151 A | 3/2002 |
| CN | 1418219 A | 5/2003 |
| CN | 1481370 A | 3/2004 |
| CN | 1930141 A | 3/2007 |
| CN | 101503399 A | 8/2009 |
| CN | 101638423 A | 2/2010 |
| DE | 2758025 A1 | 7/1979 |
| DE | 2951135 A1 | 6/1981 |
| EP | 0206567 A2 | 12/1986 |
| EP | 1224195 B | 7/2002 |
| EP | 1344780 A1 | 9/2003 |
| EP | 1364957 A1 | 11/2003 |
| EP | 1385856 A | 2/2004 |
| EP | 1553094 A1 | 7/2005 |
| EP | 1564210 A1 | 8/2005 |
| EP | 1609785 A1 | 12/2005 |
| EP | 1791852 A2 | 6/2007 |
| EP | 1803729 A1 | 7/2007 |
| EP | 1852108 A1 | 11/2007 |
| EP | 2187879 A1 | 5/2010 |
| EP | 2981271 B1 | 11/2018 |
| JP | 55007256 A | 1/1980 |
| JP | 56039056 A | 4/1981 |
| JP | 58164502 | 9/1983 |
| JP | 62030750 A | 2/1987 |
| JP | H1085502 A | 4/1998 |
| JP | 11124392 A | 5/1999 |
| JP | 2001288178 A | 10/2001 |
| JP | 2002338471 A | 11/2002 |
| JP | 2003511458 A | 3/2003 |
| JP | 2004196788 A | 7/2004 |
| JP | 2004359630 | 12/2004 |
| JP | 2005002092 A | 1/2005 |
| JP | 2005060625 A | 3/2005 |
| JP | 2006176443 A | 7/2006 |
| JP | 2008540373 A | 11/2008 |
| WO | 9520578 A1 | 8/1995 |
| WO | 9725992 A1 | 7/1997 |
| WO | 9831697 A1 | 7/1998 |
| WO | 200031050 A1 | 6/2000 |
| WO | 200035457 A1 | 6/2000 |
| WO | 2001016147 A1 | 3/2001 |
| WO | 2001027128 A1 | 4/2001 |
| WO | 2001074834 A1 | 10/2001 |
| WO | 2002064549 | 8/2002 |
| WO | 2002064606 A1 | 8/2002 |
| WO | 2002068420 A1 | 9/2002 |
| WO | 2002083066 A2 | 10/2002 |
| WO | 2003015769 | 2/2003 |
| WO | 2003020737 A1 | 3/2003 |
| WO | 2003031458 A1 | 4/2003 |
| WO | 200347563 A1 | 6/2003 |
| WO | 2003064411 | 8/2003 |
| WO | 2003078404 A1 | 9/2003 |
| WO | 2003099836 A1 | 12/2003 |
| WO | 2003104223 A1 | 12/2003 |
| WO | 2003106420 A1 | 12/2003 |
| WO | 2004006846 A2 | 1/2004 |
| WO | 2004007458 A1 | 1/2004 |
| WO | 2004007517 A1 | 1/2004 |
| WO | 2004013118 A1 | 2/2004 |
| WO | 2004014931 A1 | 2/2004 |
| WO | 2004018468 A2 | 3/2004 |
| WO | 2004046115 A1 | 6/2004 |
| WO | 2004052902 A1 | 6/2004 |
| WO | 2004052903 A1 | 6/2004 |
| WO | 2004063209 A2 | 7/2004 |
| WO | 2004076470 A1 | 9/2004 |
| WO | 2004080990 A1 | 9/2004 |
| WO | 2005011592 A2 | 2/2005 |
| WO | 2005011786 A1 | 2/2005 |
| WO | 2005012318 A2 | 2/2005 |
| WO | 2005012326 A1 | 2/2005 |
| WO | 2005021566 A2 | 3/2005 |
| WO | 2005049022 A2 | 6/2005 |
| WO | 2005063785 A2 | 7/2005 |
| WO | 2005067976 A2 | 7/2005 |
| WO | 2005085237 A1 | 9/2005 |
| WO | 2005085246 A1 | 9/2005 |
| WO | 2005085265 A1 | 9/2005 |

(56) References Cited

FOREIGN PATENT DOCUMENTS

| | | |
|---|---|---|
| WO | 2005092877 A1 | 10/2005 |
| WO | 2005117861 A1 | 12/2005 |
| WO | 2006002912 A1 | 1/2006 |
| WO | 2006006496 A1 | 1/2006 |
| WO | 2006008038 A1 | 1/2006 |
| WO | 2006010557 A1 | 2/2006 |
| WO | 2006011469 A1 | 2/2006 |
| WO | 2006018150 A1 | 2/2006 |
| WO | 2006034489 A2 | 3/2006 |
| WO | 2006037537 A2 | 4/2006 |
| WO | 2006048427 A1 | 5/2006 |
| WO | 2006064033 A2 | 6/2006 |
| WO | 2006078593 A2 | 7/2006 |
| WO | 2006089872 A1 | 8/2006 |
| WO | 2006108842 A1 | 10/2006 |
| WO | 2006117359 A1 | 11/2006 |
| WO | 2006117360 A1 | 11/2006 |
| WO | 2006120208 A1 | 11/2006 |
| WO | 2007000445 A1 | 1/2007 |
| WO | 2007014894 A2 | 2/2007 |
| WO | 2007025943 A2 | 3/2007 |
| WO | 2007028814 A1 | 3/2007 |
| WO | 2007031548 A2 | 3/2007 |
| WO | 2007033350 A1 | 3/2007 |
| WO | 2007039417 A1 | 4/2007 |
| WO | 2007041053 A2 | 4/2007 |
| WO | 2007093610 A1 | 8/2007 |
| WO | 2007128724 A1 | 11/2007 |
| WO | 2007128749 A1 | 11/2007 |
| WO | 2007128761 A2 | 11/2007 |
| WO | 2007136116 A2 | 11/2007 |
| WO | 2007144175 A2 | 12/2007 |
| WO | 2008002905 A2 | 1/2008 |
| WO | 2008020011 A1 | 2/2008 |
| WO | 2008022267 A2 | 2/2008 |
| WO | 2008034859 A1 | 3/2008 |
| WO | 2008049923 A1 | 5/2008 |
| WO | 2008055870 A1 | 5/2008 |
| WO | 2008055940 A2 | 5/2008 |
| WO | 2008062273 A2 | 5/2008 |
| WO | 2008089892 A1 | 7/2008 |
| WO | 2008090210 A1 | 7/2008 |
| WO | 2008101938 A1 | 8/2008 |
| WO | 2008101939 A1 | 8/2008 |
| WO | 2008101943 A1 | 8/2008 |
| WO | 2008116179 A1 | 9/2008 |
| WO | 2008116195 A2 | 9/2008 |
| WO | 2008130615 A1 | 10/2008 |
| WO | 2008131149 A2 | 10/2008 |
| WO | 2009022007 A1 | 2/2009 |
| WO | 2009022010 A1 | 2/2009 |
| WO | 2009035969 A1 | 3/2009 |
| WO | 2009091082 A1 | 7/2009 |
| WO | 2009099734 A1 | 8/2009 |
| WO | 2009121945 A2 | 10/2009 |
| WO | 2009123194 A1 | 10/2009 |
| WO | 2010045656 A2 | 4/2010 |
| WO | 2010049678 A2 | 5/2010 |
| WO | 2010072776 A1 | 7/2010 |
| WO | 2010092123 A1 | 8/2010 |
| WO | 2010092124 A1 | 8/2010 |
| WO | 2010092125 A1 | 8/2010 |
| WO | 2010092126 A1 | 8/2010 |
| WO | 2010119990 A1 | 10/2010 |
| WO | 2010138535 A1 | 12/2010 |
| WO | 2011039107 A1 | 4/2011 |
| WO | 2011039108 A2 | 4/2011 |
| WO | 2011039337 A1 | 4/2011 |
| WO | 2011060290 A2 | 5/2011 |
| WO | 2011120923 A1 | 10/2011 |
| WO | 2012031124 A2 | 3/2012 |
| WO | 2012062698 A1 | 5/2012 |
| WO | 2012065993 A1 | 5/2012 |
| WO | 2012106303 A1 | 8/2012 |
| WO | 2012107476 A1 | 8/2012 |
| WO | 2012120040 A1 | 9/2012 |
| WO | 2012163990 A1 | 12/2012 |
| WO | 2013007557 A1 | 1/2013 |
| WO | 2013106547 A1 | 7/2013 |
| WO | 2013131967 A1 | 9/2013 |
| WO | 2013139777 A1 | 9/2013 |
| WO | 2014011926 A1 | 1/2014 |
| WO | 2014161918 A1 | 10/2014 |
| WO | 2014161919 A1 | 10/2014 |
| WO | 2014170383 A1 | 10/2014 |
| WO | 2016046150 A1 | 3/2016 |

OTHER PUBLICATIONS

Van Der Meer, Victor et al. "Chronic kidney disease in patients with diabetes mellitus type 2 or hypertension in general practice" (2010) British Journal of General Practice, 60, 884-890.

Veltkamp, Stephan A et al. "[1127-P] The Effect of Renal Impairment on the Pharmacokinetics and Urinary Glucose Excretion of the SGLT2 Inhibitor ASP1941 in Type 2 Diabetes Mellitus Patients" Clinical Therapeutics/New Technology, A309-A310.

Vepsalainen, T. et al. "Proteinuria modifies the effect of systolic blood presure on total and cardiovascular disease mortality in patients with type 2 diabetes" (2012) Journal of Internal Medicine, 611-619.

Vervoort, G. et al. "Glomerular hyperfiltration in type 1 diabetes mellitus results from primary changes in proximal tubular sodium handling without changes in vol. expansion" (2005) European Journal of Clinical Investigation vol. 35, pp. 330-336.

Wagman, Allan S. et al. "Current Therapies and Emerging Targets for the Treatment of Diabetes" (2001) Current Pharmaceutical Design, vol. 7, No. 6, 417-450.

Wallace, Debra J., et al.; Cyclopropylboronic Acid: Synthesis and Suzuki Cross-Coupling Reactions; Tetrahedron Letters (2002) vol. 43 pp. 6987-6990; Pergamon Press.

Wang et al., "Modern diagnosis and treatment of common cardiovascular diseases", Jul. 31, 2013, Shanxi Science and Technology Press, 1st Edition, p. 32 (English Abstract).

Wang Y et al: "BI-1356. Dipeptidyl-peptidase IV inhibitor, antidiabetic agent" Drugs of the Future, Prous Science, ES,vol. 33, No. 6, Jun. 1, 2008, pp. 473-477.

Wang, Xiao-jun et al. "Efficient Synthesis of Empagliflozin, an Inhibitor of SGLT-2, Utilizing an AlCl3-Promoted Silane Reduction of a ß-Glycopyranoside" (2014) American Chemical Society, vol. 16, 4090-4093.

Wanner, Christoph et al. "Empagliflozin and Clinical Outcomes in Patients with Type 2 Diabetes, Established Cardiovascular and Chronic Kidney Disease" (2017) Circulation, American Heart Association, 66 pgs.

Wanner, Christoph et al. "Empagliflozin and Progression of Kidney Disease in Type 2 Diabetes" (2016) The New England Journal of Medicine, (Study Protocol, 296 pgs).

Wanner, Christoph et al. "Empagliflozin and Progression of Kidney Disease in Type 2 Diabetes" (2016) The New England Journal of Medicine, (Supplementary Appendix, pp. 1-25).

Wanner, Christoph et al. "Empagliflozin and Progression of Kidney Disease in Type 2 Diabetes" (2016) The New England Journal of Medicine, 1-12.

Washburn, William N. "Dapagliflozin, A Selective SGLT2 Inhibitor for Treatment of Diabetes" (2015) Successful Drug Discovery, p. 87-112.

Washburn, William N. et al. "Differentiating sodium-glucose cotransporter-2 inhibitors in development for the treatment of type 2 diabetes mellitus" (2013) Expert Opinion on Investigational Drugs, 22:4, 463-486.

Weber, Ann E. "Dipeptidyl Peptidase IV Inhibitors for the Treatment of Diabetes" (2004) J. Med. Chem., 47, 4135-4141.

Websters Third New International Dictionary, Editor: GOVE, definition of prevent; 1963, 2 pgs.

Weinberg, Aviva E. et al. "Diabetes Severity, Metabolic Syndrome and the Risk of Erectile Dysfunction" (2013) International Society for Sexual Medicine 10:3, 3102-3109.

(56) References Cited

OTHER PUBLICATIONS

Wettergren, Andre et al. "Truncated GLP-1 (Proglucagon 78-107-Amide) Inhibits Gastric and Pancreatic Functions in Man" (1993) Digestive Diseases and Sciences, vol. 38, No. 4, 665-673.
WHO Drug Information, 2010, vol. 24, No. 4, p. 366.
Wielert-Badt, Susanne et al. "Probing the Conformation of the Sugar Transport Inhibitor Phlorizin by 2D-NMR, Molecular Dynamics Studies, and Pharmacophore Analysis" (2000) J. Med. Chem., vol. 43, 1692-1698.
Wielert-Badt, Susanne et al. "Single Molecule Recognition of Protein Binding Epitopes in Brush Border Membranes by Force Microscopy" (2002) Biophysical Journal, vol. 82, 2767-2774.
Woerle Hans-Juergen et al. "Safety and Efficacy of Empagliflozin as Monotherapy or Add-on to Metformin in a 78-Week Open-Lable Extension Study in Patients with Type 2 Diabetes" Presentation Abstract, 49-LB, (2012) 4 pg.
Wolff, Manfred E., et al., "Burger's Medicinal Chemistry and Drug Discovery, Fifth Edition, vol. 1, Principles and Practices", (1995) Wiley-Interscience Publication pp. 975-977.
Woo, Vincent C. "Dapagliflozin: where does it fit in the treatment of type 2 diabetes" (2009) Expert Opinion on Pharmacotherapy, 10(15): 2527-2535.
Woo, Vincent, "Empagliflozin/linagliptin single-tablet combination: first-in-class treatment option", The International Journal of Clinical Practice, 2015, vol. 69, No. 12, 1427-1437.
Woo, Young Sup et al. "Blood pressure changes during clozapine or olanzapine treatment in Korean schizophrenic patients" (2009) The World Journal of Biological Psychiatry, vol. 10(4); pp. 420-425.
Wood David, et al. "Established and emerging cardiovascular risk factors", (2001) American Heart Journal, 2001, vol. 141, No. 2, Suppl. S49-S57.
Wouters, Annelies, et al. "Synopsis: An Open-Label Study to Investigate the Absorption, Metabolism and Excretion of JNJ-28431754 in Healthy Male Subjects Following a Single Oral Dose Administration of C-JNJ-28431754" (2009) Clinical Study Report Synopisis, Protocol No. 28431754-NAP-1006, 5 pgs "Web Publication".
Wu, Ren-Rong et al. "Lifestyle Intervention and Metformin for Treatment of Antipsychotic-Induced Weight Gain, A Randomized Controlled Trial" Journal of American Medical Association (2008) V 299, pp. 185-193.
Xue, Song., et al; Zinc-mediated Synthesis of Alpha-C-Glycosided from 1,2-Anhydroglycosides; Synletters (2003) vol. 6 pp. 870-872.
Yale, J.F. et al. "Efficacy and safety of canagliflozin in subjects with type 2 diabetes and chronic kidney disease" Diabetes, Obesity and Metabolism (2013) vol. 15, Abstract "Web Publication".
Yale, J.F. et al. "Efficacy and safety of canagliflozin in subjects with type 2 diabetes and chronic kidney disease" Diabetes, Obesity and Metabolism (2013) vol. 15, pp. 463-473.
Yale, J.F. et al. "Efficacy and safety of canagliflozin in subjects with type 2 diabetes and chronic kidney disease" Diabetes, Obesity and Metabolism (2013) vol. 15, pp. 463-473 (18 pgs) "Web Publication".
Yale, J.F. et al. "Efficacy and safety of canagliflozin in subjects with type 2 diabetes and chronic kidney disease" Diabetes, Obesity and Metabolism (2013) vol. 15, pp. 463-473 (22 pgs) "Web Publication".
Yale, J.F. et al. "Efficacy and safety of canagliflozin in subjects with type 2 diabetes and chronic kidney disease" Diabetes, Obesity and Metabolism (Mar. 2013) vol. 15, 24 pgs, [online], [retrieved on Sep. 6, 2018]. Retrieved from the Internet <URL: <https://onlinelibrary.wiley.com/doi/full/10.1111/dom.12090>>.
Yale, Jean-Francois et al. "Canagliflozin (CANA), a Sodium Glucose Co-Transporter 2 (SGLT2) Inhibitor, Improves Glycemia and is Well Tolerated in Type 2 Diabetes Mellitus (T2DM) Subjects with Moderate Renal Impairment" Presentation Abstract, 41-LB, (2012) 1 pg.
Yale, Jean-Francois et al. "Canagliflozin (CANA), a Sodium Glucose Co-Transporter 2 (SGLT2) Inhibitor, Improves Glycemia and is Well Tolerated in Type 2 Diabetes Mellitus (T2DM) Subjects with Moderate Renal Impairment" (2012) Canadian Journal of Diabetes, Abstract 139, S40-41.
Yale, Jean-Francois et al. "Canagliflozin, a Sodium Glucose Co-Transporter 2 Inhibitor, Improves Glycemia and Is Well Tolerated in Type 2 Diabetes Mellitus Subjects with Moderate Renal Impairment" Jun. 8, 2012, Poster presented at the 72nd Scientific Session of the American Diabetes Association, 2 pgs.
Yamada, Yuichiro et al. "Clinic: Careful Progress in the Field and new Therapeutic Methods" Medical Online, (2007) vol. 220, No. 13, pp. 1219-1221.
Yamout, Hala et al. "Efficacy and Safety of Canagliflozin in Patients with Type 2 Diabetes and Stage 3 Nephropathy" (2014) Am J Nephrol, 40: 64-74.
Yancy, Clyde et al., "2013 ACCF/AHA Guideline for the Management of Heart Failure", Circulation, 2013, vol. 128, No. 16, e240-e327.
Yao, Chun-Hsu et al. "Discovery of Novel N-b-D-Xylosylindole Derivatives as Sodium-Dependent Glucose Cotransporter 2 (SGLT2) Inhibitors for the Management of Hyperglycemia in Diabetes" (2011) J. Med. Chem. Vol 54, pp. 166-178.
Young, Kerry Dooley "FDA panel rejects new empagliflozin indication for type 1 diabetes" (2019) Clinical Endocrinology News, 4 pgs.
Yu, Pan Chang et al., "The importance of glycated haemoglobin (HbAic) and postprandial glucose (PPG) control on cardiovascular outcomes in patients with type 2 diabetes", (2010) Diabetes Research and Clinical Practice, vol. 89, No. 1, 1-9.
Abdul-Ghani, Muhammad "Where does Combination Therapy with an SGLT2 Inhibitor Plus a DPP-4 Inhibitor Fit in the Management of Type 2 Diabetes?" (2015) Diabetes Care, 38, 373-375.
Abdul-Ghani, Muhammad A. et al. "Efficacy and Safety of SGLT2 Inhibitors in the Treatment of Type 2 Diabetes Mellitus" (2012) Curr Diab Rep 12: 230-238.
Abdul-Ghani, Muhammad A. et al. "Role of Sodium-Glucose Cotransporter 2 (SGLT 2) Inhibitors in the Treatment of Type 2 Diabetes" (2011) Endocrine Reviews, 32(4), 515-531.
Abstract ASN09L1_307a "Contact View (TH-P0751) Kidney Function and Response to Diabetes in Mice Lacking SGLT2", Vallon, Volker et al., Oct. 29, 2009, 1 pg.
Abstract ASN09L1_4153a, "Contact View (SA-P02723) Chronic SGLT2 Blockade Reduces Proximal Reabsorption and Normalizes State of Tubuloglomerular Feedback Activation in Hyperfiltering Diabetic Rats" Thomson, Scott et al., Oct. 31, 2009, 1 pg.
Adachi, Tetsuya., et al; T-1095, A Renal Na+-Glucose Transporter Inhibitor, Improves Hyperglycemia in Streptozotocin-Induced Diabetic Rats; Metabolism (2000) vol. 49 No. 8 pp. 990-995.
Agarwal, Ashok et al. "Role of Oxidative Stress in the Pathophysiological Mechanism of Erectile Dysfunction" (2006) Journal of Andrology, V 27, No. 3, 335-347.
Ahren, Bo "Dipeptidyl Peptidase-4 Inhibitors" (2007) Diabetes Care, vol. 30, No. 6, 1344-1350.
Ahren, Bo et al. "Twelve- and 52-Week Efficacy of the Dipeptidyl Peptidase IV Inhibitor LAF237 in Metformin-Treated Patients with Type 2 Diabetes" (2004) Diabetes Care, vol. 27, No. 12, 2874-2880.
Aires, Ines et al. "BI-10773, a sodium-glucose cotransporter 2 inhibitor for the potential oral treatment of type 2 diabetes mellitus" (2010) Current Opinion in Investigational Drugs, vol. 11 (10), pp. 1182-1190.
American Diabetes Association "Consensus Development Conference on Antipyschotic Drugs and Obesity and Diabetes" (2004) Diabetes Care, vol. 27, No. 2, pp. 596-601.
American Diabetes Association "Diagnosis and Classification of Diabetes Mellitus" Diabetes Care, vol. 33, Supplement 1, Jan. 2010. pp. S62-S69.
American Diabetes Association "Standards of Medical Care in Diabetes—2009" vol. 32, Supplement 1, S13-61.
Anker, S.D. et al., "Empagliflozin in Heart Failure with a Preserved Ejection Fraction" The New England Journal of Medicine, 2021, vol. 383, No. 16, 1451-1461.

(56) References Cited

OTHER PUBLICATIONS

Anonymous "Efficacy and Safety of Empagliflozin (BI 10773) in Patients with Type 2 Diabetes and Renal Impairment" Jan. 8, 2013, XP055120166, www.clinicaltrials.gov/ct2/show/study/NCT01164501?term=empagliflozin&rank=26.
Anonymous "Prevalence of Chronic Kidney Disease and Associated Risk Factors—United States, 1999-2004", Mar. 2, 2007, XP055119515, http://www.cdc.gov/mmwr/preview/mmwrhtml/mm5608a2.htm.
Anonymous, "Composition with a High Drug Load of Empagliflozin" Feb. 26, 2016, 3 pgs.
Aronow, Wibert S. "What should the blood pressure goal be in patients with hypertension who are at high risk for cardiovascular disease?" (2012) Hospital Practice, vol. 40, Issue 4, 2154-8331.
Ashiya, Mona et al. "Non-insulin therapies for type 2 diabetes" (2007) Nature Reviews, Drug Discovery vol. 6, 777-778.
Assaly, Rana et al. "Added Benefit of Empagliflozin: Improvement of Erectile Dysfunction in Diabetic Type 2 Rats" (2015) XP-002758690, AN: PREV201500747898; 2 pgs.
Assaly, Rana et al. "The Favorable Effect of Empagliflozin on Erectile Function in an Experimental Model of Type 2 Diabetes" (2018) The Journal of Sexual Medicine, 1-11.
Ault Addison, "Techniques and experiments for organic chemistry" University Science Books, 1998, pp. 59-60.
Aulton, Michael E. "Pharmaceutics, The Science of Dosage Form Design" (2002) 2nd Edition, 404-409.
Baati, Rachid et al. "A Convenient Synthesis of 2-Tetrahydrofuranyl Ethers" (2000) Organic Letters, vol. 2, No. 4, 485-487.
Baggio, Laurie L. et al. "Biology of Incretins: GLP-1 and GIP" Gastroenterology (2007) vol. 132, 2131-2157.
Bailey, Clifford J. "Renal Glucose Reabsorption Inhibitors to Treat Diabetes" (2011) Trends in Pharmacological Sciences, vol. 32, No. 2, 63-71.
Bailey, Clifford J. et al. "Diabetes therapies in renal impairment" The British Journal of Diabetes and Vascular Disease, (2012) vol. 12, Issue 4, 167-171.
Banker, Gilbert S et al. "Modern Pharmaceutics, Third Edition, Revised and Expanded" (1996) Marcel Dekker, p. 596.
Baptista, Trino et al. "Pharmacological Management of Atypical Antipsychotic-Induced Weight Gain" (2008) CNS Drugs, 22, 6, pp. 478-495.
Barnett, Anthony H. et al. "Efficacy and safety of empagliflozin added to existing antidiabetes treatments in patients with type 2 diabetes and chronic kidney disease: a randomised, double-blind, placebo-controlled trial" The Lancet, (2014) vol. 2, pp. 369-384.
Baron, Kyle T. et al. "Population Pharmacokinetics and Exposure-Response (Efficacy and Safety/Tolerability) of Empagliflozin in Patients with Type 2 Diabetes" (2016) Diabetes Ther, 7: 455-471.
Basile, Jan et al."The potential of sodium glucose cotransporter (SGLT2) inhibitors to reduce cardiovasular risk in patients with type 2 diabetes (T2DM)" (2013) Journal of Diabetes and its Complications, 27, 280-286.
Basu, Ansu et al. "New Treatment Options for Erectile Dysfunction in Patients with Diabetes Mellitus" (2004) Drugs, 64 (23), 2667-2688.
Bauer, Kurt H. et al. "Pharmazeutische Technologie" (1993) p. 293.
Benhaddou, Rachida., et al; Tetra-n-Propylammonium Tetra-Oxoruthenate(VII): A Reagent of Choice for the Oxidation of Diversely Protected Glycopyranoses and Glycofuranoses to Lactones; Carbohydrate Research (1994) vol. 260 pp. 243-250.
Bloomgarden, Zachary T. "Diabetes Treatment" Diabetes Care, (Mar. 2009) vol. 32, No. 3 pp. e25-e30.
Boards of Appeal of the European Patent Office, "Method of administering bisphosphonates" (2017) Application No. 05012711.7, EPA form 3030, 43 pgs "Web Publication".
Boards of Appeal of the European Patent Office, "Oral Administration of Calcitonin" (2017) Application No. 03766387.9, EPA form 3030, 12 pgs.
Boards of Appeal of the European Patent Office, "Pirfenidone therapy avoiding fluvoxamine" (2018) Application No. 10250379.4, EPA form 3030, 29 pgs.

Boehringer Ingelheim "Boehringer Ingelheim and Eli Lilly and Company announce positive top-line pivotal Phase III data results for empagliflozin*" (2013) 5 pgs.
Boehringer Ingelheim International GmbH, letter to EPO, EP Application No. 14715274.8 dated Jan. 8, 2020, 7 pgs.
Boehringer Ingelheim, "Clinical Study Synopsis for Public Disclosure, BI Trial No. 1245.10 Synopsis" May 15, 2014, 21 pgs.
Boehringer Ingelheim, "Clinical Study Synopsis for Public Disclosure, BI Trial No. 1245.12 Synopsis" (2011) 8 pgs.
Boehringer Ingelheim, "Clinical Study Synopsis for Public Disclosure, BI Trial No. 1245.19 Synopsis" May 15, 2014, 9 pgs.
Boehringer Ingelheim, "Clinical Study Synopsis for Public Disclosure, BI Trial No. 1245.23 Synopsis" May 15, 2014, 17 pgs.
Boyda, Heidi N et al. "Preclinical models of antipsychotic drug-induced metabolic side effects" (2010) Trends in Pharmacological Sciences vol. 31, pp. 484-497.
Branco, Ana et al., "Ketogenic diets: from cancer to mitochondrial diseases and beyond", European Journal of Clinical Investigation, 2016, vol. 46, No. 3, 285-298.
Brazg, R et al. "Effect of Adding MK-0431 to Ongoing Metformin Therapy in Type 2" (2005) Diabetes, vol. 54, Suppl. 1, A3.
Bristol-Myers Squibb Company, Label "Glucophage (metformin hydrochloride) Tablets, Glucophage XR (metformin hydrochloride) Extended-Release Tablets" Apr. 2017, 35 pgs.
British National Formulary, (2008) 358-359.
Response dated Sep. 25, 2008 to Non-Final Office Action dated Apr. 2, 2008 from U.S. Appl. No. 11/674,839, filed Feb. 14, 2007.
Response dated Sep. 25, 2008 to Non-Final Office Action dated Apr. 2, 2008 from U.S. Appl. No. 11/742,612, filed May 1, 2007.
Revesz, Lasslo., et al; SAR of Benzoylpylpyridines and Benzophenones as p38 Alpha MAP Kinase Inhibitors with Oral Activity; Bioorganic & Medicinal Chemistry Letters (2004) vol. 14 pp. 3601-3605.
Revocation of corresponding European patent EP 2981271. May 19, 2021, 1 pg.
Richardson, H. et al. "Effects of rosiglitazone and metformin on pancreatic beta cell and gene expression" (2006) Diabetologia V 49, pp. 685-696.
Riddle, Matthew C. "Oral Pharmacologic Management of Type 2 Diabetes" (1999) American Family Physician, 60(9), 2613-2620.
Rieusset, Jennifer et al. "Insulin Acutely Regulates the Expression of the Peroxisome Proliferator-Activated Receptor-y in Human Adipocytes" (1999) Diabetes, vol. 48, pp. 699-705.
Ritchie, C.W. et al. "The impact upon extra-pyramidal side effects, clinical symptoms and quality of life of a switch from conventional to atypical antipsychotics (risperidone or olanzapine) in elderly patients with schizophrenia" (2003) International Journal of Geriatric Psychiatry, vol. 18, pp. 432-440.
Robinson, J.A. "Chemical and Biochemical Aspects of Polyether-lonophore Antibiotic Biosynthesis" (1991) Progress in the Chemistry of Organic Natural Products, 1-81.
Roett, Michelle A. et al."Diabetic Nephropathy—The Family Physician's Role" (2012) vol. 85, No. 9, 884-889.
Romeo, June H. et al. "Sexual Function in Men with Diabetes Type 2: Association with Glycemic Control" (2000) The Journal of Urology, vol. 163, 788-791.
Rosenstock, J. et al. "Efficacy and safety of empagliflozin, a sodium glucose cotransporter (SGLT2) inhibitor, as add-on to metformin in type 2 diabetes with mild hyperglycemia" (2013) Diabetes, Obesity and Metabolism, 15: 1154-1160.
Rosenstock, J. et al. "Impact of empagliflozin added on to basal insulin in type 2 diabetes inadequately controlled on basal insulin: a 78-week randomized, double-blind, placebo-controlled trial" (2015) Diabetes, Obesity and Metabolism, 17: 936-948.
Rosenstock, Julio et al. "Dual Add-on Therapy in Type 2 Diabetes Poorly Controlled with Metformin Monotherapy: A Randomized Double-Blind Trial of Saxagliptin Plus Dapagliflozin Addition Versus Single Additon of Saxagliptin or Dapagliflozin to Metformin" (2015) Diabetes Care, vol. 38: 376-383.
Rosenstock, Julio et al. "Improved Glucose Control with Weight Loss, Lower Insulin Doses, and No Increased Hypoglycemia with Empagliflozin Added to Titrated Multiple Daily Injections of Insulin in Obese Inadequately Controlled Type 2 Diabetes" (2014) Diabetes Care, vol. 37, pp. 1815-1823.

(56) References Cited

OTHER PUBLICATIONS

Rudnic, Edward et al. "Oral Solid Dosage Forms" Remington—The Science and Practice of Pharmacy, 21th Ed, (2005) Chapter 45, Multiple Compressed Tablets, p. 890.
Rudnic, Edward et al. "Oral Solid Dosage Forms" Remington's Pharmaceutical Sciences, 18th Ed, Gennaro, A.R. Ed, Macie Pub. Co. (1990) pp. 1633-1665.
Ryder, Robert EJ et al., "Diabetes medications with cardiovascular protection in the wake of EMPA-REG Outcome: the optimal combination may be metformin, pioglitazone and empagliflozin" The British Journal of Diabetes & Vascular Disease, 2015, vol. 15, No. 4, 151-154.
Röhrig, Bernd et al., "Sample Size Calculation in Clinical Trials", (2010) Dtsch Arztebl Int, vol. 107 (31-32), pp. 552-556.
Scheen, Andre J. "Pharmacokinetic considerations for the treatment of diabetes in patients with chronic kidney disease" (2013) Expert Opinion on Drug Metabolism and Toxicology, 9:5, 529-550.
Schernthaner, G et al. "How attractive is the combination of a sodium glucose co-transporter 2 inhibitor with a dipeptidyl peptidase 4 inhibitor in the treatment of type 2 diabetes" (2015) Diabetes, Obesity and Metabolism, 17, 613-615.
Schneider, Cornelia et al. "Doubling of serum creatinine and the risk of cardiovascular outcomes in patients with chronic kidney disease and type 2 diabetes mellitus: a cohort study" (2016) Clinical Epidemiology, 8, 177-184.
Scotti, Lorenza et al. "Cost-Effectiveness of Enhancing Adherence to Therapy with Blood Pressure-Lowering Drugs in the Setting of Primary Cardiovascular Prevention" (2013) Value in Health, 16, 318-324.
Scottish Medicines Consortium, Product Assessment "dapagliflozin 5mg and 10mg (Forxiga)" Sep. 2012, 14 pgs.
Seman, Leo et al. "Empagliflozin (BI 10773), a Potent and Selective SGLT2 Inhibitor, Induces Dose-Dependent Glucosuria in Healthy Subjects" (2013) Clinical Pharmacology in Drug Development, vol. 2, Issue 2, 20 pgs.
Setter, Stephen M. et al. "Metformin Hydrochloride in the Treatment of Type 2 Diabetes Mellitus: A Clinical Review with a Focus on Dual Therapy" (2003) Clinical Therapeutics, vol. 25, No. 12, 2991-3026.
Shannon, James A. et al. "The Excretion of Inulin, Xylose and Urea by Normal and Phlorizinized Man" New York University College of Medicine, Department of Physiology, Feb. 13, 1935, 393-401.
Sherwin, Robert S. et al. "The Prevention or Delay of Type 2 Diabetes" Diabetes Care, (2002) vol. 25, No. 4, pp. 742-749.
Shioi, Atsushi "Vascular Calcification and Remodeling in Diabetes" (2010) The Journal of Japanese College of Angiology, vol. 50, No. 5, 561-567.
Shubrook, Jay et al., "Empagliflozin in the treatment of type 2 diabetes: evidence to date", Drug Design, Development and Therapy, 2015, vol. 9, 5793-5580.
Shurraw, Sabin et al. "Association between Glycemic Control and Adverse Outcomes in People with Diabetes Mellitus and Chronic Kidney Disase" (2011) Arch Intern Med. 171(21), 1920-1927.
Silverman, et al. "Handbook of Grignard Reagents" Marcel Dekker (1996) p. 82.
Singhal, Dharmendra et al. "Drug polymorphism and dosage form design: a practical perspective" Advanced Drug Delivery Reviews, 56, (2004) pp. 335-347.
Skrtic, Marko et al. "Characterisation of glomerular haemodynamic responses to SGLT2 inhibition in patients with type 1 diabetes and renal hyperfiltration" (2014) Diabetolgia, 4 pgs.
Snorek, Sharon M. et al. "PQRI Recommendations on Particle-Size Analysis of Drug Substances Used in Oral Dosage Forms" (2007) Journal of Pharmaceutical Sciences, vol. 96, No. 6, 1451-1467.
Softeland, Eirik et al. "Empagliflozin as Add-on Therapy in Patients with Type 2 Diabetes Inadequately Controlled With Linagliptin and Metformin: A 24-Week Randomized, Double-Blind, Parallel-Group Trial" (2016) Diabetes Care, DOI:10.2337/dc16-1347, pp. 1-9.
Solomon, Scott et al., "Influence of Nonfatal Hospitalization for Heart Failure on Subsequent Mortality in Patients With Chronic Heart Failure", (2007) Circulation, vol. 116, 1482-1487.
Sommer, Michael Bech., et al; displacement of Halogen of 2-Halogeno-Substituted Benzonitriles with Carbonions. Preparation of (2-Cyanoaryl)arylacetonitriles; Journal of Organic Chemistry (1990) vol. 55 pp. 4817-4821.
Song, Fujian et al. "What is indirect comparsion?" (2009) Hayward Medical Communications, www.whatisseries.co.uk, 6 pgs.
Sortino, Maria Angela et al. "Linagliptin: a thorough characterization beyond its clinical efficacy" (2013) Frontiers in Endocrinology, 4(16), 1-9.
Stazi, Federica., et al; Statistical Experimental Design-Driven Discovery of room-Temperature Conditions for Palladium-Catalyzed Cyanation of Aryl Bromides; Tetrahedron Letters (2005) vol. 46 1815-1818; Elsevier Ltd.
Stella, Valentino J. "Prodrugs as therapeutics" (2004) Ashley Publications, vol. 14, No. 3, pp. 277-280.
Stenlof, K. et al. "Efficacy and safety of canagliflozin monotherapy in subjects with type 2 diabetes mellitus inadequately controlled with diet and exercise" (2013) Diabetes, Obesity and Metabolism 15, 372-382.
Strack, Thomas "Metformin: A Review" (2008) Drugs of Today, 44(4), 303-314.
Sturtevant Inc. "Micronizer Jet Mill" (2000), 6 pgs.
Sun, Zhigang et al. "Particle Size Specifications for Solid Oral Dosage Forms: A Regulatory Perspective" (2010) American Pharmaceutical review, vol. 13, Issue 4, 1-14.
Supplementary Data "Supplementary Table 1. Exposure to ipragliflozin in plasma in two cohorts and Geometric Mean Ratio (GMR) of AUCinf and Cmax of ipragliflozin in T2DM patients with different degrees of renal impairment" (2013) American Diabetes Association. 1 pg, Published online at http://care.diabetesjournals.org/lookup/suppl/doi: 10.2337/dc12-1503/-/DCI "Web Publication".
Suzuki, Masayuki et al. "Tofogliflozin, a Potent and Hightly Specific Sodium/Glucose Cotransporter 2 Inhibitor, Improves Glycemic Control in Diabetic Rats and Mice" The Journal of Pharmacology and Experimental Therapeuticals, vol. 341, No. 3 pp. 692-701.
Suzuki, Yoshihiko et al: "Gain of muscle strength in mitochondrial diabetes treated with SGLT2 inhibitors", Diabetes Research and Clinical Practice, Poster Presentations, 2016, 120S1, S80, PB-15.
Svegliati-Baroni, Gianluca et al. "Glucagon-like peptide-1 receptor activation stimulates hepatic lipid oxidation and restores hepatic signalling alteration induced by a high-fat diet in nonalcholic steatohepatitis" (2011) LIver International, vol. 31, 9, pp. 1285-1297.
Non-Final Office Action dated Jun. 24, 2008 from U.S. Appl. No. 11/406,971, filed Apr. 19, 2006.
Non-Final Office Action dated Jun. 5, 2008 from U.S. Appl. No. 11/408,899, filed Apr. 21, 2006.
Non-Final Office Action dated Mar. 10, 2017 from U.S. Appl. No. 14/855,576, filed Sep. 16, 2015.
Non-Final Office Action dated May 8, 2008 from U.S. Appl. No. 11/359,846, filed Feb. 22, 2006.
Notice of Allowance and Fee(s) Due dated Jan. 13, 2009 from U.S. Appl. No. 11/304,284, filed Dec. 15, 2005.
Notice of Allowance and Fee(s) Due dated Dec. 30, 2008 from U.S. Appl. No. 11/674,839, filed Feb. 14, 2007.
Notice of Allowance and Fee(s) Due dated Feb. 3, 2009 from U.S. Appl. No. 11/359,846, filed Feb. 22, 2006.
Notice of Allowance and Fee(s) Due dated Jan. 2, 2009 from U.S. Appl. No. 11/742,612, filed May 1, 2007.
Office Action mailed Mar. 10, 2017, U.S. Appl. No. 14/918,713, filed Oct. 21, 2015, first named inventor Uli Christian Broedl.
Oku, Akira., et al; T-1095, An Inhibitor or renal Na+-Glucose Cotransporters, May Provide a Novel Approach to Treating Diabetes; Diabetes (1999) vol. 48 pp. 1794-1800.
Opposition to corresponding European Patent EP2981271 B1 (Application 14715578.2); "Summons to Attend Oral Proceedings and preliminary opinion of the Opposition Division—List of References" (2020) 27 pgs.
Opposition to corresponding European Patent EP2981271 B1 (Application 14715578.2); Declaration of Bernd Fussman and Policy on

(56) References Cited

OTHER PUBLICATIONS

Transparency and Publication of Clinical Study Data submitted by the Patent Proprietor (2020) 6 pgs.
Opposition to corresponding European Patent EP2981271 B1 (Application 14715578.2); Notice of Opposition, Opponent: Alfred E. Tiefenbacher (Aug. 16, 2019) 20 pgs.
Opposition to corresponding European Patent EP2981271 B1 (Application 14715578.2); Notice of Opposition, Opponent: Egis Gyogyszergyar Zartkoruen Mukodo Reszvenytarsasag (Aug. 22, 2019) 25 pgs.
Opposition to corresponding European Patent EP2981271 B1 (Application 14715578.2); Notice of Opposition, Opponent: Generics (U.K.) Limited, (Aug. 22, 2019) 25 pgs.
Opposition to corresponding European Patent EP2981271 B1 (Application 14715578.2); Notice of Opposition, Opponent: Krka, d.d., Novo Mesto (Aug. 12, 2019) 28 pgs.
Opposition to corresponding European Patent EP2981271 B1 (Application 14715578.2); Notice of Opposition, Opponent: Richard Gillard (Aug. 22, 2019) 31 pgs.
Opposition to corresponding European Patent EP2981271 B1 (Application 14715578.2); Notice of Opposition, Opponent: STADA Arzneimittel AG (Aug. 22, 2019) 24 pgs.
Opposition to corresponding European Patent EP2981271 B1 (Application 14715578.2); Notice of Opposition, Opponent: Teva Pharmaceutical Industries Ltd. (Aug. 22, 2019) 11 pgs.
Opposition to corresponding European Patent EP2981271 B1 (Application 14715578.2); Notice of Opposition, Opponent: Zaklady Farmaceutyczne Polpharma S.A. (Aug. 22, 2019) 31 pgs.
Opposition to corresponding European Patent EP2981271 B1 (Application 14715578.2); Observation to the summons and the Opposition Division's preliminary opinion submitted by the Patent Proprietor (2020) 39 pgs.
Osorio, Horacio et al. "Sodium-Glucose Cotransporter Inhibition Prevents Oxidative Stress in the Kidney of Diabetic Rats" (2012) Oxidative Medicine and Cellular Longevity, vol. 2012, Article ID 542042, 7 pgs.
Pan, Feng et al. "Intracavernosal Pressure Recording to Evaluate Erectile Function in Rodents" (2018) Journal of Visualized Experiments, vol. 136, e56798, 1-7.
Pan, Qi et al. "Changes of streptomycin induced type I diabetes mellitus in serum oxygen free radicals and antioxidant function thereof in rats" (2006) Journal of China, Prescription Drug, vol. 56, pp. 65-66.
Panchapakesan, Usha et al. Effects of SGLT2 Inhibition in Human Kidney Proximal Tubular Cells—Renoprotection in Diabetic Nephropathy? PLOS one, (2013) vol. 8, Issue 2, e54442, 8 pgs.
Patane, Giovanni et al. "Metformin Restores Insulin Secretion Altered by Chronic Exposure to Free Fatty Acids or High Glucose, A Direct Metformin Effect on Pancreatic b-Cells" (2000) Diabetes, vol. 49, pp. 735-740.
Patil, Basanagouda M. et al. "Elevation of systolic blood pressure in an animal model of olanzapine induced weight gain" (2006) European Journal of Pharmacology, vol. 551, pp. 112-115.
Perez Lopez, G. et al. "Sodium-glucose cotransporter 2 (SGLT2) inhibitors: from renal glycosuria to the treatment of type 2 diabetes mellitus" (2010) Nefrologia, 30(6) 618-625.
Perkins, Bruce A. et al. "Sodium-Glucose Cotransporter 2 Inhibition and Glycemic Control in Type 1 Diabetes: Results of an 8-Week Open-Label Proof-of-Concept Trial" (2014) Diabetes Care, vol. 37, pp. 1480-1483.
Perner, Richard J., et al; 5,6,7-Trisubstituted 4-Aminopyrido[2,3-d]pyrimidines as Novel inhibitors of Adenosime Kinase; Journal of Medicinal Chemistry (2003) vol. 46 pp. 5249-5257.
Pham, David et al. "Impact of empagliflozin in patients with diabetes and heart failure" (2017) Trends in Cardiovascular Medicine, vol. 27, pp. 144-151.
Phe, V. et al. "Erectile dysfunction and diabetes: A review of the current evidence based medicine and a synthesis of the main available therapies" (2012) Diabetes & Metabolism, 38, 1-13.
Ping, Li "Research Progress On the Effect of Hyperglycemia on Islet B-Cell Function" (2002) Department of Endocrinology, First Hospital of Xi'an Jiaotong University, Xi'an Shaanxi, 242-244.
Piya, Milan K. et al. "Emerging treatment options for type 2 diabetes" British Journal of Clinical Pharmacology, (2010) vol. 70, No. 5, pp. 631-644.
Plosker, Greg L. "Dapagliflozin: A Review of Its Use in Patients with Type 2 Diabetes" (2014) Drugs, 74, 2191-2209.
Poole, Chris D. et al. "The prescription cost of managing people with type 1 and type 2 diabetes following initiation of treatment with either insulin glargine or insulin detemir in routine general practice in the UK: a retrospective database analysis" (2007) Current Medical Research and Opinion, vol. 23, S. 1, pp. S41-S48.
Powers, Richard E. et al. "Understanding the Side Effects of Neuroleptics" (2008) Bureau of Geriatric Psychiatry/DETA, pp. 17-24.
Pratley, Richard E. et al. "Inhibition of DPP-4: a new therapeutic approach for the treatment of type 2 diabetes" (2007) Current Medical Research and Opinion, vol. 23, No. 4, 919-931.
Printz, Richard L. et al. "Tweaking the Glucose Sensor: Adjusting Glucokinase Activity with Activator Compounds" Endocrinology, (2005) vol. 146, No. 9, pp. 3693-3695.
Profit, Louise et al. "Vildagliptin: the evidence for its place in the treatment of type 2 diabetes mellitus" (2008) Core Evidence, 3(1), 13-30.
Proschan, Michael et al. "How much effect of different antihypertensive medications on cardiovascular outcomes is attributable to their effects on blood pressure?" (2013) Statistics in Medicine, 32, 884-897.
Pschyrembel et al. Clinical Dictionary, 257th Edition, Diabetes Mellitus, (1993) 320-321.
Rainier, Jon D. et al. "Aluminum- and Boron-Mediated C-Glycoside Synthesis from 1,2-Anhydroglycosides" Organic Letters, (2000) vol. 2, No. 17, pp. 2707-2709.
Randzio, Stanislaw L. et al. "Metastability and Instability of Organic Crystalline Substances" J. Phys. Chem. (2008) 112, pp. 1435-1444.
Reason, S.L. et al.: "Can a Low-Carbohydrate Diet Improve Exercise Tolerance in Mcardle Disease?", Journal of Rare Disorders: Diagnosis & Therapy, 2017, vol. 3, 1-5.
Redenti, Enrico et al. "Drug/Cyclodextrin/Hydroxy Acid Multicomponent Systems. Properties and Pharmaceutical Applications" Journal of Pharmaceutical Sciences, (2000) vol. 89, No. 1, pp. 1-8.
Redon, Josep "The Importance of 24-Hour Ambulatory Blood Pressure Monitoring in Patients at Risk of Cardiovascular Events" (2013) High Blood Press Cardiovasc Prev, 20, 13-18.
Remington, The Science and Practice of Pharmacy, 20th Edition, (2000) "Dissolution, Chapter 35" pp. 654-658, 713-714, 884-885 and 1114-1115.
Response dated Jun. 15, 2017 to Non-Final Office Action dated Mar. 10, 2017 from U.S. Appl. No. 14/855,576, filed Sep. 16, 2015.
Response dated Nov. 5, 2008 to Non-Final Office Action dated May 8, 2008 from U.S. Appl. No. 11/359,846, filed Feb. 22, 2006.
Swarbrick et al., "Handbook of Pharmaceutical Granulation Technology" Second Edition, (2005) 451-452.
Swarbrick et al., Encyclopedia of Pharmaceutical Technology, 2nd Edition, (2002) 4 pgs.
Swedberg, Karl et al., "Treatment of diabetes and heart failure: joint forces" European Heart Journal, 2016, vol. 37, No. 19, 1535-1537.
Tahrani, Abd A. et al. "SGLT inhibitors in management of diabetes" Lancet Diabetes Endocrinol (2013), 1, 140-151.
Takakura, Shoji et al. "Effect of ipragliflozin, an SGLT2 inhibitor, on progression of diabetic microvascular complications in spontaneously diabetic Torii fatty rats" (2016) Life Sciences, 147, 125-131.
Takebayashi, Kohzo et al. "Effect of Sodium Glucose Cotransporter 2 Inhibitors With Low SGLT2/SGLT1 Selectivity on Circulating Glucagon-Like Peptide 1 Levels in Type 2 Diabetes Mellitus" (2017) J Clin Med Res., vol. 9, (9) 745-753.
Tanaka, Chikako "Therapeutic Drugs for Metabolic Diseases, Chapter 2" (2002) New Yakurigaku (New Pharmacology) pp. 524-527.
Testa, Bernard "Prodrug research: futile or fertile?" (2004) Biochemical Pharmacology vol. 68, pp. 2097-2106.

(56) References Cited

OTHER PUBLICATIONS

The American Association of Clinical Endocrinologists Medical Guidelines for the Management of Diabetes Mellitus: The AACE System of Intensive Diabetes Self-Management—2002 Update, (2002) Endocrine Practice, vol. 1, Supp 1, 43 pgs.

Third party observations filed in corresponding EP application No. EP20100703652. Nov. 14, 2019, 6 pgs.

Thomas, L., "Chronic treatment with the Dipeptidyl Peptidase-4 Inhibitor BI 1356[9R)-8-(3-Amino-piperidin-1-yl)-7-but-2-ynyl-3-methyl-1(4-methyl-quinazolin-2-ylmethyl)-3,7-dihydro-purine-2,6-dione] Increases Basal Glucagon-Like Peptide-1 and Improves Glycemic Control in Diabetic Rodent Models" The Journal of Pharmacology and Experimental Therapeutics, Feb. 2009, vol. 328, No. 2, 556-563.

Thomas, Leo "Long-term treatment with empagliflozin, a novel, potent and selective SGLT-2 inhibitor, improves glycaemic control and features of metabolic syndrome in diabetic rats" (2012) Diabetes, Obesity and Metabolism, vol. 14, No. 1, 94-96.

Thomas, Leo et al. "(R)-8-(3-Amino-piperidin-1-yl)-7-but-2-ynyl-3-methyl-1-(4-methyl-quinazolin-2-ylmethyl)-3,7-dihydro-purine-2,6-dione (BI 1356), a Novel Xanthine-Based Dipeptidyl Peptidase 4 Inhibitor, Has a Superior Potency and Longer Duration of Action Compared with Other Dipeptidyl Peptidase-4 Inhibitors" Journal of Pharmacology and Experimental Therapeutics (2008) 325, pp. 175-182.

Thomson, Scott C. et al. "Acute and chronic effects of SGLT2 blockade on glomerular and tubular function in the early diabetic rat" (2011) Am J Physiol Regul Integr Comp Physiol, V 302, pp. R75-R83.

Thornber, C.W. et al. "Isosterism and Molecular Modification in Drug Design" (1979) Imperial Chemical Industries Limited, Pharmaceuticals Division, Mereside, Alderley Park, Macclesfield, Cheshire, pp. 563-580.

Threlfall, Terry "Structural and Thermodynamic Explanations of Ostwald's Rule" Organic Process Research & Development (2003) vol. 7, pp. 1017-1027.

Torrance, Christopher J. et al. "Combinatorial chemoprevention of intestinal neoplasia" (2000) Nature Medicine, vol. 6, No. 8, 1024-1028.

Tsuchihashi-Makaya, Miyuki et al. "Characteristics and Outcomes of Hospitalized Patients with Heart Failure and Reduced vs Preserved Ejection Fraction" (2009) Circulation Journal, vol. 73, 1893-1900.

Tsujihara, Kenji et al. "Na+-Glucose Cotransporter (SGLT) Inhibitors as Antidiabetic Agents. 4. Synthesis and Pharmacological Properties of 4'-Dehydroxyphlorizin Derivatives Substituted on the B Ring" J. Med. Chem. (1999) vol. 42, pp. 5311-5324.

Tsujihara, Kenji et al. "Na+-Glucose Cotransporter Inhibitors as Antidiabetics. I. Synthesis and Pharmacological Properties of 4'Dehydroxyphlorizin Derivatives Based on a New Concept" (1996) Chem. Pharm. Bull. 44(6), 1174-1180.

Turner, Robert C. et al. "UKPDS Group: Intensive blood-glucose control with sulphonylureas or insulin compared with conventional treatment and risk of complications in patients with type 2 diabetes (UKPDS 33)" (1998) The Lancet, 352, 837-853.

Twigger, Simon N. "Meeting Report of Rats and Men: The Rat Genome and Comparative Genomics" Genome Biology (2004) vol. 5, Issue 3, Article 314, 2 pgs.

Tykwinski, Rik R; Evolution in the Palladium-Catalyzed Cross-Coupling of sp- and sp2-Hybridized Carbon Atoms; Angew Chemical International Edition (2003) vol. 42 pp. 1566-1568.

U.S. Appl. No. 12/892,310, filed Sep. 28, 2010. Inventor: Dirk Weber.

U.S. Appl. No. 12/892,326, filed Sep. 28, 2010. Inventor: Dirk Weber.

U.S. Appl. No. 12/894,385, filed Sep. 30, 2010. Inventor: Peter Schneider.

U.S. Appl. No. 13/079,424, filed Apr. 4, 2011. Inventor: Matthias Eckhardt.

U.S. Appl. No. 13/287,216, filed Nov. 2, 2011. Inventor: Rolf Grempler.

U.S. Appl. No. 13/367,739, filed Feb. 7, 2012. Inventor: Thomas Klein.

U.S. Appl. No. 13/413,702, filed Mar. 7, 2012. Inventor: Masanori Ito.

U.S. Appl. No. 13/637,413, filed Sep. 26, 2012. Inventor: Rolf Grempler.

U.S. Appl. No. 13/693,239, filed Dec. 4, 2012. Inventor: Klaus Dugi.

U.S. Appl. No. 13/785,365, filed Mar. 5, 2013. Inventor: Masanori Ito.

U.S. Appl. No. 13/833,097, filed Mar. 15, 2013. Inventor: Eric Williams Mayoux.

U.S. Appl. No. 14/244, 196 filed Apr. 3, 2014. Inventor: Uli Christian Broedl.

U.S. Appl. No. 14/244,208, filed Apr. 3, 2014. Inventor: Uli Christian Broedl.

U.S. Appl. No. 14/253,935, filed Apr. 16, 2014. Inventor: Uli Christian Broedl.

U.S. Appl. No. 15/918,477, filed Mar. 12, 2018. Inventor: Uli Christian Broedl.

U.S. Appl. No. 15/945,236, filed Apr. 4, 2018. Inventor: Uli Christian Broedl.

U.S. Food and Drug Administration, Code of Federal Regulations, Section 312 of Title 21, Apr. 1, 2013, 44 pgs.

U.S. Appl. No. 12/545,175 filed Aug. 21, 2009, Inventor: Matthias Eckhardt.

Ueta, Kiichiro., et al; Long-Term Treatment with the Na+-Glucose Cotransporter Inhibitor T-1095 Causes Sustained Improvement in Hyperglycemia and Prevents Diabetic Neuropathy in Goto-Kakizaki Rats; Life Sciences (2005) vol. 76 pp. 2655-2668.

United States Pharmacopoeia, The National Formulary, (2005) USP 28, NF 23, p. 2711.

Unknown "Intensification of Development of SGLT inhibitor—New Alternative of Antidiabetic" Aug. 21, 2007; 2 pgs; http://www.yakuji.co.jp/entry4100.html.

US Department of Health and Human Services, CDER, FDA, "Guideline for Submitting Supporting Documentation in Drug Applications for the Manufacture of Drug Substances" Feb. 1987, 48 pages.

US Department of Health and Human Services, FDA, Endocrinologic and Metabolic Drugs Advisory Committee; Notice of Meeting, Federal Register, vol. 76, No. 80, Apr. 26, 2011, 23324-23325.

US Department of Health and Human Services, FDA, "Guidance for Industry, Diabetes Mellitus—Evaluating Cardiovascular Risk in New Antidiabetic Therapies to Treat Type 2 Diabetes" Dec. 2008, 8 pages.

US Department of Health and Human Services, FDA, "Guidance for Industry, Pharmacokinetics in Patients with Impaired Renal Function—Study Design, Data Analysis, and Impact on Dosing and Labeling" May 1998, 19 pages.

US Department of Health and Human Services, FDA, Center for Drug Evaluation and Research "Application No. 204629Orig1s000 Summary Review (Jardiance)" 2014, 20 pages.

U.S. Appl. No. 14/805,838, Third-party submission under 37 CFR 1.290 mailed on Dec. 12, 2016. 19 pgs.

Buhler, Volker "Kollidon® Polyvinylpyrrolidone excipients for the pharmaceutical industry" 9th revised edition, Mar. 2008, 1-331.

Busch, Frank R. et al. "Grignard Reagents—Industrial Applications and Strategy", Grignard Reagents, New Developments, John Wiley & Sons Ltd, copyright (2000), pp. 165-183.

Buysschaert, M. "Empagliflozin (Jardiance®) A Novel Hypoglycemic Agent in the Treatment of Type 2 Diabetes, Also Reduces Cardiovascular Risk: Analysis of a Princeps Study" (2015) Louvain Med 134(8), 403-408.

Byrn, Stephen et al. "Pharmaceutical Solids: A Strategic Approach to Regulatory Considerations" Pharmaceutical Research, vol. 12, No. 7, (1995) pp. 945-954.

Cahill, George F. Jr. et al.: "Ketoacids? Good Medicine?", Transactions of the American Clinical and Climatological Association, 2003, vol. 114, 149-161.

(56) References Cited

OTHER PUBLICATIONS

Caira, Mino R. "Crystalline Polymorphism of Organic Compounds" (1998) Topics in Current Chemistry, vol. 198, 164-208.
Campbell, R. Keith "Rationale for Dipeptidyl Peptidase 4 Inhibitors: A New Class of Oral Agents for the Treatment of Type 2 Diabetes Mellitus" (2007) The Annals of Pharmacotherapy, vol. 41, 51-60.
Cartledge, JJ et al. "Endothelial and neuronal-derived nitric oxide mediated relaxation of corpus cavernosal smooth muscle in a rat, in vitro, model of erectile function" (2000) International Journal of Impotence Research, vol. 12, 213-221.
Castelhano, Arlindo L. et al. "Reactions of an Electrophilic Glycine Cation Equivalent With Grignard Reagents a Simple Synthesis ff ß,g-Unsaturated Amino Acids" (1986) Tetrahedron Letters, vol. 27, No. 22, pp. 2435-2438.
Center for Drug Evalutaion and Research, Application No. 204629Orig1s000, NDA 204-629, (2014) Clinical Pharmacology and Biopharmaceutics Review, Office of New Drug Quality Assessment, 3 pgs.
Cernea Simona et al. "ß-Cell Protection and Therapy for Latent Autoimmune Diabetes in Adults" Diabetes Care (2009) vol. 32, Supplement 2, pp. S246-S252.
Cetrone, Michela et al. "Effects of the antidiabetic drugs on the age-related atrophy and sarcopenia associated with diabetes type II" Current Diabetes Reviews (2014) vol. 10, No. 4, pp. 231-237.
Chen, L. H. et al. "Inhibition of the sodium glucose co-transporter-2: its beneficial action and potential combination therapy for type 2 diabetes mellitus" Diabetes, Obesity and Metabolism, (2013) vol. 15, pp. 392-402.
Chen, Lu-Lu "1000 questions about endocrine metabolic disease" Hubei Changjiang Publishing Group, Aug. 2006, ISBN 7-5352-3595-6, 3 pages.
Cherney, David et al. "The effect of sodium glucose cotransporter 2 inhibition with empagliflozin on microalbuminuria and macroalbuminuria in patients with type 2 diabetes" (2016) Diabetologia, 11pgs.
Cherney, David Z.I. et al. "Pooled analysis of Phase III trials indicate contrasting influences of renal function on blood pressure, body weight, and HbA1c reductions with empagliflozin" (2017) Kidney International, 1-14.
Cherney, David Z.I. et al. "Renal Hemodynamic Effect of Sodium-Glucose Cotransporter 2 Inhibition in Patients with Type 1 Diabetes Mellitus" Circulation, (2014) V 129, pp. 587-597.
Cherney, David Z.I et al. "The effect of empagliflozin on arterial stiffness and heart rate variability in subjects with uncomplicated type 1 diabetes mellitus" (2014) Cardiovascular Diabetology, 13:28, 8 pgs.
Chow, Francis CC, et al. "Challenges in achieving optimal glycemic control in type 2 diabetes patients with declining renal function: The Southeast Asia perspective" Journal of Diabetes Investigation, (2012) vol. 3, Issue 6, pp. 481-489.
Chyan, Yau-Jan, et al. "Dipeptidyl Peptidase-IV Inhibitors: An Evolving Treatment for Tyep 2 Diabetes from the Incretin Concept" (2007) Recent Patents on Endocrine, Metabolic & Immune Drug Discovery, vol. 1, No. 1, 15-24.
Clinical Trial: NCT01131676, BI 10773 (Empagliflozin) Cardiovascular Outcome Trial in Type 2 Diabetes Mellitus Patients (EMPA-REG Outcome) May 16, 2016.
Clinical Trials: NCT00328172 "Efficacy and Safety of 3 Doses of BI1356 (Linagliptin) in Type 2 Diabetes Patients" Sponsor: Boehringer Ingelheim, Last Update Posted Mar. 14, 2014, 4 pgs.
Clinical Trials: NCT00554450 "Renal Impairment in Type 2 Diabetic Subjects" Sponsor: AstraZeneca, Last Update Posted Oct. 17, 2016, 5 pgs.
Clinical Trials: NCT01011868 "Efficacy and Safety of BI 10773 in Combination with Insulin in Patients with Type 2 Diabetes" Sponsor: Boehringer Ingelheim Pharmaceuticals, Oct. 18, 2010, 3 pgs.
Clinical Trials: NCT01064414 "An Efficacy, Safety and Tolerability Stude of Canagliflozin in Patients with Type 2 Diabetes Mellitus who have Moderate Renal Impairment" Sponsor: Janssen Research & Development LLC, Last Update Posted Aug. 14, 2013, 7 pgs.
Clinical Trials: NCT01131676. "BI 10773 Cardiovascular Outcome Event Trail in Type 2 Diabetes Mellitus Patients" Sponsor: Boehringer Ingelheim Pharmaceuticals, Updated date: Dec. 13, 2012. 4 pgs.
Clinical Trials: NCT01131676. "BI 10773 Cardiovascular Outcome Event Trail in Type 2 Diabetes Mellitus Patients" Sponsor: Boehringer Ingelheim Pharmaceuticals, Updated date: Mar. 7, 2012. 5 pgs.
Clinical Trials: NCT01131676. "BI 10773 Cardiovascular Outcome Event Trail in Type 2 Diabetes Mellitus Patients" Sponsor: Boehringer Ingelheim Pharmaceuticals, Updated date: May 26, 2010. 4 pgs.
Clinical Trials: NCT01131676. "BI 10773 Cardiovascular Outcome Event Trail in Type 2 Diabetes Mellitus Patients" Sponsor: Boehringer Ingelheim Pharmaceuticals, Updated date: Nov. 14, 2012. 4 pgs.
Clinical Trials: NCT01164501 "Efficacy and Safety of BI 10773 in Patients with Type 2 Diabetes and Renal Impairment" Sponsor: Boehringer Ingelheim Pharmaceuticals, Jul. 15, 2010, 4 pgs.
Clinical Trials: NCT01164501 "Efficacy and Safety of BI 10773 in Patients with Type 2 Diabetes and Renal Impairment" Sponsor: Boehringer Ingelheim Pharmaceuticals, Last Update Posted: Jun. 16, 2014, 6 pgs.
Clinical Trials: NCT01164501 "Efficacy and Safety of BI 10773 in Patients with Type 2 Diabetes and Renal Impairment" Sponsor: Boehringer Ingelheim Pharmaceuticals, Mar. 7, 2012, 3 pgs.
Clinical Trials: NCT01164501 "History of Changes for Study: NCT01164501, Efficacy and Safety of Empagliflozin (BI 10773) in Patients with Type 2 Diabetes and Renal Impairment" Sponsor: Boehringer Ingelheim, Lastest version Jan. 8, 2013, 14 pgs "Web-Publication".
Clinical Trials: NCT01164501 "History of Changes for Study: NCT01164501, Efficacy and Safety of Empagliflozin (BI 10773) in Patients with Type 2 Diabetes and Renal Impairment" Sponsor: Boehringer Ingelheim, Lastest version May 16, 2014, 14 pgs.
Clinical Trials: NCT01164501 "History of Changes for Study: NCT01164501, Efficacy and Safety of Empagliflozin (BI 10773) in Patients with Type 2 Diabetes and Renal Impairment" Sponsor: Boehringer Ingelheim, Lastest version May 16, 2014, 7 pgs.
Clinical Trials: NCT01167881. "Efficacy and Safety of Empagliflozin (BI 10773) With Metformin in Patients with Type 2 Diabetes" Sponsor: Boehringer Ingelheim Pharmaceuticals, Updated Date: Apr. 3, 2013, 4 pgs.
Clinical Trials: NCT01210001 "Efficacy and Safety of Empagliflozin (BI 10773) in Type 2 Diabetes Patients on a Background of Pioglitazone Alone or with Metformin" Sponsor: Boehringer Ingelheim, Last Update Posted Jun. 17, 2014, 7 pgs.
Clinical Trials: NCT01370005 "History of Changes for Study: NCT01370005, 12 week Efficacy and Safety Study of Empagliflozin (BI 10773) in Hypertensive Patients with Type 2 Diabetes Mellitus" Sponsor: Boehringer Ingelheim, Lastest version Jan. 22, 2016, 21 pgs.
Clinical Trials: NCT01422876 "Efficacy and Safety of Empagliflozin (BI 10773) / Linagliptin (BI 1356) Fixed Dose Combination in Treatment naive and Metformin Treated Type 2 Diabetes Patients" Sponsor: Boehringer Ingelheim Pharmaceuticals, Apr. 1, 2015, 4 pgs.
Clinical Trials: NCT01734785 "History of Changes for Study: NCT01734785, Safety and Efficacy of the Combination of Empagliflozin and Linaglitin Compared to Linagliptin Alone Over 24 Weeks in Patients with Type 2 Diabetes" Sponsor: Boehringer Ingelheim, Lastest version Jun. 9, 2016, 15 pgs.
Clinical Trials: NCT01778049 "History of Changes for Study: NCT01778049, Linagliptin as Add on Therapy to Empagliflozin 10mg or 25mg with Background Metformin in Patient with Type 2 Diabetes" Sponsor: Boehringer Ingelheim, Lastest version Mar. 4, 2016, 15 pgs.
Clinical Trials: NCT01778049 "Linagliptin as Add on Therapy to Empagliflozin 10mg or 25mg with Background Metformin in Patient with Type 2 Diabetes" Sponsor: Boehringer Ingelheim, Last update posted Apr. 4, 2016, 7 pgs.
Clinical Trials: NCT01778049 "Linagliptin as Add on Therapy to Empagliflozin 10mg or 25mg with Background Metformin in Patient with Type 2 Diabetes" Sponsor: Boehringer Ingelheim, Last update posted Jan. 29, 2013, 7 pgs "Web Publication".

(56) References Cited

OTHER PUBLICATIONS

Clinical Trials: NCT01811953 "History of Changes for Study: NCT01811953, Equivalence of Resorption of Empagliflozin/Metformin Administered as Combination Tablet Compared With Empagliflozin/Metformin as Single Tablets Administered Together" Sponsor: Boehringer Ingelheim, Lastest version Jun. 26, 2015, 6 pgs.

Clinical Trials: NCT01907113 "History of Changes for Study: NCT01907113, Pharmacokinetics, Pharmacodynamics, Safety and Tolerability of BI 10773 in Type II Diabetes Patients with Different Degrees of Renal Impairment" Sponsor: Boehringer Ingelheim, Lastest version Jul. 11, 2014, 6 pgs.

Clinical Trials: NCT01907113 "History of Changes for Study: NCT01907113, Pharmacokinetics, Pharmacodynamics, Safety and Tolerability of BI 10773 in Type II Diabetes Patients with Different Degrees of Renal Impairment" Sponsor: Boehringer Ingelheim, Lastest version Jul. 22, 2013, 6 pgs "Web Publication".

Colorcon; Opadry II Aqueous Film Coating; http://www.colorcon.com/products-formulation/all-products/film-coatings/immediate-release/opadry-II ; Dec. 31, 2015.

Crepaldi, G. et al. "Dipeptidyl peptidase 4 (DPP-4) inhibitors and their role in Type 2 diabetes management" (2007) J. Endocrinol. Invest., 30, 610-614.

Daniele, Giuseppe et al., "Dapagliflozin Enhances Fat Oxidation and Ketone Production in Patients With Type 2 Diabetes", Diabetes Care, 2016, vol. 39, 2036-2041.

Davidson, Jaime A. "SGLT2 inhibitors in patients with type 2 diabetes and renal disease: overview of current evidence" (2019) Postgraduate Medicine, 38 pgs.

Yuan, Yingjin. "Modern Pharmaceutical Technology", Chemical Industry Press, (2005) vol. 2, p. 75.

Zannad, Faiez et al., "Clinical outcome endpoints in heart failure trials: a European Society of Cardiology Heart Failure Association consensus document", (2013) European Journal of Heart Failure, vol. 15, 1082-1094.

Zannad, Faiez et al., "Diabetes clinical trials: helped or hindered by the current shift in regulatory requirements?", (2012) European Heart Journal, vol. 33, 1049-1057.

Zannad, Faiez et al., "Heart failure as an endpoint in heart failure and non-heart failure cardiovascular clinical trials: the need for a consensus definition", (2008) European Heart Journal, vol. 29, 413-421.

Zanoli, L. et al . "Sodium-Glucose Linked Transporter-2 Inhibitors in Chronic Kidney Disease" (2015) The Scientific World Journal, Article ID 317507, 6 pgs.

Zhang, L. et al."Dapagliflozin treatment in patients with different stages of type 2 diabetes mellitus: effects on glycaemic control and body weight" Diabetes, Obesity and Metabolism (2010) vol. 12, No. 6, p. 510-515.

Zhang, Wen Bin et al. "Renal SGLT2 inhibitors: A novel type of oral antidiabetic drug" (2010) Progress in Physiological Sciences, vol. 41, No. 6, 453-460.

Zhang, Wenbin et al. "EGT1442, a potent and selective SGLT2 inhibitor, attenuates blood glucose and HbA1c levels in db/db mice an prolongs the survival of stroke-prone rats" (2011) Pharmacological Research, vol. 63, pp. 284-293.

Zheng, Tiesheng et al. "Clinical Biochemistry Experimental Diagnosis and Case Analysis" (2010) China Medical Science and Technology Press, 201001, p. 152.

Zimmermann, Grant R. et al. "Multi-target therapeutics: when the whole is greater than the sum of the parts" (2007) Drug Discovery Today, vol. 12, 34-42.

Zinman Bernard et al., "Design of the Empagliflozin Cardiovascular (CV) Outcome Event Trial in Type 2 Diabetes (TSD)", (2013) Abstracts / Can J Diabetes, vol. 37, S29-S30.

Zinman, Bernard et al. "Empagliflozin, Cardiovascular Outcomes and Mortality in Type 2 Diabetes" (2015) The New England Journal of Medicine, 373:22 pp. 2117-2128.

Zinman, Bernard et al., "Design of the Empagliflozin Cardiovascular (CV) Outcome Event Trial in Type 2 Diabetes (T2D)" Canadian Journal of Diabetes, 2013, vol. 37, Supplement 4, S13eS84, 77.

Zinman, Bernard et al. "Empaglifozin, Cardiovasular Outcome and Mortality in Type 2 Diabetes", (2015) New England Journal of Medicine, vol. 373, 2117-2128.

List, James F et al. "Glucose dynamics and mechanistic implications of SGLT2 inhibitors in animals and humans" (2011) Kidney International, 79, Suppl 120, S20-S27.

Liu, Sheng et al. "Chemically induced (streptozotocin alloxan) diabetes mellitus in dogs" (2000) Bull Hunan Med University, vol. 25, No. 2, pp. 125-128 (English Translation).

Lu, Jiangqian et al. "Chapter 8, Treatment of heart failure iwth clinical conditions, Section II Treatment of heart failure complicated by arrhythmia" Feb. 28, 2015, Practical Handbook of Diagnosis and Treatment of Heart Failure, People's Military Medical Publishing House 1st Edition, p. 177 (English Abstract).

Luna, Beatriz et al. "Oral Agents in the Management of Type 2 Diabetes Mellitus" (2001) American Family Physician, vol. 63, No. 9, 1747-1756.

Ma, Terry KW. et al."Renin-angiotensin-aldosterone system blockade for cardiovascular diseases: current status" (2010) British Journal of Pharmacology, 160, 1273-1292.

MAAS Renke, et al., "Old and new cardiovascular risk factors: from unresolved issues to new opportunities" Atherosclerosis Supplements, 2003, vol. 4, 5-17.

Maayan, Lawrence et al. "Effectiveness of Medications Used to Attenuate Antipsychotic-Related Weight Gain and Metabolic Antipsychotic-Related Weight Gain and Metabolic Abnormalities: A Systematic Review and Meta-Analysis" (2010) Neuropsychopharmacology, vol. 35, pp. 1520-1530.

Macha, S. et al. "Pharmacokinetics, pharmacodynamics and safety of empagliflozin, a sodium glucose cotransporter 2 (SGLT2) inhibitor, in subjects with renal impairment" (2014) Diabetes, Obesity and Metabolism, 16: 215-222.

Macha, Sreeraj et al. "Pharmacokinetics of empagliflozin, a sodium glucose cotransporter 2 (SGLT2) inhibitor, and metformin following co-administration in healthy volunteers" (2013) International Journal of Clinical Pharmacology and Therapeutics, vol. 51, No. 2, pp. 132-140.

Maeda, Yasutaka et al. "Oxidative Stress" (2010) Nippon Rinsho, vol. 68, No. 5, 814-818.

Magee, G.M. et al. "Is hyperfiltration associated with the future risk of developing diabetic nephropathy? A meta-analysis" Diabetologia (2009) 52: pp. 691-697.

Malatiali, Slava et al. "Phlorizin Prevents Glomerular Hyperfiltration but not Hypertrophy in Diabetic Rats" (2008) Experimental Diabetes Research, vol. 2008, 7 pgs.

Marchetti, Piero et al. "Pancreatic Islets from Type 2 Diabetic Patients Have Functional Defects and Increased Apoptosis that are Ameliorated by Metformin" The Journal of Clinical Endocrinology & Metabolism, (2004) vol. 89,(11) pp. 5535-5541.

MARKS Jennifer B, et al. "Cardiovascular risk in diabetes: a brief review", (2000) Journal of Diabetes and its Complications, vol. 14, 108-115.

Matsuyama, Tatsuo et al. "Glucagon-like peptide-1 (7-36 amide): a potent glucagonostatic and insulinotropic hormone" Diabetes Research and Clincial Practice (1988) 5, 281-284.

Matzke, Gary R. et al. "Drug dosing consideration in patients with acute and chronic kidney disease—a clinical update from Kidney Disease: Improving Global Outcomes (KDIGO)" (2011) Kidney International, vol. 80, 1122-1137.

McCormack, James et al. "Seeing what you want to see in randomized controlled trials: versions and perversions of UKPDS data", BMJ, 2000, vol. 320, 1720-1723.

McGill, Janet B. et al. "Long-Term Efficacy and Safety of Linagliptin in Patients with Type 2 Diabetes and Severe Renal Impairment, A 1-year randomized, double-blind, placebo-controlled study" (2013) Diabetes Care, vol. 36, 237-244.

McHale, Mary "Grignard Reaction" Connexions module: m15245, (2007) pp. 1-18.

(56) References Cited

OTHER PUBLICATIONS

McKinney, James D et al. "The Practice of Structure Activity Relationships (SAR) in Toxicology" (2000) Toxicological Sciences, vol. 56, 8-17.

McLaughlin, Mark., et al; Suzuki-Miyaura Cross-Coupling of Benzylic Phospahates with Arylboronic Acids; Organic Letters (2005) vol. 7 No. 22 pp. 4875-4878.

McMaster University, Chem2006 Lab Manual, 1997/98, Expt 1, Part B, pp. 1-9.

Mende, Christian "Management of Chronic Kidney Disease: The Relationship between Serum Uric Acid and the Development of Nephropathy" (2015) Adv. Ther. 32, 1177-1191.

Meng, Wei et al."Discovery of Dapagliflozin: A Potent, Selective Renal Sodium-Dependent Glucose Cotransporter 2 (SGLT2) Inhibitor for the Treatment of Type 2 Diabetes" J. Med. Chem. (2008) vol. 51, pp. 1145-1149.

Merck Manual Online Edition, "Diabetes Mellitus" http://www.merckmanuals.com/professional/endocrine_and_metabolic_disorders/diabetes_mellitus_and_disorders of carbohyrate_metabolism/diabetes_mellitus_dm.html#v987998. last revision Jun. 2008 by Preeti Kishore M.D.

Merriam-Webster's Collegiate Dictionary, definition of prevent, published 1998 by Merriam-Webster Inc. p. 924.

Meyer, Timothy W. "Tubular injury in glomerular disease" (2003) Kidney International, vol. 63, p. 774-787.

Miller, Del D. "Review and Management of Clozapine Side Effects" (2000) J Clinc Psychiatry, 61 (Suppl 8) pp. 14-17.

Miyagawa, Junichiro et al. "Combined use between incretin-related meidcations and other medications" (2010) Diagnosis and Treatment, vol. 98, No. 3, 423-436.

Mogensen, Carl Erik "Perspectives in Diabetes Prediction of Clinical Diabetic Nephropathy in IDDM Patients Alternatives to Microalbuminuria?" Diabetes (1990) vol. 39, pp. 761-767.

Mojsov, Svetlana "Insulinotropin: Glucagon-like Peptide I (7-37) Co-encoded in the Glucagon Gene Is a Potent Stimulator of Insulin Release in the Perfused Rat Pancreas" J. Clin. Invest. (1987) vol. 79, 616-619.

Mooradian, Arsharg D. et al. "Narrative Review: A Rational Approach to Starting Insulin Therapy" (2006) Annals of Internal Medicine, vol. 145, pp. 125-134.

Munir, Kashif et al. "Differential pharmacology and clinical utility of empagliflozin in type 2 diabetes" (2016) Clinical Pharmacology: Advances and Applications, vol. 8, 19-34.

Murray, Michael "Encyclopedia of Nurtritional Supplements" (1996) pp. 283-287.

Musicki, B. et al. "Endothelial dysfunction in diabetic erectile dysfunction" (2007) International Journal of Impotence Research, vol. 19, 129-138.

Muskiet, Marcel H.A. et al., "Understanding EMPA-REG Outcome" The Lancet Diabetes & Endocrinology, 2015, vol. 3, No. 12, 928-929.

Musso, Giovanni et al., "A novel approach to control hyperglycemia in type 2 diabetes: Sodium glucose co-transport (SGLT) inhibitors. Systematic review and meta-analysis of randomized trials", (2012) Annals of Medicine, 44, 375-393.

Nair, S. et al. "From history to reality: sodium glucose co-transporter 2 inhibitors—a novel therapy for type 2 diabetes mellitus" (2010) Pract Diab Int, vol. 27, No. 7, pp. 311-316.

Nathan, D.M. et al. "Medical management of hyperglycemia in type 2 diabetes mellitus: a consensus algorithm for the initiation and adjustment of therapy" Diabetologia (2009) 52, 17-30.

Nathan, David M. et al. "Management of Hyperglycemia in Type 2 Diabetes: A Consensus Algorithm for the Initiation and Adjustment of Therapy" (2006) Diabetes Care, vol. 29, No. 8, 1963-1972.

National Institute for Health Research, Horizon Scanning Centre, "Empagliflozin for type 2 diabetes mellitus" Apr. 2012, 10 pgs.

National Kidney Foundation "Mild-to-moderate Chronic Kidney Disease" (2010) 5 pgs www.patient.co.uk.

National Kidney Foundation, "Clinical Practice Guidelines, For Chronic Kidney Disease: Evaluation, Classification and Stratification" (2002) 356 pgs.

Nauck, Michael A. et al. "Cardiovascular Actions and Clincial Outcomes with Glucagon-Like Peptide-1 Receptor Agonists and Dipeptidyl Peptidase-4 Inhibitors" Circulation (2017) vol. 136, 849-870.

Neamati, Ouri., et al;, "Depsides and Depsidones as Inhibiton of HIV-1 Integrase: Dimvery of Novel Inhibitors Through 3D Database Searclung", J. Med. Chem., 1997, vol. 40, pp. 942-951.

Negishi, Ei-ichi, et al. "Selective Carbon-Carbon Bond Formation via Transition Metal Catalysis. 3. A Highly Selective Synthesis of Unsymmetrical Biaryls and Diarylmethanes by the Nickel- or Palladium-Catalyzed Reaction of Aryl- and Benzylzinc Derivatives with Aryl Halides" (1977) Journal of Organic Chemistry, V 42, No. 10, 1821-1823.

Nishimura, Rimei et al, "Effect of empagliflozin monotherapy on postprandial glucose and 24-hour glucose variability in Japanese patients with type 2 diabetes mellitus: a randomized, double-blind, placebo-controlled, 4-week study", Cardiovascular Diabetology, 2015, vol. 14, No. 11, 1-13.

Nobre, Sabrina M., et al; Synthesis of Diarylmethane Derivatives from Pd-Catalyzed Cross-Coupling Reactions of Benzylic Halides with Arylboronic Acids; Tetrahedron Letters (2004) vol. 45 8225-8228.

Non Final Office Action dated Apr. 2, 2008 from U.S. Appl. No. 11/674,839, filed Feb. 14, 2007.

Non Final Office Action dated Apr. 2, 2008 from U.S. Appl. No. 11/742,612, filed May 1, 2007.

Deacon, Carolyn F. "Perspectives in Diabetes Therapeutic Strategies Based on Glucagon-Like Peptide 1" Diabetes, (2004) vol. 53 pp. 2181-2189.

Defronzo, Ralph A. et al. "Combination of Empagliflozin and Linagliptin as Second-Line Therapy in Subjects with Type 2 Diabetes Inadequately Controlled on Metformin" (2015) Diabetes Care, 38, 384-393.

Diabetes Mellitus, Merck Manual Online Edition, (retrieved Sep. 13, 2011) http://www.merckmanuals.com/professional/endocrine_and_metabolic_disorders/diabetes_mellitus_and_disorders_of_carbohydrate_metabolism/diabetes_mellitus_dm.html#v987998. Revision Jun. 2008.

Dohle, Wolfgang., et al; Copper-Mediated Cross-Coupling of Functionalized Arylmagnesium Reagents with Functionalized Alkyl and Benzylic Halides; Organic Letters (2001) vol. 3 No. 18 pp. 2871-2873.

Dokken, Betsy "The Kidney as a Treatment Target for Type 2 Diabetes" (2012) Diabetes Spectrum, vol. 25, No. 1, 29-36.

Drucker, Daniel J. et al. "Glucagon-like peptide I stimulates insulin gene expression and increases cyclic AMP levels in a rat islet cell line" (1987) Proc. Natl. Acad. Sci. USA, vol. 84, 3434-3438.

Drug Watch "Type 2 Diabetes Mellitus" Formulary vol. 43 Aug. 2008 p. 304.

DrugBank entries for Linagliptin (Accession No. DB08882), Sitagliptin (Accession No. DB01261) and Vitagliptin (Accession No. DB04876), downloaded Jan. 30, 2018, 12 pgs.

Drugbank. Metformin. Accession No. DB00331 (APRD01099) https://www.drugbank.ca/drugs/DB00331. Drug created on Jun. 13, 2005/Updated on May 9, 2017.

Du, Dong Hui "Challenges faced in primary care of diabetic patients with renal insufficiency" Diabetes World, Clinical Periodical, Nov. 2012, vol. 6, No. 11, 498-502.

Eade, Ronald E. "Extractives of Australian Timbers. XV* THe Synthesis of 7,4'-Di-O-methylbayin" (1975) Austr. J. Chemistry, vol. 28, pp. 2011-2018.

Eli Lilly "US FDA grants Fast Track designation to Jardiance® (empagliflozin) to improve outcomes following a heart attack" (2020) Lilly.com, News Release, 6 pgs.

Ekstrom, Nils et al. "Effectiveness and safety of metformin in 51675 patients with type 2 diabetes and different levels of renal function: a cohort study from the Swedish National Diabetes Register" (2012) BJM Open, 2, 10 pgs.

El-Hattab, Ayman W. et al., "MELAS syndrome: Clinical manifestations, pathogenesis, and treatment options", Molecular Genetics and Metabolism, 2015, vol. 116, 4-12.

(56) References Cited

OTHER PUBLICATIONS

Eli Lilly "Boehringer Ingelheim and Eli Lilly and Company announce positive top-line pivotal Phase III data results for empagliflozin" Jan. 7, 2013, 3 pgs.
Eli Lilly, "Boehringer Ingelheim Pharmaceuticals, Inc. and Eli Lilly and Company to Feature 30 Presentations on Type 1 and Type 2 Diabetes at the 72nd American Diabetes Assoiation Sceintific Sessions" (2012) 4 pgs.
Eli Lilly, "FDA approves Jardiance® (empagliflozin) tablets for adults with type 2 diabetes" (2014) Press Release, 4 pgs.
Ellinger, Lara K. et al. "Efficacy of Metformin and Topiramate in Prevention and Treatment of Second-Generation Antipsychotic-Induced Weight Gain" Annals of Pharmacotherapy (2010) vol. 44, No. 4, pp. 668-679.
Embase Database. Accession No. 0050872772. Jelsing, J et al. "Empagliflozin a novel sodium glucose cotransporter-2 inhibitor improves glucose homeostasis and preserves pancreatic beta cell mass in db/db mice" (2012) 2 pgs.
Embase database: Accession No. 0050781595. Jelsing, Jacob et al. "The sodium glucose cotransporter-2 (SGLT-2) inhibitor empagliflozin has a durable effect on the restoration of glucose homeostasis by preserving beta-cell mass in zucker diabetic fatty rats" (2012) 2 pgs.
Emea "CPMP—Note for Guidance on Clinical Investigation of Medicinal Products in the Treatment of Diabetes Mellitus" (2002) 12 pgs.
EP08787264.4, Applicant: Boehringer Ingelheim, Patent Claims, (2012) 3 pgs "Web Publication".
Ettmayer, Peter et al. "Lessons Learned from Marketed and Investigational Prodrugs" (2004) Journal of Medicinal Chemistry, vol. 47, No. 10, pp. 2393-2404.
European Medicines Agency "Assessment Report Jardiance, International non-proprietary name: Empagliflozin, Procedure No. EMEA/H/C/002677/0000" (2014) 99 pgs.
European Medicines Agency, "Guideline on clinical investigation of medicinal products in the treatment or prevention of diabetes mellitus" First published and updated May 14, 2012.
European Medicines Agency, ICH Topic Q6 A, "Specifications: Test Procedures and Acceptance Criteria for New Drug Substances and New Drug Products: Chemical Substances", 2000, 32 pgs.
European Medicines Agency, Science Medicines Health, "Assessment Report Forxiga dapagliflozin" (2012) 170 pgs.
European Patent Application 14715578.2, EP2981271; "Third party observations pursuant to article 115 EPC" (2017) 28 pgs.
European Patent EP2981271 B1 (Application 14715578.2); "Third party observations" Anonymous, (2019) 4 pgs.
European Patent Office: Decision revoking corresponding European patent EP 2981271. Jun. 25, 2021, 89 pgs.
Exhibit submitted on Dec. 14, 2017 in parent U.S. Appl. No. 14/918,727.
Farxiga, Prescribing Information, Reference ID 3433133, Manufactured by Bristol-Myers Squibb Company, published by the FDA on Jan. 8, 2014, 43 pgs.
Ferrannini et al., Supplementary Data, Diabetologia (2010) 53: [Suppl1], p S351.
Ferrannini, E. et al."Impact of chronic kidney disease and sodium-glucose cotransporter 2 inhibition in patients with type 2 diabetes" (2013) Diabetes Care, vol. 36, 1260-1265.
Ferrannini, E. et al. "A Phase IIb, randomized, placebo-controlled study of the SGLT2 inhibitor empagliflozin in patients with type 2 diabetes" (2013) Diabetes, Obesity and Metabolism, 15: 721-728.
Ferrannini, E. et al. "A Phase IIb, randomized, placebo-controlled study of the SGLT2 inhibitor empagliflozin in patients with type 2 diabetes" (2013) Diabetes, Obesity and Metabolism, vol. 15, Issue 8: Abstract "Web Publication".
Ferrannini, E. et al. "Long-Term Safety and Efficacy of Empagliflozin, Sitagliptin, and Metformin" (2013) Diabetes Care, vol. 36, 4015-4021.
Ferrannini, Ele et al. "CV Protection in the EMPA-REG Outcome Trial: A "Thrifty Substrate" Hypothesis" Diabetes Care, Jun. 11, 2016, pp. 1-7.

Ferrannini, Ele et al. "Metabolic response to sodium-glucose cotransporter 2 inhibition in type 2 diabetic patients" (2014) The Journal of Clinical Investigation vol. 124, No. 2, 499-508 and article amendment, p. 1868.
Ferrannini, Ele et al. "Renal Glucose Handling, Impact of chronic kidney disease and sodium-glucose cotransporter 2 inhibition in patients with type 2 diabetes" (2013) Diabetes Care, vol. 36, 1260-1265.
Ferrannini, Ele et al. "Renal Glucose Handling, Impact of chronic kidney disease and sodium-glucose cotransporter 2 inhibition in patients with type 2 diabetes" (2013) Diabetes Care, vol. 36, 1260-1265, "Web Publication".
Ferrannini, Ele et al. "Renal Glucose Handling: Impact of Chronic Kidney Disease (CKD) and SGLT2 Inhibition in Patients with Type 2 Diabetes" (2012) Clinical Diabetes/Therapeutics Posters, 1028-P, A264.
Ferrannini, Ele et al. "SGLT2 inhibition in diabetes mellitus: rationale and clinical prospects" (2012) Nat. Rev. Endocrinol. vol. 8, 495-502.
Fiese, Eugene F et al. "Preformulation" (1987) The Theory and Practice of Industrial Pharmacy, 28 pgs.
Final Office Action mailed Sep. 28, 2017. U.S. Appl. No. 14/855,576, filed Sep. 16, 2015. First Named Inventor: Uli Christian Broedl; 23 pgs.
Fiordaliso Fabio, et al. "Cardiovasular oxidative stress is reduced by an ACE inhibitor in a rat model of streptozotocin-induced diabetes", (2006) Life Sciences, vol. 79, 121-129.
Fioretto, Paola et al Efficacy and safety of dapagliflozin in patients with type 2 diabetes and moderate renal impairment (chronic kidney disease stage 3A): The DERIVE Study, (2018) Diabetes, Obesity and Metabolism, 20:2532-2540.
Fitchett, David et al. "Heart failure outcomes with empagliflozin in patients with type 2 diabetes at high cardiovascular risk: results of the EMPA-REG Outcome® trial" (2016) European Heart Journal vol. 37, pp. 1526-1534.
Foote, Celine et al. "Effects of SGLT2 inhibitors on cardiovascular outcomes" (2012) Diabetes & Vascular Disease Research, vol. 9, (2) pp. 117-123.
Fowler,Michael J. "Hypoglycemia" (2008) Clinical Diabetes, vol. 26, No. 4, 170-173.
International Search Report PCT/EP2016/059525 mailed Jun. 24, 2016. 4 pgs.
Invokana, Prescribing Information, Manufactured by Janssen Ortho LLC., published by the FDA on Mar. 29, 2013, 41 pgs.
Invokana, Press Release "U.S. FDA Approves INVOKANA™ (Canagliflozin) for the Treatment of Adults with Type 2 Diabetes" Janssen Pharmaceuticals, in partnership with Johnson & Johnson on Mar. 29, 2013, 7 pgs.
Inzucchi, Silvo E. "Oral Antihyperglycemic Therapy for Type 2 Diabetes" (2002) JAMA, vol. 287, No. 3, 360-372.
Isaji, Masayuki "Sodium-glucose cotransporter inhibitors for diabetes" Current Opinion in Investigational Drugs, (2007) vol. 8, No. 4, pp. 285-292.
Jabbour, S.A. et al. "Sodium glucose co-transporter 2 inhibitors: blocking renal tubular reabsorption of glucose to improve glycaemic control in patients with diabetes" (2008) Int J Clin Pract, 62, 8, 1279-1284.
Jabbour, Serge A. "The Importance of Reducing Hyperglycemia While Preserving Insulin Secretion—The Rational for Sodium-coupled Glucose Co-trnasporter 2 Inhibition in Diabetes" Touch Briefings, US Endocrinology (2009) pp. 75-78.
Jagdmann Jr, G. Erik ; Synthesis of 5-(4-Substituted Benzyl)-2,4-Diaminoquinazolines as Inhibitors of Candida Albicans Dihydrofolate Reductase; Journal Heterocyclic Chemical (1995) vol. 32 pp. 1461-1465.
Jardiance, Highlights of Prescribing Information, Boehringer Ingelheim, 2014, 28 pgs.
Jardiance, Product Information, Boehringer Ingelheim, Jun. 16, 2014, 47 pgs.
Jeremy, J.Y. et al. "Reactive oxygen species and erectile dysfunction: possible role of NADPH oxidase" (2007) International Journal of Impotence Research, 19, 265-280.

(56) References Cited

OTHER PUBLICATIONS

Johnson & Johnson "FDA Advisory Committee Recommends Approval of Canagliflozin for Treatment of Adults with Type 2 Diabetes" (2013) Press Release, 3 pgs.
Jones, Byrony "Empagliflozin—one step closer to glycaemic control in patients with type II diabetes and CKD?" (2014) Nature Reviews Nephrology 10, 181, 2 pgs.
Joshi, Shashank R. "Metformin: Old Wine in New Bottle—Evolving Technology and Therapy in Diabetes" Journal of Association of Physicians in India, (2005) vol. 53, pp. 963-972.
Kadowaki, T et al. "PPAR gamma agonist and antagonist" Nihon Yakurigaku Zasshi (2001) vol. 118, No. 9, pp. 321-326. (English abstract).
Kashihara, Naoki et al. "Renin-Angiotensin System" (2011) Angiotensin Research, vol. 8, No. 2, pp. 40(96)-46(102).
Kasichayanula, Sreeneeranj et al. "The Influence of Kidney Function on Dapagliflozin Exposure, Metabolism and Pharmacodynamics in Healthy Subjects and in Patients with Type 2 Diabetes Mellitus" (2012) British Journal of Clinical Pharmacology, vol. 76, Issue 3, pp. 432-444.
Katirji, Bashar et al. "Metabolic Myopathies", Oct. 19, 2016, 13 pgs, Retrieved from the Internet: < https://emedicine.medscape.com/article/1173338-print>.
Katsuno, Kenji et al. "Sergliflozin, a Novel Selective Inhibitor of Low-Affinity Sodium Glucose Cotransporter (SGLT2) Validates the Critical Role of SGLT2 in Renal Glucose Reabsorption and Modulates Plasma Glucose Level" The Journal of Pharmacology and Experimental Therapeutics (2007) vol. 320, No. 1, pp. 323-330.
Kautz, S. et al. "Early insulin therapy prevents beta cell loss in a mouse model for permanent neonatal diabetes (Munich Ins2C95s)" Diabetologia (2012) vol. 55, pp. 382-391.
Kdigo 2012 Clinical Practice Guideline for the Evaluation and Management of Chronic Kidney Disease (2013) vol. 3, Issue 1, 163 pgs.
Kharasch, M.S. et al. "Factors Determining the Course and Mechanisms of Grignard Reactions." Journal of American Chemical Society, (1941) vol. 63, 2316-2320.
Kitaoka, Yu et al., "Oxidative stress and Nrf2 signaling in McArdle disease", Molecular Genetics and Metabolism, 2013, vol. 110, 297-302.
Knochel, Paul et al. "Highly functionalized Organomagnesium Reagents Prepared through Halogen-Metal Exchange" Angew. Chem. INt. Ed. (2003) vol. 42, 4302-4320.
Kohan, Donald E. et al. "Abstract: [TH-PO524] Efficacy and Safety of Dapagliflozin in Patients with Type 2 Diabetes and Moderate Renal Impairment" Nov. 10, 2011, Abstract Sessions, 1 pg, http://www.abstracts2view.com.
Kohan, Donald E. et al. "Long-term study of patients with type 2 diabetes and moderate renal impairment shows that dapagliflozin reduces weight and blood pressure but does not improve glycemic control" (2013) Kidney International; 85, 962-971.
Kojima, Naoki et al. "Effects of a New SGLT2 Inhibitor, Luseogliflozin on Diabetic Nephropathy in T2DN Rats" The Journal of Pharmacology and Experimental Therapeutics, (2013) V 345, pp. 464-472.
Komala, Muralikrishan G. et al. "Sodium glucose cotransporter 2 and the diabetic kidney" (2013) Curr Opin Nephrol Hypertens, vol. 22, 113-119.
Koo, Ja Seo., et al; 2-Pyridyl Cyanate: A Useful Reagent for he Preparation of Nitriles; Synthetic Communications (1996) vol. 26 No. 20 pp. 3709-3713; Marcel Dekker, Inc.
Krasovskiy Arkady et al. "A LiCL-Mediated Br/Mg Exchange Reaction for the Preparation of Functionalized Aryl- and Heterarylmagnesium Compounds from Organic Bromides**" Angew. Chem. Int. Ed. (2004) vol. 43, pp. 3333-3336.
Kuribayashi, Takeshi., et al; Bis C-Glycosylated Diphenylmethanes for Stable Glycoepitope Mimetics; Syntletters (1999) vol. 6 pp. 737-740.
Kuribayashi, Takeshi., et al; c-Glycosylated Aryl tins: Versatile Building Blocks for Aryl C-Glycoside Glycomimetics; J. Carbohydrate Chemistry (1999) vol. 18, No. 4 pp. 371-382.
Kuribayashi, Takeshi., et al; C-Glycosylated Diphenylmethanes and Benzophenones: The Stille Coupling Reaction of C-Glycosylated Aryl tins with Benzyl Bromides and Acid Chlorides; J. Carbohydrate Chemistry (1999) vol. 18, No. 4 pp. 393-401.
Kuritzky, Louis "Addition of Basal Insulin to Oral Antidiabetic Agents: A Goal-Directed Approach to Type 2 Diabetes Therapy" (2006) MedGenMed. 8(4) 34, 19 pgs.
Lab Cat. "Strong and Weak Acids" Feb. 2007; https://cdavies.wordpress.com/2007/02/27/strong-and-weak-acids/.
Lancet "Getting to the heart of the matter in type 2 diabetes" Editorial, (2015) 1 pg.
Langle, Sandrine., et al; Selective Double Suzuki Cross-Coupling Reactions. Synthesis of Unsymmetrical Diaryl (or Heteroaryl) Methanes; Tetrahedron Letters (2003) vol. 44 pp. 9255-9258; Pergamon Press.
Langley, Alissa K, et al. "Dipeptidyl Peptidase IV Inhibitors and the Incretin System in Type 2 Diabetes Mellitus" (2007) Pharmacotherapy, vol. 27, No. 8, 1163-1180.
Larsen, Mogens Lytken et al. "Effect of Long-Term Monitoring of Glycosylated Hemoglobin Levels in Insulin-Dependent Diabetes Mellitus" (1990) The New England Journal of Medicine, vol. 323, No. 15, 1021-1025.
Lebovitz, Harold E. "Insulin secretagogues: old and new" (1999) Diabetes Review, vol. 7, 139-153.
Lehmann, Ule et al. "Palladium-Catalyzed Cross-Coupling Reactions between Dihydropyranylindium Reagents and Aryl Halides, Synthesis of C-Aryl Glycals" Organic Letters, 2003, vol. 5, No. 14, pp. 2405-2408.
Levetan, Claresa "Oral antidiabetic agents in type 2 diabetes" (2007) Current Medical Research and Opinion, vol. 23, No. 4, 945-952.
Levey, Andrew S. et al. "Definition and classification of chronic kidney disease: A position statement from Kidney Disease: Improving Global Outcomes (KDIGO)" (2005) Kidney International, vol. 67, 2089-2100.
Lewin, Andrew et al "Initial Combination of Empagliflozin and Linagliptin in Subjects with Type 2 Diabetes" (2015) Diabetes Care, vol. 38, 394-402.
Li, T, et al. "Lack of Pharmacokinetic Interaction between Dapagliflozin and Pioglitazone in Healthy Subjects" Journal of Clinical Pharmacology, (2009) vol. 49, No. 9, pp. 1093.
Li, Yazhou, et al. "Glucagon-like Peptide-1 Receptor Signaling Modulates b Cell Apoptosis" (2003) The Journal of Biological Chemistry, vol. 278, No. 1, 471-478.
Lieberman, Herbert A. et al. "Pharmaceutical Dosage Forms: Tablets, vol. 1" (1989) pp. 5-6.
Lieberman, Joseph A. "Metabolic Changes Associated with Antipsychotic Use" Prim Care Companion J Clinc Psychiatry (2004) 6, pp. 8-13.
Lipska, Kasia J. et al. "Use of Metformin in the Setting of Mild-to-Moderate Renal Insufficiency" (2011) Diabetes Care, vol. 34, 1431-1437.
Lipworth, Brian J. "Clinical pharmacology of b3-adrenoceptors" Br J Clin Pharmacol (1996) pp. 291-300.
Fowler, Michael J. "Microvascular and Macrovascular Complications of Diabetes" (2008) Clinical Diabetes, vol. 26, No. 2, 77-82.
Frey, Samuel et al., "The addition of ketone bodies alleviates mitochondrial dysfunction by restoring complex I assembly in a MELAS cellular model" Biochimica et Biophysica Acta, 2017, vol. 1863, No. 1, 284-291.
Friedrich, Christian et al . "A Randomized, Open-Label, Crossover Study to Evaluate the Pharmacokinetics fo Empagliflozin and Linagliptin After Coadministration in Healthy Male Volunteers" (2013) Clincial Therapeutics, vol. 35, No. 1, A33-A42.
Fuerstner, A. et al. "Iron-Catalyzed Cross-Coupling Reactions" (2002) Journal of the American Chemical Society, American Chemical Society, vol. 124, pp. 13856-13863.
Fuerstner, Alois., et al; Practical Method for the Rhodium-Catalyzed Addition of Aryl- and Alkenylboronic Acids to Aldehydes; Advanced Synthesis and Catalysis (2001) vol. 343 No. 4 pp. 343-350.
Fujii, Masakazu et al. "Oxidative Stress and Diabetic Vascular Diseases" (2009) Angiology Frontier, vol. 8, No. 1, pp. 47-54.
Fujimori, Yoshikazu et al. "Remogliflozin Etabonate in a Novel Category of Selective Low-Affinity Sodium Glucose Cotransporter

(56) References Cited

OTHER PUBLICATIONS (SGLT2) Inhibitors, Exhibits Antidiabetic Efficacy in Rodent Models" (2008) Journal of Pharmacology and Experimental Therapeutics vol. 327 No 1, pp. 268-276.
Ganguli, Pial "US, EU and Japanese filings in 2013 for BI /Lilly's empagliflozin in type 2 diabetes" (2013) Scrip, 2 pgs.
Gao, Frank et al., "Myopathy secondary to empagliflozin therapy in type 2 diabetes", Endocrinology, Diabetes & Metabolism, 2020, vol. 1, 1-4.
Garber, A.J. et al. "Vildagliptin in combination with pioglitazone improves glycaemic control in patients with type 2 diabetes failing thiazolidinedione monotherapy: a randomized, placebo-controlled study" (2007) Diabetes, Obesity and Metabolism, 9, 166-174.
Geddes, Colin C. et al. "Glomerular filtration rate—what is the rationale and justification of normalizing GFR for body surface area?" (2008) Nephrology Dialysis Transplantation, 23: 4-6.
Gennaro, Alfonso R. "Remington: The Science and Practice of Pharmacy" Twentieth Edition (2000) 4 pgs.
Gerstein, Hertzel C. et al. "The Hemoglobin A1c Level as a Progressive Risk Factor for Cardiovascular Death, Hospitalization for Heart Failure, or Death in Patients With Chronic Heart Failure", (2008) Arch Intern Med, vol. 168, No. 15, 1699-1704.
Ghassemi et al. "Synthesis and properties of new sulfonated poly(p. phenylene) derivatives for proton exchange membranes" Polymer (2004) pp. 5847-5854.
Ghosh, Raktim Kumar et al. "SGLT2 Inhibitors: A New Emerging Therapeutic Class in the Treatment of Type 2 Diabetes Mellitus" (2012) Journal of Clinical Pharmacology, 52, 457-463.
Gibson, M. et al. "Pharmaceutical Preformulation and Formulation" Second Edition, (2009) 402-407.
Giuliano, F. "New horizons in erectile and endothelial dysfunction research and therapies" (2008) International Journal of Impotence Research, 20, S2-S8.
Global Data "Pharmacokinetics, Pharmacodynamics, Safety and Tolerability of BI 10773 in Type II Diabetes Patients with Different Degrees of Renal Impairment" (2017) ClinicalTrials.gov, NCT01907113; 1245.12, 11 pgs.
Golay A. et al. "Link Between Obesity and Type 2 Diabetes" (2005) Best Practice & Research Clinical Endocrinology & Metabolism, vol. 19, No. 4, 649-663.
Goldberg, Lee R. Chapter 20, "Hypertension with Heart Failure", (2006) Advanced Therapy in Hypertension and Vascular Diseases, 169-175.
Goldstein, Barry J. et al. "Effect of Initial Combination Therapy with Sitagliptin, a Dipeptidyl Peptidase-4 Inhibitor and Metformin on Glycemic Control in Patients with Type 2 Diabetes" (2007) Diabetes Care, vol. 30, No. 8, 1979-1987.
Gong, Hegui et al. "A Room Temperature Negishi Cross-Coupling Approach to C-Alkyl Glycosides" (2007) Journal of the American Chemical Society, vol. 129, 1908-1909.
Goodchild, Emily et al. "Managing diabetes in the presence of renal impairment" (2017) Prescriber p. 24-30.
Goodwin, Nicole C. et al. "Novel L-Xylose Derivatives as Selective Sodium-Dependent Glucose Cotransporter 2 (SGLT2) Inhibitors for the Treatment of Type 2 Diabetes" (2009) Journal Medicinal Chemistry vol. 52 pp. 6201-6204.
Government of Canada, "Hypertension Facts and Figures" (2010) canada.ca, 2 pgs.
Graefe-Mody, E.U., et al., "Evaluation of the potential for steady-state pharmacokinectic and pharmacodynamic interactions between the DPP-4 inhibitor linagliptin and metformin in healthy subjects". Current Medical Research and Opinion, Informa Healthcare, GB, vol. 25. No. 8, Aug. 1, 2009, pp. 1963-1972.
Greco, Gary T. et al. "Segregation of Active Constituents from Tablet Formulations During Grinding: Theoretical Considerations" Drug Development and Industrial Pharmacy, (1982) 8(4), pp. 565-578.
Grempler, R et al. "Empagliflozin, a novel selective sodium glucose cotransporter-2 (SGLT-2) inhibitor: characterisation and comparsion with other SGLT-2 inhibitors" Diabetes, Obesity and Metabolism, (2012) vol. 14, pp. 83-90.
Guay, Andre T. "ED2: Erectile Dysfunction = Endothlial Dysfunction" (2007) Endocrinology and Metabolism Clinics of North America, V 36, 453-463.
Guillory, J. Keith "Generation of Polymorphs, Hydrates, Solvates and Amorphous Solids" Polymorphism in Pharmaceutical Solids (1999) 46 pgs.
Gupta, Rajesh et al. "Emerging Drug Candidates of Dipeptidyl Peptidase IV (DPP IV) Inhibitor Class for the Treatment of Type 2 Diabetes" (2009) Current Drug Targets, vol. 10, No. 1, 71-87.
Hach, T. et al. "The sodium glucose cotransporter-2 (SGLT-2) inhibitor empagliflozin lowers blood pressure independent of weight of HbA changes" (2012) Diabetologia, vol. 55, S 1, p. 317.
Hach, Thomas et al., "The Sodium Glucose Cotransporter-2 (SGLT-2) Inhibitor Empagliflozin Lowers Blood Pressure Independent of Weight or HbAk Changes", Poster: 770, 48th Annual Meeting of the European Association for the Study of Diabetes (EASD), Oct. 5, 2012.
Hafkamp, Frederique et al., "Optimal effectiveness of heart failure management—an umbrella review of meta-analyses examining the effectiveness of interventions to reduce (re)hospitalizations in heart failure", (2022) Heart Failure Reviews, vol. 27, 1683-1748.
Handlon, Anthony L. "Sodium glucose co-transporter 2 (SGLT2) inhibitors as potential antidiabetic agents" (2005) Expert Opinion on Therapeutic Patents, 15:11, 1531-1540.
Haneda, Masakazu et al. "The Effect of Luseogliflozin (TS-071), a Selective SGLT2 Inhibitor, on Pharmacodynamics and Pharmacokinetics in Japanese Type 2 Diabetic Subjects with Renal Impairment" (2012) Clincial Diabetes/Therapeutics Posters 1062-P, A273.
Hansch, C. "Search for New Drugs, Use of Quantitative Structure—Activity Relationships (QSAR) In Drug Design" (1980) Pomona College, Clermont, CA, Translated from Khimiko-Farmatsevticheskii Zhurnal, vol. 14, No. 10, 15-30.
Harris, Maureen I. "Classification, Diagnostic Criteria, and Screening for Diabetes" (1995) Diabetes in America, 2nd Edition, pp. 15-36.
Hasnain, Mehrul et al. "Metformin for Atypical Antipsychotic-Induced Weight Gain and Glucose Metabolism Dysregulation—Review of Literature and Clinical Suggestions" (2010) CNS Drugs, 24(3), pp. 194-206.
Hatsuda, Asanori., et al; A Practical Synthesis of Highly Functionalized Aryl Nitriles Through Cyanation of Aryl Bromides Employing Heterogeneous Pd/C; Tetrahedron Letters (2005) vol. 46 pp. 1849-1853; Elsevier Ltd.
Hausman D.S. et al., "Comparison of Low Shear, High Shear, and Fluid Bed Granulation During Low Dose Tablet Process Development" Drug Development and Industrial Pharmacy, (2004) 259-266.
Heerspink, H.J. Lambers et al. "Is Doubling of Serum Creatinine a Valid Clinical 'Hard' Endpoint in Clinical Nephrology Trials?", (2011) Nephron Clin Pract, vol. 119, c195-c199.
Heerspink, Hiddo J. Lambers et al."Estimated GFR Decline as a Surrogate End Point for Kidney Failure: A Post Hoc Analysis From the Reduction of End Points in Non-Insulin-Dependent Diabetes With the Angiotensin II Antagonist Losartan (RENAAL) Study and Irbesartan Diabetic Nephropathy Trial (IDNT)" (2014) Original Investigation Pathogenesis and Treatment of Kidney Disease, vol. 63, Issue 2, p. 244-250.
Heise, T. et al. "Safety, tolerability, pharmacokinetics and pharmacodynamics following 4 weeks' treatment with empagliflozin once daily in patients with type 2 diabetes" (2013) Diabetes, Obesity and Metabolism, 15: 613-621.
Heise, Tim et al. "BI 10773, a Sodium-Glucose Co-Transporter Inhibitor (SGLT-2), Is Safe and Efficacious Follwing 4-Week Treatment in Patients with Type 2 Diabetes" (2010) American Diabetes Association, vol. 59, 629-P.
Heise, Tim et al. "Treatment with BI 1356, a Novel and Potent DPP-IV Inhibitor Significantly Reduces Glucose Excursions after an OGTT in Patients with Type 2 Diabetes" (2007) Diabetes, Supp 1, vol. 56, 4 pgs.

(56) References Cited

OTHER PUBLICATIONS

Henderson, David C. et al. "Clozapine and Hypertension: A Chart Review of 82 Patients" (2004) J Clin Psychiatry, 65, pp. 686-689.
Henry Ford Health System, "Chronic Kidney Disease, Clinical Practice Recommendations for Primary Care Physicians and Healthcare Providers, A Collaborative Approach", (Edition 6.0), 76 pgs.
Herrington, W.G. et al., "Empagliflozin in Patients with Chronic Kidney Disease", New England Journal of Medicine, 2022, 1-11, DOI: 10.1056/NEJMoa2204233.
Hinnen, Deborah "Short commentary on empagliflozin and its potential clinical impact", Therapeutic Advances in Endocrinology and Metabolism, 2015, vol. 6, No. 2, 68-81.
Ho, Chen-Hsun et al. "The Prevalence and the Risk Factors of Testosterone Deficiency in Newly Diagnosed and Previously Known Type 2 Diabetic Men" (2015) International Society for Sexual Medicine, 12, 389-397.
Holst, Jens Juul et al. "Role of Incretin Hormones in the Regulaion of Insulin Secretion in Diabetic and Nondiabetic Humans" (2004) Am. J Physiol Endocrinol Metab, 287: E199-E206.
Home, P.D. "Impact of the UKPDS—an overview" Diabetes UK, Diabetic Medicine, (2008) 25, Supp 2, 2-8.
Hongu, Mitsuya et al. "Na+-Glucose Cotransporter Inhibitors as Antidiabetic Agents. II. Synthesis and Structure—Activity Relationships of 4'Dehydroxyphlorizin Derivatives" (1998) Chem. Pharm. Bull. 46(1), 22-33.
Hu, Gongzheng. "Zoopharmacy" China Agriculture Press, Section 4, (2008) pp. 32-33.
Hubert, Mario et al. "Oral solid dosage form—From choice of particle size technique to method development and validation" (2008) American Pharmaceutical Review, 14-23.
Hummel, Charles S. et al. "Glucose transport by human renal Na+/D-glucose co-transporters" (2010) Am J Physiol Cell Physiol, 34 pgs.
Hussar, Daniel A et al. "2015 New Drug Update" The Consultant Pharmacist, (2015) vol. 30, No. 4, 192-208.
Hussey, Elizabeth K. et al. "Safety, Pharmacokinetics and Pharmacodynamics of Remogliflozin Etabonate (SGLT2 Inhibitor) and Metformin When Co-Administered in Type 2 Diabetes Mellitus (T2DM) Patients" Diabetes, American Diabetes Association, (2009) XP00913667, vol. 58, p. A157.
Hutton, Craig A., et al; A Convenient Preparation of dityrosine via Miyaura Borylation-Suzuki Coupling of Iodotyrosine Derivatives; Tetrahedron Letters (2003) vol. 44 pp. 4895-4898; Pergamon Press.
Iacocca, Ronald G. et al. "Particle Engineering: A Strategy for Establishing Drug Substance Physical Property Specifications During Small Molecule Development" (2009) Journal of Pharmaceutical Sciences, vol. 99, No. 1, 51-75.
Idris, Iskandar et al "Sodium-glucose co-transporter-2 inhibitors: an emerging new class of oral antidiabetic drug" (2009) Diabetes, Obesity and Metabolism, 11, 79-88.
Iida, Takehiko., et al; Tributylmagnesium Ate Complex-Mediated Novel Bromine-Magnesium Exchange Reaction for Selective Monosubstitution of Dibromoarenes; Tetrahedron Letters (2001) vol. 42 pp. 4841-4844; Pergamon Press.
Insalaco, Monica et al. "Sodium Glucose Co-transporter Type 2 (SGLT2) Inhibitors in CKD" (2015) Nefrologia, vol. 32, No. 4, pp. 1-9.
Institute of International Medical Education, Glossary of medical education terms, http://www.iime.org/glossary.htm Accessed Mar. 2013 (Year: 2013).
International Search Report and Written Opinion for PCT/EP2012/062922 mailed Aug. 14, 2012.
International Search Report for PCT/EP2005/002618 mailed Jun. 30, 2005.
International Search Report for PCT/EP2005/056806 mailed Dec. 27, 2006.
International Search Report for PCT/EP2006/061520 mailed Jul. 26, 2006.
International Search Report for PCT/EP2006/061956 mailed on Jul. 5, 2006.
International Search report for PCT/EP2006/061957 mailed on Jul. 5, 2006.
International Search Report for PCT/EP2006/062191 mailed Aug. 8, 2006.
International Search Report for PCT/EP2006/064702 mailed on Jul. 26, 2007.
International Search Report for PCT/EP2006/065710 mailed Mar. 8, 2007.
International Search Report for PCT/EP2006/066107 mailed Jan. 11, 2007.
International Search Report for PCT/EP2006/066347 mailed Mar. 7, 2007.
International Search Report for PCT/EP2007/051411 mailed on May 2, 2007.
International Search Report for PCT/EP2007/054248 mailed on Jun. 18, 2007.
International Search Report for PCT/EP2007/062023 mailed Sep. 17, 2008.
International Search Report for PCT/EP2010//064117 mailed on Nov. 30, 2010.
International Search Report for PCT/EP2010/051734 mailed Jun. 8, 2010.
International Search Report for PCT/EP2010/051735 mailed May 20, 2010.
International Search Report for PCT/EP2010/051736 mailed May 7, 2010.
International Search Report for PCT/EP2010/051737 mailed May 7, 2010.
International Search Report for PCT/EP2010/064120 mailed Mar. 31, 2011.
International Search Report for PCT/EP2010/064619 mailed Jan. 20, 2011.
International Search Report for PCT/EP2011/054734 mailed Aug. 12, 2011.
International Search Report for PCT/EP2011/069532 mailed Dec. 15, 2011.
International Search Report for PCT/EP2012/052108 mailed Mar. 8, 2012.
International Search Report for PCT/EP2012/053910 mailed May 14, 2012.
International Search Report for PCT/EP2012/060194 mailed on Jul. 17, 2012.
International Search Report for PCT/EP2013/054524 mailed on May 6, 2013.
International Search Report for PCT/EP2013/055671 mailed Apr. 16, 2013.
International Search Report for PCT/EP2014/056655 filed Apr. 3, 2014.
International Search Report for PCT/EP2014/056657 filed Apr. 3, 2014.
International Search Report for PCT/EP2014/057754 filed Apr. 16, 2014.
International Search Report for PCT/EP2014/057754 mailed on May 27, 2014.
International Search Report for PCT/EP2016/074601 mailed Dec. 16, 2016.
International Search Report for PCT/EP2017/075664 mailed on Dec. 8, 2017.
International Search Report for PCT/EP2017/078577 mailed on Feb. 1, 2018.
Fox, Caroline et al., "Associations of kidney disease measures with mortality and end-stage renal disease in individuals with and without diabetes: a meta-analysis" Lancet, 2012, vol. 380, No. 9859, 1662-1673.
Heerspink et al., "Albuminuria: A Target for Treatment in Diabetic and Non-Diabetic Nephropathy", Chronic Renal Disease, 2015, Chapter 54, 663-673.
Holt, Richard I.G., ., "Textbook of Diabetes" Wiley-Blackwell, Fourth Edition, 2010, Oxford, Chapter 37, 599-614.
Komala, Muralikrishna G. et al. "Inhibition of Kidney Proximal Tubular Glucose Reabsorption Does Not Prevent against Diabetic Nephropathy in Type 1 Diabetic eNOS Knockout Mice" (2014) vol. 9, Issue 11, Plos One, e108994, 12 pgs.

(56) References Cited

OTHER PUBLICATIONS

Reddy et al., "SGLT2 inhibitors in the managements of type 2 diabetes", Endocrine, 2016, vol. 53, No. 2, 364-372.

* cited by examiner

PHARMACEUTICAL COMPOSITION, METHODS FOR TREATING AND USES THEREOF

TECHNICAL FIELD OF THE INVENTION

The present invention relates to methods for treating or preventing chronic kidney disease and cardiovascular disease in patients with chronic kidney disease.

BACKGROUND OF THE INVENTION

Chronic kidney disease (CKD), also known as chronic renal disease, is a progressive loss in renal function over a period of months or years. The symptoms of worsening kidney function are non-specific, and chronic kidney disease is often diagnosed as a result of screening of people known to be at risk of kidney problems. CKD is a highly prevalent disease, afflicting more than one out of ten individuals worldwide.

Chronic kidney disease may be identified by a blood test, for example for creatinine. Higher levels of creatinine indicate a lower glomerular filtration rate and as a result a decreased capability of the kidneys to excrete waste products.

CKD has been classified into 5 stages, where stage 1 is kidney damage with normal GFR (mL/min/1.73 m$^2$) of ≥90; stage 2 is kidney damage with a mild decrease in GFR (GFR 60-89); stage 3 is a moderate decrease in GFR (GFR 30-59); stage 4 is a severe decrease in GFR (GFR 15-29); and stage 5 is kidney failure (GFR <15 or dialysis). Stage 5 CKD is often called End Stage Renal Disease (ESRD) and is synonymous with the now outdated terms chronic kidney failure (CKF) or chronic renal failure (CRF).

Albuminuria can also be a sign of kidney disease. Albuminuria has been classified into 3 categories, where category A1 reflects no albuminuria with albumin normal to mildly increased; category A2 which reflects microalbuminuria with albumin moderately increased; category A3 which reflects macroalbuminuria with albumin severely increased.

There is no specific treatment unequivocally shown to slow the worsening of chronic kidney disease and severe CKD requires renal replacement therapy, which may involve a form of dialysis, but ideally constitutes a kidney transplant.

Since many CKD patients will die due to a cardiovascular event (CV) event before reaching ESRD, reducing CV risk is another consideration in treatment.

Therefore, there is an unmet medical need for methods, medicaments and pharmaceutical compositions able to slow the worsening or progression of chronic kidney disease and reduce the risk of CV events in patients, in particular patients with chronic kidney disease.

SUMMARY OF THE INVENTION

The present invention provides a method of treating or slowing the progression of chronic kidney disease in a patient with chronic kidney disease, the method comprising administering empagliflozin to the patient. In one aspect, the method additionally reduces the risk of cardiovascular death in the patient. In one aspect, the method additionally reduces the risk of all-cause mortality in the patient. In one aspect, the method additionally reduces the risk of all-cause hospitalization in the patient. In a further aspect, the patient has moderately or severely decreased renal function or elevated albuminuria levels, for example ≥200 mg/g.

In one aspect, the present invention also provides a method for reducing the risk of chronic kidney disease, the method comprising administering empagliflozin to the patient. In one aspect, the method additionally reduces the risk of cardiovascular death in the patient. In one aspect, the method additionally reduces the risk of all-cause mortality in the patient. In one aspect, the method additionally reduces the risk of all-cause hospitalization in the patient. In a further aspect, the patient has moderately or severely decreased renal function or elevated albuminuria levels, for example ≥200 mg/g.

In one aspect, the patient has an eGFR ≥20 to <45 mL/min/1.73 m$^2$. In one aspect, the patient has an eGFR ≥20 mL/min/1.73 m$^2$ and a urinary albumin-to-creatine ratio (UACR) ≥200 mg/g. In one aspect, the patient has an eGFR ≥45 and <90 ml/min/1.73 m$^2$ and a urinary albumin-to-creatine ratio (UACR) ≥200 mg/g.

In one aspect, the patient is treated with a RAAS inhibitor (Renin-Angiotensin-Aldosterone System). In one aspect, the patient is treated with an Angiotensin-Converting Enzyme (ACE) inhibitor and/or an angiotensin II receptor blocker (ARB).

In one aspect, the patient is on standard of care according to local/international guideline to treat CKD risk factors.

In one aspect, the patient is a non-diabetic patient. In one aspect, the patient is a patient with pre-diabetes or a patient with type 2 or type 1 diabetes mellitus.

In one aspect, the patient is a non-diabetic and non-pre-diabetic patient. In one aspect, the patient is not at risk or even high risk for cardiovascular events. In one aspect, the patient is a not a patient with chronic heart failure, in particular not a patient with HFrEF (Heart Failure with reduced Ejection Fraction) and/or HFpEF (Heart Failure with preserved Ejection Fraction).

In one aspect, empagliflozin is administered at a dose in a range from 0.5 mg to 25 mg, for example from 1 mg to 25 mg, for example at a dose of 10 mg or 25 mg. In one aspect, empagliflozin is administered once daily to the patient.

The present invention further provides for empagliflozin or a pharmaceutical composition comprising empagliflozin optionally in combination with one or more other therapeutic substances for use as a medicament in any one of the methods described herein.

The present invention further provides for empagliflozin or a pharmaceutical composition comprising empagliflozin optionally in combination with one or more other therapeutic substances for use in a method for treatment, prevention, slowing the progression or risk reduction in any one of the diseases or conditions described herein.

The present invention further provides for empagliflozin or a pharmaceutical composition comprising empagliflozin optionally in combination with one or more other therapeutic substances for use in the manufacture of a medicament for use in any one of the methods described herein.

In the methods according to the present invention empagliflozin is optionally administered in combination with one or more other therapeutic substances to the patient.

Further aspects of the present invention become apparent to the one skilled in the art by the description hereinbefore and in the following and by the examples.

Definitions

The term "active ingredient" of a pharmaceutical composition according to the present invention means the SGLT2 inhibitor empagliflozin according to the present invention. An "active ingredient" is also sometimes referred to herein as an "active substance".

The term "body mass index" or "BMI" of a human patient is defined as the weight in kilograms divided by the square of the height in meters, such that BMI has units of kg/m².

The term "overweight" is defined as the condition wherein the individual has a BMI greater than or 25 kg/m² and less than 30 kg/m². The terms "overweight" and "pre-obese" are used interchangeably.

The terms "obesity" or "being obese" and the like are defined as the condition wherein the individual has a BMI equal to or greater than 30 kg/m². According to a WHO definition the term obesity may be categorized as follows: the term "class I obesity" is the condition wherein the BMI is equal to or greater than 30 kg/m² but lower than 35 kg/m²; the term "class II obesity" is the condition wherein the BMI is equal to or greater than 35 kg/m² but lower than 40 kg/m²; the term "class III obesity" is the condition wherein the BMI is equal to or greater than 40 kg/m².

The indication obesity includes in particular exogenic obesity, hyperinsulinaemic obesity, hyperplasmic obesity, hyperphyseal adiposity, hypoplasmic obesity, hypothyroid obesity, hypothalamic obesity, symptomatic obesity, infantile obesity, upper body obesity, alimentary obesity, hypogonadal obesity, central obesity, visceral obesity, abdominal obesity.

The term "visceral obesity" is defined as the condition wherein a waist-to-hip ratio of greater than or equal to 1.0 in men and 0.8 in women is measured. It defines the risk for insulin resistance and the development of pre-diabetes.

The term "abdominal obesity" is usually defined as the condition wherein the waist circumference is >40 inches or 102 cm in men, and is >35 inches or 94 cm in women. With regard to a Japanese ethnicity or Japanese patients abdominal obesity may be defined as waist circumference ≥85 cm in men and ≥90 cm in women (see e.g. investigating committee for the diagnosis of metabolic syndrome in Japan).

The term "euglycemia" is defined as the condition in which a subject has a fasting blood glucose concentration within the normal range, greater than 70 mg/dL (3.89 mmol/L) and less than 100 mg/dL (5.6 mmol/L). The word "fasting" has the usual meaning as a medical term.

The term "hyperglycemia" is defined as the condition in which a subject has a fasting blood glucose concentration above the normal range, greater than 100 mg/dL (5.6 mmol/L). The word "fasting" has the usual meaning as a medical term.

The term "hypoglycemia" is defined as the condition in which a subject has a blood glucose concentration below the normal range, in particular below 70 mg/dL (3.89 mmol/L).

The term "postprandial hyperglycemia" is defined as the condition in which a subject has a 2 hour postprandial blood glucose or serum glucose concentration greater than 200 mg/dL (11.11 mmol/L).

The term "impaired fasting blood glucose" or "IFG" is defined as the condition in which a subject has a fasting blood glucose concentration or fasting serum glucose concentration in a range from 100 to 125 mg/dl (i.e. from 5.6 to 6.9 mmol/l), in particular greater than 110 mg/dL and less than 126 mg/dl (7.00 mmol/L). A subject with "normal fasting glucose" has a fasting glucose concentration smaller than 100 mg/dl, i.e. smaller than 5.6 mmol/l.

The term "impaired glucose tolerance" or "IGT" is defined as the condition in which a subject has a 2 hour postprandial blood glucose or serum glucose concentration greater than 140 mg/dl (7.78 mmol/L) and less than 200 mg/dL (11.11 mmol/L). The abnormal glucose tolerance, i.e. the 2 hour postprandial blood glucose or serum glucose concentration can be measured as the blood sugar level in mg of glucose per dL of plasma 2 hours after taking 75 g of glucose after a fast. A subject with "normal glucose tolerance" has a 2 hour postprandial blood glucose or serum glucose concentration smaller than 140 mg/dl (7.78 mmol/L).

The term "hyperinsulinemia" is defined as the condition in which a subject with insulin resistance, with or without euglycemia, has fasting or postprandial serum or plasma insulin concentration elevated above that of normal, lean individuals without insulin resistance, having a waist-to-hip ratio <1.0 (for men) or <0.8 (for women).

The terms "insulin-sensitizing", "insulin resistance-improving" or "insulin resistance-lowering" are synonymous and used interchangeably.

The term "insulin resistance" is defined as a state in which circulating insulin levels in excess of the normal response to a glucose load are required to maintain the euglycemic state (Ford E S, et al. *JAMA*. (2002) 287:356-9). A method of determining insulin resistance is the euglycaemic-hyperinsulinaemic clamp test. The ratio of insulin to glucose is determined within the scope of a combined insulin-glucose infusion technique. There is found to be insulin resistance if the glucose absorption is below the 25th percentile of the background population investigated (WHO definition). Rather less laborious than the clamp test are so called minimal models in which, during an intravenous glucose tolerance test, the insulin and glucose concentrations in the blood are measured at fixed time intervals and from these the insulin resistance is calculated. With this method, it is not possible to distinguish between hepatic and peripheral insulin resistance.

Furthermore, insulin resistance, the response of a patient with insulin resistance to therapy, insulin sensitivity and hyperinsulinemia may be quantified by assessing the "homeostasis model assessment to insulin resistance (HOMA-IR)" score, a reliable indicator of insulin resistance (Katsuki A, et al. Diabetes Care 2001; 24: 362-5). Further reference is made to methods for the determination of the HOMA-index for insulin sensitivity (Matthews et al., *Diabetologia* 1985, 28: 412-19), of the ratio of intact proinsulin to insulin (Forst et al., *Diabetes* 2003, 52(Suppl.1): A459) and to an euglycemic clamp study. In addition, plasma adiponectin levels can be monitored as a potential surrogate of insulin sensitivity. The estimate of insulin resistance by the homeostasis assessment model (HOMA)-IR score is calculated with the formula (Galvin P, et al. Diabet Med 1992; 9:921-8):

$$\text{HOMA-IR} = [\text{fasting serum insulin } (\rho U/mL)] \times [\text{fasting plasma glucose(mmol/L)/22.5}]$$

Insulin resistance can be confirmed in these individuals by calculating the HOMA-IR score. For the purpose of this invention, insulin resistance is defined as the clinical condition in which an individual has a HOMA-IR score >4.0 or a HOMA-IR score above the upper limit of normal as defined for the laboratory performing the glucose and insulin assays.

As a rule, other parameters are used in everyday clinical practice to assess insulin resistance. Preferably, the patient's triglyceride concentration is used, for example, as increased triglyceride levels correlate significantly with the presence of insulin resistance.

Individuals likely to have insulin resistance are those who have two or more of the following attributes: 1) overweight or obese, 2) high blood pressure, 3) hyperlipidemia, 4) one or more 1$^{st}$ degree relative with a diagnosis of IGT or IFG or type 2 diabetes.

Patients with a predisposition for the development of IGT or IFG or type 2 diabetes are those having euglycemia with hyperinsulinemia and are by definition, insulin resistant. A typical patient with insulin resistance is usually overweight or obese. If insulin resistance can be detected, this is a particularly strong indication of the presence of pre-diabetes. Thus, it may be that in order to maintain glucose homoeostasis a person needs 2-3 times as much insulin as a healthy person, without this resulting in any clinical symptoms.

"Pre-diabetes" is a general term that refers to an intermediate stage between normal glucose tolerance (NGT) and overt type 2 diabetes mellitus (T2DM), also referred to as intermediate hyperglycaemia. Therefore in one aspect of the present invention "pre-diabetes" is diagnosed in an individual if HbA1c is more or equal to 5.7% and less than 6.5%. According to another aspect of this invention "pre-diabetes" represents 3 groups of individuals, those with impaired glucose tolerance (IGT) alone, those with impaired fasting glucose (IFG) alone or those with both IGT and IFG. IGT and IFG usually have distinct pathophysiologic etiologies, however also a mixed condition with features of both can exist in patients. Therefore in another aspect of the present invention a patient being diagnosed of having "pre-diabetes" is an individual with diagnosed IGT or diagnosed IFG or diagnosed with both IGT and IFG. Following the definition according to the American Diabetes Association (ADA) and in the context an aspect of the present invention a patient being diagnosed of having "pre-diabetes" is an individual with:

a) a fasting plasma glucose (FPG) concentration <100 mg/dL [1 mg/dL=0.05555 mmol/L] and a 2-hour plasma glucose (PG) concentration, measured by a 75-g oral glucose tolerance test (OGTT), ranging between ≥140 mg/dL and <200 mg/dL (i.e., IGT); or b) a fasting plasma glucose (FPG) concentration between ≥100 mg/dL and <126 mg/dL and a 2-hour plasma glucose (PG) concentration, measured by a 75-g oral glucose tolerance test (OGTT) of <140 mg/dL (i.e., IFG); or c) a fasting plasma glucose (FPG) concentration between ≥100 mg/dL and <126 mg/dL and a 2-hour plasma glucose (PG) concentration, measured by a 75-g oral glucose tolerance test (OGTT), ranging between ≥140 mg/dL and <200 mg/dL (i.e., both IGT and IFG).

Patients with "pre-diabetes" are individuals being predisposed to the development of type 2 diabetes. Pre-diabetes extends the definition of IGT to include individuals with a fasting blood glucose within the high normal range ≥100 mg/dL (J. B. Meigs, et al. *Diabetes* 2003; 52:1475-1484). The scientific and medical basis for identifying pre-diabetes as a serious health threat is laid out in a Position Statement entitled "The Prevention or Delay of Type 2 Diabetes" issued jointly by the American Diabetes Association and the National Institute of Diabetes and Digestive and Kidney Diseases (Diabetes Care 2002; 25:742-749).

The methods to investigate the function of pancreatic beta-cells are similar to the above methods with regard to insulin sensitivity, hyperinsulinemia or insulin resistance: An improvement of beta-cell function can be measured for example by determining a HOMA-index (homeostasis model assessment) for beta-cell function, HOMA-B, (Matthews et al., *Diabetologia* 1985, 28: 412-19), the ratio of intact proinsulin to insulin (Forst et al., *Diabetes* 2003, 52(Suppl.1): A459), first and second phase insulin secretion after an oral glucose tolerance test or a meal tolerance test (Stumvoll et al., Diabetes care 2000, 23: 295-301), the insulin/C-peptide secretion after an oral glucose tolerance test or a meal tolerance test, or by employing a hyperglycemic clamp study and/or minimal modeling after a frequently sampled intravenous glucose tolerance test (Stumvoll et al., *Eur J Clin Invest* 2001, 31: 380-81).

The term "type 1 diabetes" is defined as the condition in which a subject has, in the presence of autoimmunity towards the pancreatic beta-cell or insulin, a fasting blood glucose or serum glucose concentration greater than 125 mg/dL (6.94 mmol/L). If a glucose tolerance test is carried out, the blood sugar level of a diabetic will be in excess of 200 mg of glucose per dL (11.1 mmol/l) of plasma 2 hours after 75 g of glucose have been taken on an empty stomach, in the presence of autoimmunity towards the pancreatic beta cell or insulin. In a glucose tolerance test 75 g of glucose are administered orally to the patient being tested after 10-12 hours of fasting and the blood sugar level is recorded immediately before taking the glucose and 1 and 2 hours after taking it. The presence of autoimmunity towards the pancreatic beta-cell may be observed by detection of circulating islet cell autoantibodies ["type 1A diabetes mellitus"], i.e., at least one of: GAD65 [glutamic acid decarboxylase-65], ICA [islet-cell cytoplasm], IA-2 [intracytoplasmatic domain of the tyrosine phosphatase-like protein IA-2], ZnT8 [zinc-transporter-8] or anti-insulin; other signs of autoimmunity without the presence of typical circulating autoantibodies [type 1B diabetes], i.e. as detected through pancreatic biopsy or imaging). Typically a genetic predisposition is present (e.g. HLA, INS VNTR and PTPN22), but this is not always the case.

The term "type 2 diabetes mellitus" or "T2DM" is defined as the condition in which a subject has a fasting blood glucose or serum glucose concentration greater than 125 mg/dL (6.94 mmol/L). The measurement of blood glucose values is a standard procedure in routine medical analysis. If a glucose tolerance test is carried out, the blood sugar level of a diabetic will be in excess of 200 mg of glucose per dL (11.1 mmol/l) of plasma 2 hours after 75 g of glucose have been taken on an empty stomach. In a glucose tolerance test 75 g of glucose are administered orally to the patient being tested after 10-12 hours of fasting and the blood sugar level is recorded immediately before taking the glucose and 1 and 2 hours after taking it. In a healthy subject, the blood sugar level before taking the glucose will be between 60 and 110 mg per dL of plasma, less than 200 mg per dL 1 hour after taking the glucose and less than 140 mg per dL after 2 hours. If after 2 hours the value is between 140 and 200 mg, this is regarded as abnormal glucose tolerance.

The term "late stage type 2 diabetes mellitus" includes patients with a secondary drug failure, indication for insulin therapy and progression to micro- and macrovascular complications e.g. diabetic nephropathy, or coronary heart disease (CHD).

The term "LADA" ("latent autoimmune diabetes of adults") refers to patients that have a clinical diagnosis of type 2 diabetes, but who are being detected to have autoimmunity towards the pancreatic beta cell. Latent autoimmune diabetes of adults (LADA) is also known as slowly progressive type 1 diabetes mellitus (T1DM), "mild" T1DM, non-insulin dependent type 1 DM, type 1½ DM, double diabetes or antibody positive type 2 DM (T2DM). LADA is often not clearly defined and, opposed to T1DM, seldom or never presents with significant weight loss and ketoacidosis due to rapidly progressive β-cell failure.

The term "HbA1c" refers to the product of a non-enzymatic glycation of the haemoglobin B chain. Its determination is well known to one skilled in the art. In monitoring the treatment of diabetes mellitus the HbA1c value is of exceptional importance. As its production depends essentially on the blood sugar level and the life of the erythrocytes, the HbA1c in the sense of a "blood sugar memory" reflects the average blood sugar levels of the preceding 4-6 weeks. Diabetic patients whose HbA1c value is consistently well adjusted by intensive diabetes treatment (i.e. <6.5% of the total haemoglobin in the sample), are significantly better protected against diabetic microangiopathy. For example, metformin on its own achieves an average improvement in the HbA1c value in the diabetic of the order of 1.0-1.5%. This reduction of the HbA1C value is not sufficient in all diabetics to achieve the desired target range of <7% or <6.5% and preferably <6% HbA1c.

The term "insufficient glycemic control" or "inadequate glycemic control" in the scope of the present invention means a condition wherein patients show HbA1c values above 6.5%, in particular above 7.0%, even more preferably above 7.5%, especially above 8%.

The "metabolic syndrome", also called "syndrome X" (when used in the context of a metabolic disorder), also called the "dysmetabolic syndrome" is a syndrome complex with the cardinal feature being insulin resistance (Laaksonen D E, et al. *Am J Epidemiol* 2002; 156:1070-7). According to the ATP III/NCEP guidelines (Executive Summary of the Third Report of the National Cholesterol Education Program (NCEP) Expert Panel on Detection, Evaluation, and Treatment of High Blood Cholesterol in Adults (Adult Treatment Panel III) *JAMA: Journal of the American Medical Association* (2001) 285:2486-2497), diagnosis of the metabolic syndrome is made when three or more of the following risk factors are present:

1. Abdominal obesity, defined as waist circumference >40 inches or 102 cm in men, and >35 inches or 94 cm in women; or with regard to a Japanese ethnicity or Japanese patients defined as waist circumference ≥85 cm in men and ≥90 cm in women;
2. Triglycerides: ≥150 mg/dL
3. HDL-cholesterol <40 mg/dL in men
4. Blood pressure ≥130/85 mm Hg (SBP≥130 or DBP≥85)
5. Fasting blood glucose ≥100 mg/dL The NCEP definitions have been validated (Laaksonen D E, et al. *Am J Epidemiol*. (2002) 156:1070-7). Triglycerides and HDL cholesterol in the blood can also be determined by standard methods in medical analysis and are described for example in Thomas L (Editor): "Labor and Diagnose", TH-Books Verlagsgesellschaft mbH, Frankfurt/Main, 2000.

According to a commonly used definition, hypertension is diagnosed if the systolic blood pressure (SBP) exceeds a value of 140 mm Hg and diastolic blood pressure (DBP) exceeds a value of 90 mm Hg. If a patient is suffering from manifest diabetes it is currently recommended that the systolic blood pressure be reduced to a level below 130 mm Hg and the diastolic blood pressure be lowered to below 80 mm Hg.

The term "empagliflozin" refers to the SGLT2 inhibitor 1-chloro-4-(β-D-glucopyranos-1-yl)-2-[4-((S)-tetrahydrofuran-3-yloxy)-benzyl]-benzene of the formula

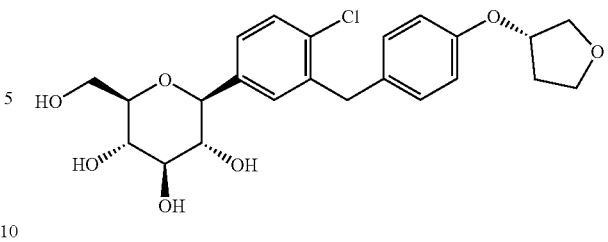

as described for example in WO 2005/092877. Methods of synthesis are described in the literature, for example WO 06/120208 and WO 2011/039108. According to this invention, it is to be understood that the definition of empagliflozin also comprises its hydrates, solvates and polymorphic forms thereof, and prodrugs thereof. An advantageous crystalline form of empagliflozin is described in WO 2006/117359 and WO 2011/039107 which hereby are incorporated herein in their entirety. This crystalline form possesses good solubility properties which enables a good bioavailability of the SGLT2 inhibitor. Furthermore, the crystalline form is physico-chemically stable and thus provides a good shelf-life stability of the pharmaceutical composition. Preferred pharmaceutical compositions, such as solid formulations for oral administration, for example tablets, are described in WO 2010/092126, which hereby is incorporated herein in its entirety.

The terms "treatment" and "treating" comprise therapeutic treatment of patients having already developed said condition, in particular in manifest form. Therapeutic treatment may be symptomatic treatment in order to relieve the symptoms of the specific indication or causal treatment in order to reverse or partially reverse the conditions of the indication or to stop or slow down progression of the disease. Thus the compositions and methods of the present invention may be used for instance as therapeutic treatment over a period of time as well as for chronic therapy.

The terms "prophylactically treating", "preventively treating" and "preventing" are used interchangeably and comprise a treatment of patients at risk to develop a condition mentioned hereinbefore, thus reducing said risk.

The term "tablet" comprises tablets without a coating and tablets with one or more coatings. Furthermore the "term" tablet comprises tablets having one, two, three or even more layers and press-coated tablets, wherein each of the before mentioned types of tablets may be without or with one or more coatings. The term "tablet" also comprises mini, melt, chewable, effervescent and orally disintegrating tablets.

The terms "pharmacopoe" and "pharmacopoeias" refer to standard pharmacopoeias such as the "USP 31-NF 26 through Second Supplement" (United States Pharmacopeial Convention) or the "European Pharmacopoeia 6.3" (European Directorate for the Quality of Medicines and Health Care, 2000-2009).

The term "chronic kidney disease (CDK)" is defined as abnormalities of kidney structure or function, present for more than three months, with implications for health. CKD is classified based on cause, GFR category, and albuminuria category (CGA).

CKD has been classified into 5 stages, where stage 1 is kidney damage with normal GFR (mL/min/1.73 m2) of 90 or above; stage 2 is kidney damage with a mild decrease in GFR (GFR 60-89); stage 3 is a moderate decrease in GFR (GFR 30-59); stage 4 is a severe decrease in GFR (GFR 15-29); and stage 5 is kidney failure (GFR <15 or dialysis). Stage 3 has been subdivided into stage 3A, which is a mild to moderate decrease in GFR (GFR 45-59), and stage 3B, which is a moderate to severe decrease in GFR (GFR 30-44).

The term "albuminuria" is defined as a condition wherein more than the normal amount of albumin is present in the urine. Albuminuria can be determined by the albumin excretion rate (AER) and/or the albumin-to-creatine ratio (ACR) in the urine (also referred to as UACR). Albuminuria categories in CKD are defined as follows:

| Category | AER (mg/ 24 hours) | ACR (approximate equivalent) | | Terms |
|---|---|---|---|---|
| | | (mg/mmol) | (mg/g) | |
| A1 | <30 | <3 | <30 | Normal to mildly increased |
| A2 | 30-300 | 3-30 | 30-300 | Moderately increased |
| A3 | >300 | >30 | >300 | Severely increased |

Category A1 reflects no albuminuria, category A2 reflects microalbuminuria, category A3 reflects macroalbuminuria. The progression of category A1 usually leads to microalbuminuria (A2) but may also directly result in macroalbuminuria (A3). Progression of microalbuminuria (A2) results in macroalbuminuria (A3).

The term "eGFR" refers to the estimated glomerular filtration rate (GFR). The GFR describes the flow rate of filtered fluid through the kidney. The estimated GFR may be calculated based on serum creatinine values e.g. using the Chronic Kidney Disease Epidemiology Collaboration (CKD-EPI) equation (also abbreviated as (CKD-EPI)cr), the Cockcroft-Gault formula or the Modification of Diet in Renal Disease (MDRD) formula, which are all known in the art.

According to an aspect of this invention the estimated glomerular filtration rate (eGFR) is derived from serum creatinine values, age sex and race based on the CKD-EPI equation:

$$GFR = 141 \times \min(S_{cr}/\kappa, 1)^{\alpha} \times \max(S_{cr}/\kappa, 1)^{-1.209} \times 0.993^{Age} \times 1.018[\text{if female}] \times 1.159[\text{if black}]$$

where:
Scr is serum creatinine in mg/dL,
κ is 0.7 for females and 0.9 for males,
α is −0.329 for females and −0.411 for males,
min indicates the minimum of $S_{cr}/\kappa$ or 1, and
max indicates the maximum of $S_{cr}/\kappa$ or 1.

For the purpose of the present invention, the degree of renal impairment in a patient is defined by the following estimated glomerular filtration rate (eGFR):

Normal renal function (CKD stage 1): eGFR ≥90 mL/min/1.73 m²
Mild renal impairment (CKD stage 2): eGFR ≥60 to <90 mL/min/1.73 m²
Moderate renal impairment (CKD stage 3): eGFR ≥30 to <60 mL/min/1.73 m²
Severe renal impairment (CKD stage 4): eGFR ≥15 to <30 mL/min/1.73 m²
Kidney failure (CKD stage 5): eGFR <15 mL/min/1.73 m²

According to the present invention moderate renal impairment can be further divided into two sub-stages:
Moderate A renal impairment (CKD 3A): eGFR ≥45 to <60 mL/min/1.73 m²
Moderate B renal impairment (CKD 3B): eGFR ≥30 to <45 mL/min/1.73 m²

DETAILED DESCRIPTION OF THE INVENTION

Beyond an improvement of glycemic control and weight loss due to an increase in urinary glucose excretion, empagliflozin shows a diuretic effect, reduced arterial stiffness and direct vascular effects (Cherney et al., *Cardiovasc Diabetol*. 2014; 13:28; Cherney et al., Circulation. 2014; 129:587-597). In the EMPA-REG OUTCOME™ study it was demonstrated that empagliflozin reduced the risk of cardiovascular death, hospitalization for heart failure and overall mortality in patients with type 2 diabetes mellitus and high cardiovascular risk (Zinman et al., *N Engl J Med*. 2015; 373:2117-2128). It was observed that treatment with empagliflozin leads to blood pressure reductions without clinically relevant changes of the heart rate, thus improving rate pressure product (RPP), a surrogate marker of cardiac oxygen demand. Furthermore empagliflozin was found of not being associated with clinically relevant reflex-mediated sympathetic activation in contrast to increases observed with diuretics. It may be assumed that altered glucose and sodium gradients within the kidney may generate a sympathoinhibitory afferent renal nerve signal. The lack of sympathetic activation may contribute to a beneficial cardiovascular and renal profile of empagliflozin (cardiorenal axis). Based on clinical and non-clinical studies including mechanistic considerations, such as the effect of empagliflozin on human autonomic cardiovascular regulation, the use of empagliflozin in the treatment, prevention or slowing the progression of certain diseases and conditions or reducing the risk thereof, in particular chronic kidney disease and cardiovascular death in certain patients, is described hereinbefore and hereinafter.

According to one embodiment, this invention provides a method of treating, reducing the risk of or slowing the progression of chronic kidney disease in a patient with chronic kidney disease, said method comprising administering empagliflozin to the patient.

According to one embodiment, this invention provides a method for treating, preventing, protecting against, reducing the risk of, delaying the occurrence of and/or delaying the progression of chronic kidney disease in a patient not diagnosed with chronic heart failure comprising administering empagliflozin to the patient wherein the patient is a non-diabetic patient. In particular this embodiment relates to a method for treating and/or delaying the progression of chronic kidney disease in the patient. According to an aspect of this embodiment the patient is a patient with stage 3, including stage 3a and/or 3b, chronic kidney disease. According to another aspect of this embodiment the patient is a patient with stage 4 chronic kidney disease.

Chronic kidney disease (CKD), also known as chronic renal disease, is a progressive loss in renal function over a period of months or years. Patients with renal disease, renal dysfunction or renal impairment may include patients with chronic renal insufficiency or impairment, which can be stratified (if not otherwise noted) according to glomerular filtration rate (GFR, ml/min/1.73 m²) into 5 disease stages: stage 1 characterized by normal GFR 90 plus either persistent albuminuria (e.g. UACR mg/g) or known structural or hereditary renal disease; stage 2 characterized by mild reduction of GFR (GFR 60-89) describing mild renal impairment; stage 3 characterized by moderate reduction of GFR (GFR 30-59) describing moderate renal impairment; stage 4 characterized by severe reduction of GFR (GFR 15-29) describing severe renal impairment; and terminal stage 5 characterized by requiring dialysis or GFR <15 describing established kidney failure (end-stage renal disease, ESRD).

Chronic kidney disease and its stages (CKD 1-5) can be usually characterized or classified accordingly, such as based on the presence of either kidney damage (albuminuria) or impaired estimated glomerular filtration rate (GFR <60 [ml/min/1.73 m$^2$], with or without kidney damage).

Generally, mild renal impairment according to the present invention corresponds to stage 2 chronic kidney disease, moderate renal impairment according to the present invention generally corresponds to stage 3 chronic kidney disease, and severe renal impairment according to the present invention generally corresponds to stage 4 chronic kidney disease. Likewise, moderate A renal impairment according to the present invention generally corresponds to stage 3A chronic kidney disease and moderate B renal impairment according to the present invention generally corresponds to stage 3B chronic kidney disease.

According to an embodiment, this invention provides a method for reducing the risk of cardiovascular death in a patient with chronic kidney disease.

According to an embodiment, this invention provides a method for reducing the risk of all-cause mortality in a patient with chronic kidney disease.

According to an embodiment, this invention provides a method for reducing the risk of hospitalization in a patient with chronic kidney disease.

According to an embodiment, this invention provides a method for reducing the risk of heart failure hospitalization in a patient with chronic kidney disease.

According to an embodiment, this invention provides a method for reducing the risk of all cause hospitalization in a patient with chronic kidney disease.

According to an embodiment this invention provides a method for reducing the risk of any of cardiovascular death (including fatal stroke, fatal myocardial infarction and sudden death), non-fatal myocardial infarction (excluding silent myocardial infarction), non-fatal stroke (the so-called 3-point MACE) in a patient with chronic kidney disease.

In another embodiment, the present invention provides a method of preventing, reducing the risk of or delaying the occurrence of a cardiovascular event, said method comprising administering empagliflozin, optionally in combination with one or more other therapeutic substances, to the CKD patient. In one embodiment, the cardiovascular event is selected from cardiovascular death, non-fatal myocardial infarction, non-fatal stroke, hospitalisation for unstable angina pectoris and heart failure requiring hospitalisation. In one embodiment, the cardiovascular death is due to fatal myocardial infarction or fatal stroke. In one embodiment, the cardiovascular death is due to sudden death or heart failure death.

In one embodiment, the present invention provides a method of treating, reducing the risk of or slowing the progression of chronic kidney disease and reducing the risk of cardiovascular death in a patient with chronic kidney disease, the method comprising administering empagliflozin to the patient. In one aspect the patient has moderately or severely decreased renal function or elevated albuminuria levels, for example 200 mg/g.

In one aspect, the patient has an eGFR ≥20 to <45 mL/min/1.73 m$^2$. In one aspect, the patient has an eGFR ≥20 mL/min/1.73 m$^2$ and a urinary albumin-to-creatine ratio (UACR) ≥200 mg/g. In one aspect, the patient has an eGFR ≥45 and <90 ml/min/1.73 m$^2$ and a urinary albumin-to-creatine ratio (UACR) ≥200 mg/g.

In one aspect, the patient is treated with a RAAS inhibitor (Renin-Angiotensin-Aldosterone System). In one aspect, the patient is treated with an Angiotensin-Converting Enzyme (ACE) inhibitor and/or an angiotensin II receptor blocker (ARB). In one aspect, the patient is on standard of care according to local/international guideline to treat CKD risk factors.

In one aspect, the patient is a non-diabetic patient. In one aspect, the patient is a patient with pre-diabetes or a patient with type 2 or type 1 diabetes mellitus.

In one aspect, the patient is a non-diabetic and non-prediabetic patient. In one aspect, the patient is not at risk or even high risk for cardiovascular events. In one aspect, the patient is a not a patient with chronic heart failure, in particular not a patient with HFrEF (Heart Failure with reduced Ejection Fraction) and/or HFpEF (Heart Failure with preserved Ejection Fraction).

In one aspect, empagliflozin is administered at a dose in a range from 1 mg to 25 mg, for example at a dose of 10 mg or 25 mg. In one aspect, empagliflozin is administered once daily to the patient.

In one aspect, empagliflozin slows or delays the time to the first occurrence of any of the following components:
CV death
sustained decrease of 40% or more in eGFR, e.g. via (CKD-EPI)cr
incidence of ESRD defined by either
  continuous renal replacement therapy (dialysis or renal transplantation) or
  sustained eGFR <15 ml/min/1.73 m$^2$ for patients with baseline eGFR ≥30 ml/min/1.73 m$^2$ or eGFR <10 ml/min/1.73 m$^2$ for patients with baseline eGFR <30 ml/min/1.73 m$^2$ In one aspect, empagliflozin slows or delays the time to the first occurrence of renal disease progression as defined by one or more of the following:
sustained decrease of 40% or more in eGFR, e.g. via (CKD-EPI)cr
sustained eGFR <10 ml/min/1.73 m$^2$
Incidence of ESRD defined by continuous renal replacement therapy (by either dialysis or renal transplantation) or
renal death In one aspect, empagliflozin slows or delays the time to the first occurrence of any of the following components:
Occurrence of
All-cause mortality or all-cause hospitalization
All-cause hospitalization
All-cause mortality
eGFR (e.g. via (CKD-EPI)cr) slope of change from baseline
Cardiovascular death or hospitalization for heart failure In one aspect, empagliflozin slows or delays the time to any one of the following components:
Time to CV death confirmed by adjudication
Time to first occurrence of sustained decrease of 40% or more in eGFR confirmed by adjudication
Time to first incidence of ESRD confirmed by adjudication
Time to first hospitalization for congestive heart failure confirmed by adjudication
Time to first all-cause hospitalization
Time to all-cause mortality
Time to first 3-MACE (i.e. CV death, non-fatal MI, non-fatal stroke) confirmed by adjudication Time to first occurrence of all-cause mortality, sustained decrease of 40% or more in eGFR or incidence of ESRD confirmed by adjudication Time to first occurrence of all-cause mortality, sustained decrease of 50% or more in eGFR or incidence of ESRD confirmed by adjudication Time to first occurrence of all-cause mortality, sustained decrease of 57% or more in eGFR or incidence of ESRD confirmed by adjudication Time to first occurrence of composite renal endpoint (sustained decrease of 40% or more in eGFR, incidence of ESRD) confirmed by adjudication Time to first occurrence of composite renal endpoint 2 (sustained decrease of 50% or more in eGFR, incidence of ESRD) confirmed by adjudication Time to first occurrence of composite renal endpoint 3 (sustained decrease of 57% or more in eGFR, incidence of ESRD) confirmed by adjudication Time to first sustained decrease of 57% or more in eGFR confirmed by adjudication Time to first sustained decrease of 50% or more in eGFR confirmed by adjudication Time to first sustained decrease of 30% or more in eGFR confirmed by adjudication Time to first incidence of acute renal failure (incl. AKI) confirmed by adjudication Time to first incidence of AKI confirmed by adjudication Time to onset of DM (defined as HbA1c ≥6.5% or as diagnosed by the Investigator) in patients without DM defined as no history of DM and HbA1c <6.5% at baseline In the methods according to the present invention empagliflozin is optionally administered in combination with one or more other therapeutic substances to the patient.

According to an embodiment of the methods as described hereinbefore and hereinafter the patient is a non-diabetic patient, a patient with pre-diabetes, a patient with type 2 diabetes mellitus or a patient with type 1 diabetes mellitus.

According to another embodiment of the methods as described hereinbefore and hereinafter the patient is a patient with pre-diabetes. According to an aspect of this embodiment the patient has a HbA1c more or equal to 5.7% and less than 6.5%.

According to another embodiment of the methods as described hereinbefore and hereinafter the patient is a patient with pre-diabetes or a non-diabetic patient. According to an aspect of this embodiment the patient has a HbA1c less than 6.5%.

According to another embodiment of the methods as described hereinbefore and hereinafter the patient is a non-diabetic patient, in particular a non-diabetic and non-pre-diabetic patient. According to an aspect of this embodiment the patient has a HbA1c less than 5.7%.

According to another aspect the non-diabetic patient does not show an impaired glucose tolerance (IGT), i.e. the patient shows a normal glucose tolerance. For example the 2 hour postprandial blood glucose or plasma glucose (PG) concentration is smaller than 140 mg/dl (7.78 mmol/L).

According to another aspect the non-diabetic patient does not show an impaired fasting blood glucose (IFG), i.e. the patient shows a normal fasting glucose. For example the fasting plasma glucose concentration (FPG) is smaller than 100 mg/dl, i.e. smaller than 5.6 mmol/l.

In particular the non-diabetic patient does not show an impaired fasting blood glucose (IFG) and does not show an impaired glucose tolerance (IGT), i.e. the patient shows a normal glucose tolerance and a normal glucose tolerance. For example the fasting plasma glucose concentration (FPG) is smaller than 100 mg/dl, i.e. smaller than 5.6 mmol/l, and the 2 hour postprandial blood glucose or plasma glucose (PG) concentration is smaller than 140 mg/dl (7.78 mmol/L).

According to an embodiment of the methods as described hereinbefore and hereinafter empagliflozin is administered at a dose in a range from 0.5 to 25 mg per day, for example 1 to 25 mg per day, for example at a dose of 1 mg, 2.5 mg, 5 mg, 7.5 mg, 10 mg or 25 mg per day to the patient. The administration of empagliflozin may occur one or two times a day, most preferably once a day. For example a dose for once daily administration is 10 mg or 25 mg. The preferred route of administration is oral administration.

According to a particular aspect of the present invention empagliflozin is administered at a dose of 10 mg per day to the patient.

According to another particular aspect of the present invention empagliflozin is administered at a dose of 25 mg per day to the patient.

Preferably empagliflozin is administered orally to the patient once daily.

In one embodiment, patients within the meaning of this invention may include patients with chronic heart failure who have not previously been treated with a drug to treat chronic heart failure (heart-failure-drug-naïve patients). Thus, in an embodiment, the therapies described herein may be used in heart-failure-drug-naïve patients.

In another embodiment, patients within the meaning of this invention may include patients with chronic heart failure and with pre-diabetes or with type 2 diabetes mellitus (T2DM) who have not previously been treated with an antidiabetic drug (T2DM-drug-naïve patients). Thus, in an embodiment, the therapies described herein may be used in T2DM-drug-naïve patients.

Furthermore, the methods according to this invention are particularly suitable in the treatment of patients with chronic heart failure and with insulin dependency, i.e. in patients who are treated or otherwise would be treated or need treatment with an insulin or a derivative of insulin or a substitute of insulin or a formulation comprising an insulin or a derivative or substitute thereof. These patients include patients with diabetes type 2 and patients with diabetes type 1.

Furthermore, it can be found that the administration of a pharmaceutical composition according to this invention results in no risk or in a low risk of hypoglycemia. Therefore, a treatment or prophylaxis according to this invention is also advantageously possible in those patients showing or having an increased risk for hypoglycemia.

By the administration of empagliflozin excessive blood glucose is excreted through the urine of the patient based on the SGLT2 inhibiting activity, so that no gain in weight or even a reduction in body weight of the patient may result. Therefore, the methods according to this invention are advantageously suitable in those patients with chronic heart failure who are diagnosed of one or more of the conditions selected from the group consisting of overweight and obesity, in particular class I obesity, class II obesity, class III obesity, visceral obesity and abdominal obesity. In addition a method according to this invention is advantageously suitable in those patients in which a weight increase is contraindicated.

When this invention refers to patients requiring treatment or prevention, it relates primarily to treatment and prevention in humans, but the pharmaceutical composition may also be used accordingly in veterinary medicine in mammals. In the scope of this invention adult patients are preferably humans of the age of 18 years or older. Also in the scope of this invention, patients are adolescent humans, i.e. humans of age 6 to 17 years, for example 10 to 17 years, preferably of age 13 to 17 years.

According to an embodiment of the present invention empagliflozin is administered in combination with one or more other therapeutic substances to the patient. The combined administration may be simultaneously, separately or sequentially.

In one embodiment, the active substances that are indicated in the treatment of chronic heart failure are selected from angiotensin receptor blockers (ARB), angiotensin-converting enzyme (ACE) inhibitors, angiotensin receptor neprilysin inhibitors (ARNi), beta-blockers, aldosterone antagonists (MRA), digoxin, ivabradine and diuretics.

In one embodiment, the antidiabetic substances are selected from metformin, sulphonylureas, nateglinide, repaglinide, PPAR-gamma agonists, alpha-glucosidase inhibitors, insulin and insulin analogues, GLP-1 and GLP-1 analogues and DPP-4 inhibitors.

In one embodiment the patient receives standard of care medication indicated for patients with chronic heart failure. In one aspect of this embodiment empagliflozin is administered to the patient in combination with one or more active substances that are indicated in the treatment of chronic heart failure. For example empagliflozin is adminstered in combination with one or more active substances selected from the group consisting of angiotensin receptor blockers (ARB), angiotensin-converting enzyme (ACE) inhibitors, beta-blockers, aldosterone antagonists, diuretics, angiotensin receptor-neprilysin inhibitor (ARNi), mineralcorticoid receptor antagonists and ivabradine. According to this aspect of the embodiment the patient is for example a non-diabetic patient or a patient with pre-diabetes.

Examples of angiotensin II receptor blockers (ARBs) are telmisartan, candesartan, valsartan, losartan, irbesartan, olmesartan, azilsartan and eprosartan; the dosage(s) of some of these medications are for example shown below:

Candesartan (Atacand), 4 mg, 8 mg, 16 mg, or 32 mg of candesartan cilexetil

Eprosartan (Teveten), 400 mg or 600 mg

Irbesartan (Avapro), 75 mg, 150 mg, or 300 mg of irbesartan.

Losartan (Cozaar), 25 mg, 50 mg or 100 mg of losartan potassium

Telmisartan (Micardis), 40 mg or 80 mg

Telmisartan (Micardis HCT), 40 mg/12.5 mg, 80 mg/12.5 mg, and 80 mg/25 mg each of telmisartan and hydrochlorothiazide Telmisartan/amlodipine (Twynsta), 40 mg/5 mg, 40 mg/10 mg, 80 mg/5 mg and 80 mg/10 mg each of telmisartan and amlodipine Valsartan (Diovan), 40 mg, 80 mg, 160 mg or 320 mg of valsartan Examples of Angiotensin-Converting Enzyme (ACE) inhibitors are benazepril, captopril, ramipril, lisinopril, Moexipril, cilazapril, quinapril, captopril, enalapril, benazepril, perindopril, fosinopril and trandolapril; the dosage(s) of some of these medications are for example shown below:

Benazepril (Lotensin), 5 mg, 10 mg, 20 mg, and 40 mg for oral administration

Captopril (Capoten), 12.5 mg, 25 mg, 50 mg, and 100 mg as scored tablets for oral administration Enalapril (Vasotec), 2.5 mg, 5 mg, 10 mg, and 20 mg tablets for oral administration Fosinopril (Monopril), for oral administration as 10 mg, 20 mg, and 40 mg tablets Lisinopril (Prinivil, Zestril), 5 mg, 10 mg, and 20 mg tablets for oral administration Moexipril (Univasc), 7.5 mg and 15 mg for oral administration Perindopril (Aceon), 2 mg, 4 mg and 8 mg strengths for oral administration Quinapril (Accupril), 5 mg, 10 mg, 20 mg, or 40 mg of quinapril for oral administration Ramipril (Altace), 1.25 mg, 2.5 mg, 5, mg, 10 mg Trandolapril (Mavik), 1 mg, 2 mg, or 4 mg of trandolapril for oral administration Examples of beta-blockers are acebutolol, atenolol, betaxolol, bisoprolol, celiprolol, metoprolol, nebivolol, propranolol, timolol and carvedilol; the dosage(s) of some of these medications are for example shown below:

Acebutolol (Sectral), 200 or 400 mg of acebutolol as the hydrochloride salt

Atenolol (Tenormin), 25, 50 and 100 mg tablets for oral administration

Betaxolol (Kerlone), 10-mg and 20-mg tablets for oral administration

Bisoprolol/hydrochlorothiazide (Ziac), 2.5/6 mg, 5/6.25 mg, 10/6.25 mg

Bisoprolol (Zebeta), 5 and 10 mg tablets for oral administration

Metoprolol (Lopressor, Toprol XL), 50- and 100-mg tablets for oral administration and in 5-mL ampuls for intravenous administration Propranolol (Inderal), 10 mg, 20 mg, 40 mg, 60 mg, and 80 mg tablets for oral administration Timolol (Blocadren), 5 mg, 10 mg or 20 mg timolol maleate for oral administration.

Examples of aldosterone antagonists are spironolactone, eplerenone, canrenone and finerenone; the dosage(s) of some of these medications are for example shown below:

spironolactone (e.g. Aldactone), 25 or 50 mg once daily or every second day, eplerenone (e.g. Inspra), 25 or 50 mg once daily.

Examples of diuretics are bumetanide, hydrochlorothiazide, chlortalidon, chlorothiazide, hydrochlorothiazide, xipamide, indapamide, furosemide, piretanide, torasemide, spironolactone, eplerenone, amiloride and triamterene; for example these medications are thiazide diuretics, e.g. chlorthalidone, HCT, loop diuretics, e.g. furosemide, torasemide or potassium-sparing diuretics, e.g. eplerenone, or combination thereof; the dosage(s) of some of these medications are for example shown below:

Amiloride (Midamor), 5 mg of anhydrous amiloride HCl

Bumetanide (Bumex), available as scored tablets, 0.5 mg (light green), 1 mg (yellow) and 2 mg (peach) for oral administration Chlorothiazide (Diuril), Chlorthalidone (Hygroton)

Furosemide (Lasix)

Hydro-chlorothiazide (Esidrix, Hydrodiuril)

Indapamide (Lozol) and Spironolactone (Aldactone)

Eplerenone (Inspra)

An example of an angiotensin receptor-neprilysin inhibitor (ARNi) is a combination of valsartan and sacubitril (Entresto).

An example of inhibition of the cardiac pacemaker $I_f$ current is ivabradine (Procoralan, Corlanor).

Examples of calcium channel blockers are amlodipine, nifedipine, nitrendipine, nisoldipine, nicardipine, felodipine, lacidipine, lercanipidine, manidipine, isradipine, nilvadipine, verapamil, gallopamil and diltiazem.

Examples of medications that lower blood pressure include angiotensin II receptor blockers (ARBs), Angiotensin-Converting Enzyme (ACE) inhibitors, beta-blockers, diuretics and calcium channel blockers.

In another aspect of this embodiment the patient is a patient with type 2 diabetes mellitus and empagliflozin is administered to the patient in combination with one or more active substances that are indicated in the treatment of chronic heart failure and in combination with one or more antidiabetic substances. The antidiabetic substances include metformin, sulphonylureas, nateglinide, repaglinide, PPAR-gamma agonists, alpha-glucosidase inhibitors, insulin and insulin analogues, GLP-1 and GLP-1 analogues and DPP-4 inhibitors. Examples thereof are metformin and DPPIV inhibitors, such as sitagliptin, saxagliptin and linagliptin. The active substances that are indicated in the treatment of chronic heart failure include angiotensin receptor blockers (ARB), angiotensin-converting enzyme (ACE) inhibitors, beta-blockers, aldosterone antagonists and diuretics.

Therefore according to one aspect of the methods according to this invention empagliflozin is administered in combination with linagliptin to the patient. The patient according to this aspect is in particular a patient with type 2 diabetes mellitus. Preferred doses are for example 10 mg empagliflozin once daily and 5 mg linagliptin once daily.

Therefore according to another aspect of the methods according to this invention empagliflozin is administered in combination with metformin hydrochloride to the patient. The patient according to this aspect is in particular a patient with type 2 diabetes mellitus. Preferred doses are for example 10 mg empagliflozin once daily or 5 mg empagliflozin twice daily and 500 mg, 850 mg or 1000 mg metformin hydrochloride twice daily.

In one aspect of this embodiment, the number, dosage and/or regimen of said medications to treat chronic heart failure is reduced in said patient, while the administration of empagliflozin is continued. In another aspect of this embodiment, the number, dosage and/or regimen of said medications to treat type 2 diabetes mellitus is reduced in said patient, while the administration of empagliflozin is continued. In yet another aspect of this embodiment, the numbers, dosages and/or regimens of said medications to treat type 2 diabetes mellitus and of said medications to treat chronic heart failure are reduced in said patient, while the administration of empagliflozin is continued.

According to an example of this aspect empagliflozin is adminstered in combination with one or more active substances selected from the group consisting of angiotensin receptor blockers (ARB), angiotensin-converting enzyme (ACE) inhibitors, beta-blockers, aldosterone antagonists, diuretics, angiotensin receptor-neprilysin inhibitor (ARNi), mineralcorticoid receptor antagonists and ivabradine in combination with metformin or in combination with linagliptin or in combination of metformin and linagliptin.

Examples of active substances in the above described groups are known to the one skilled in the art, including their dose strengths, administration schemes and formulations.

In the context of this invention the term metformin comprises metformin hydrochloride in the form of an immediate release, extended or slow release formulation. Doses of metformin hydrochloride administered to the patient are particularly 500 mg to 2000 mg per day, for example 750 mg, 1000 mg, 1500 and 2000 mg per day.

Empagliflozin and metformin may be adminstered separately in two different dosage forms or combined in one dosage form. Combined dosage forms of empagliflozin and metformin as immediate release formulations are described in WO 2011/039337 and are known for example as SYNJARDI®. Combined dosage forms of empagliflozin and metformin wherein empagliflozin is part of an immediate release formulation and metformin is part of an extended release formulation are described in WO 2012/120040 and WO 2013/131967.

A preferred dose of linagliptin administered to the patient is 5 mg per day.

Empagliflozin and linagliptin may be administered separately in two different dosage forms or combined in one dosage form. Combined dosage forms of empagliflozin and linagliptin are described in WO 2010/092124 and are known for example as GLYXAMBI®.

Within this invention it is to be understood that the combinations, compositions or administrations in combination according to this invention may envisage the simultaneous, sequential or separate administration of the active components or ingredients.

In this context, "combination" or "combined" within the meaning of this invention may include, without being limited, fixed and non-fixed (e.g. free) forms (including kits) and uses, such as e.g. the simultaneous, sequential or separate use of the components or ingredients.

The combined administration of this invention may take place by administering the active components or ingredients together, such as e.g. by administering them simultaneously in one single or in two separate formulations or dosage forms. Alternatively, the administration may take place by administering the active components or ingredients sequentially, such as e.g. successively in two separate formulations or dosage forms.

For the combination therapy of this invention the active components or ingredients may be administered separately (which implies that they are formulated separately) or formulated altogether (which implies that they are formulated in the same preparation or in the same dosage form). Hence, the administration of one element of the combination of the present invention may be prior to, concurrent to, or subsequent to the administration of the other element of the combination.

Unless otherwise noted, combination therapy may refer to first line, second line or third line therapy, or initial or add-on combination therapy or replacement therapy.

The methods according to this invention are particularly suitable in the long term treatment or prophylaxis of the diseases and/or conditions as described hereinbefore and hereinafter. The term "long term" as used hereinbefore and hereinafter indicates a treatment of or administration in a patient within a period of time longer than 12 weeks, preferably longer than 25 weeks, even more preferably longer than 1 year.

The pharmaceutical composition comprising empagliflozin according to the invention may be formulated for oral or parenteral (including intramuscular, sub-cutaneous and intravenous) administration in liquid or solid form or in a form suitable for administration by inhalation or insufflation. Oral administration is preferred. The pharmaceutical composition may be formulated in the form of tablets, granules, fine granules, powders, capsules, caplets, soft capsules, pills, oral solutions, syrups, dry syrups, chewable tablets, troches, effervescent tablets, drops, suspension, fast dissolving tablets, oral fast-dispersing tablets, etc. The pharmaceutical composition and the dosage forms preferably comprise one or more pharmaceutical acceptable carriers which must be "acceptable" in the sense of being compatible with the other ingredients of the formulation and not deleterious to the recipient thereof. Examples of pharmaceutically acceptable carriers are known to the one skilled in the art.

The pharmaceutical compositions and methods according to this invention show advantageous effects in the treatment and prevention of those diseases and conditions as described hereinbefore. Advantageous effects may be seen for example with respect to efficacy, dosage strength, dosage frequency, pharmacodynamic properties, pharmacokinetic properties, fewer adverse effects, convenience, compliance, etc.

Methods for the manufacture of empagliflozin are known to the one skilled in the art. Advantageously, the compounds according to this invention can be prepared using synthetic methods as described in the literature, including patent applications as cited hereinbefore. Preferred methods of manufacture are described in the WO 2006/120208 and WO 2007/031548. With regard to empagliflozin an advantageous crystalline form is described in the international patent application WO 2006/117359 which hereby is incorporated herein in its entirety.

Further embodiments, features and advantages of the present invention may become apparent from the following examples. The following examples serve to illustrate, by way of example, the principles of the invention without restricting it.

EXAMPLES

Example 1A: Treatment of Patients with Chronic Kidney Disease

Empagliflozin is administered to patients in a randomised, double-blind, placebo controlled, parallel group study to compare treatment with empagliflozin 10 mg once daily with placebo as add-on therapy to standard of care in patients with chronic kidney disease. The duration of the patients is preferably a long term treatment, for example between 30 and 48 months.

Patients include individuals with presence of chronic kidney disease with high risk of cardio-renal events defined by at least one of the following:
A) Very high levels of albuminuria (i.e. macroalbuminuria) defined as UACR 200 mg/g creatinine and/or
B) Impaired renal function with estimated GFR <45 ml/min/1.73 m$^2$.

Furthermore patients include those with stable single RAS blockade background therapy (i.e. either ACE-inhibitor or ARB with unchanged daily dose.

The composite primary endpoint of the study is time to the first occurrence of any of the following components:
CV death
 sustained decrease of 40% or more in eGFR (CKD-EPI)cr
 incidence of ESRD defined by either
  continuous renal replacement therapy (dialysis or renal transplantation) or
  sustained eGFR <15 ml/min/1.73 m$^2$ for patients with baseline eGFR ≥30 ml/min/1.73 m$^2$ or eGFR <10 ml/min/1.73 m$^2$ for patients with baseline eGFR <30 ml/min/1.73 m$^2$ A secondary endpoint is defined as time to the first occurrence of any of the following components: Occurrence of
All-cause mortality or all-cause hospitalization
All-cause hospitalization
All-cause mortality
eGFR (CKD-EPI)cr slope of change from baseline Other secondary endpoints are any one of the following components:
Time to CV death confirmed by adjudication
Time to first occurrence of sustained decrease of 40% or more in eGFR confirmed by adjudication
Time to first incidence of ESRD confirmed by adjudication
Time to first hospitalization for congestive heart failure confirmed by adjudication
Time to first all-cause hospitalization
Time to all-cause mortality
Time to first 3-MACE (i.e. CV death, non-fatal MI, non-fatal stroke) confirmed by adjudication
Time to first occurrence of all-cause mortality, sustained decrease of 40% or more in eGFR or incidence of ESRD confirmed by adjudication
Time to first occurrence of all-cause mortality, sustained decrease of 50% or more in eGFR or incidence of ESRD confirmed by adjudication
Time to first occurrence of all-cause mortality, sustained decrease of 57% or more in eGFR or incidence of ESRD confirmed by adjudication
Time to first occurrence of composite renal endpoint (sustained decrease of 40% or more in eGFR, incidence of ESRD) confirmed by adjudication
Time to first occurrence of composite renal endpoint 2 (sustained decrease of 50% or more in eGFR, incidence of ESRD) confirmed by adjudication
Time to first occurrence of composite renal endpoint 3 (sustained decrease of 57% or more in eGFR, incidence of ESRD) confirmed by adjudication
Time to first sustained decrease of 57% or more in eGFR confirmed by adjudication
Time to first sustained decrease of 50% or more in eGFR confirmed by adjudication
Time to first sustained decrease of 30% or more in eGFR confirmed by adjudication
Time to first incidence of acute renal failure (incl. AKI) confirmed by adjudication
Time to first incidence of AKI confirmed by adjudication
Time to onset of DM (defined as HbA1c ≥6.5% or as diagnosed by the Investigator) in patients without DM defined as no history of DM and HbA1c <6.5% at baseline Example 1B: Treatment of Patients with Chronic Kidney Disease Empagliflozin is administered to patients in a randomised, double-blind, placebo controlled, parallel group study to compare treatment with empagliflozin 10 mg once daily with placebo as add-on therapy to standard of care in patients with chronic kidney disease. The duration of the patients is preferably a long term treatment, for example between 30 and 48 months.

Patients include individuals with presence of chronic kidney disease with high risk of cardio-renal events defined by at least one of the following:
A) Impaired renal function with estimated GFR ≥20 and <45 ml/min/1.73 m$^2$ or
B) Estimated GFR ≥45 and <90 ml/min/1.73 m$^2$ and very high levels of albuminuria (i.e. macroalbuminuria) defined as UACR ≥200 mg/g creatinine Furthermore patients include those with a clinically appropriate dose of single agent RAS blockade background therapy (i.e. either ACE-inhibitor or ARB). Those participants for whom
RAS blockade is not considered indicated (e.g. due to concomitant medication or co-morbidity), or who cannot tolerate RAS blockade will still be eligible to enter the trial, but the reason for not using RAS blockade will be documented.

The composite primary endpoint of the study is time to the first occurrence of any of the following components:
CV death
Renal disease progression
  sustained decrease of 40% or more in eGFR (CKD-EPI)cr
  sustained eGFR <10 ml/min/1.73 m$^2$
  Incidence of ESRD defined by continuous renal replacement therapy (by either dialysis or renal transplantation) or
  renal death The key secondary endpoint is defined as time to the first occurrence of any of the following components: Occurrence of
Cardiovascular death or hospitalization for heart failure;
Hospitalization from any cause; and
All-cause mortality.

Other secondary outcomes which will include the individual components of the primary composite outcome:
Renal disease progression (as defined above);
Cardiovascular death.

Tertiary assessments will involve intention-to-treat analyses among all randomized participants of the effects of allocation to empagliflozin versus placebo during the scheduled treatment period on:
Renal disease progression, overall and with ESRD and a sustained ≥40% decline in eGFR considered separately;
Annual rate of change in eGFR, overall and separately from 2 months, in all participants and separately in various subdivisions (as specified below);
Mortality from particular categories of causes, including cardiovascular (e.g. coronary death, sudden cardiac death [not know to be coronary], heart failure, other cardiac, stroke, and other vascular) and non-cardiovascular (e.g. renal, infection, cancer, other medical, and non-medical) causes;
The primary outcome composite and separately, the annual rate of change in GFR, in various subdivisions based on assessments made at the Randomization visit:
(a) History of prior disease (presence vs. absence): diabetes mellitus*; cardio-vascular disease; heart failure; peripheral arterial disease;
(b) Participant characteristics: age, sex, region, blood pressure, body mass index;
(c) Laboratory values: HbA1c; eGFR; urinary albumin: creatinine ratio; haematocrit;
(d) Medication: RAS blockade; beta-blocker; diuretics;
Major cardiovascular events (defined as the composite of cardiovascular death, myocardial infarction, stroke or hospitalization for heart failure);
New-onset diabetes mellitus (defined as clinical diagnosis, commencement of glucose-lowering treatment, or central HbA1c ≥48 mmol/mol on at least one occasion) among participants without diabetes at baseline*, overall and separately among those with normoglycaemia or "pre-diabetes" (defined as HbA1c<39 [normoglycaemia] or ≥39 to <48 mmol/mol [pre-diabetes], respectively). *Diabetes at baseline is defined as patient-reported history of diabetes, use of glucose-lowering medication or baseline HbA1c ≥48 mmol/mol at Randomization visit.

Example 2: Pharmaceutical Composition and Dosage Form

The following example of solid pharmaceutical compositions and dosage forms for oral administration serves to illustrate the present invention more fully without restricting it to the contents of the example. Further examples of compositions and dosage forms for oral administration, are described in WO 2010/092126. The term "active substance" denotes empagliflozin according to this invention, especially its crystalline form as described in WO 2006/117359 and WO 2011/039107.

Tablets containing 2.5 mg, 5 mg, 10 mg or 25 mg of the active substance empagliflozin. Amounts of the ingredients are provided in mg per film-coated tablet.

| Active substance | 2.5 mg/ per tablet | 5 mg/ per tablet | 10 mg/ per tablet | 25 mg/ per tablet |
|---|---|---|---|---|
| Wet granulation | | | | |
| Empagliflozin | 2.5000 | 5.000 | 10.00 | 25.00 |
| Lactose Monohydrate | 40.6250 | 81.250 | 162.50 | 113.00 |
| Microcrystalline Cellulose | 12.5000 | 25.000 | 50.00 | 40.00 |
| Hydroxypropyl Cellulose | 1.8750 | 3.750 | 7.50 | 6.00 |
| Croscarmellose Sodium | 1.2500 | 2.500 | 5.00 | 4.00 |
| Purified Water | q.s. | q.s. | q.s. | q.s. |
| Dry Adds | | | | |
| Microcrystalline Cellulose | 3.1250 | 6.250 | 12.50 | 10.00 |
| Colloidal silicon dioxide | 0.3125 | 0.625 | 1.25 | 1.00 |
| Magnesium stearate | 0.3125 | 0.625 | 1.25 | 1.00 |
| Total core | 62.5000 | 125.000 | 250.00 | 200.00 |
| Film Coating | | | | |
| Film coating system | 2.5000 | 4.000 | 7.00 | 6.00 |
| Purified Water | q.s. | q.s. | q.s. | q.s. |
| Total | 65.000 | 129.000 | 257.00 | 206.00 |

Details regarding the manufacture of the tablets, the active pharmaceutical ingredient, the excipients and the film coating system are described in WO 2010/092126, in particular in the Examples 5 and 6, which hereby is incorporated herein in its entirety.

The invention claimed is:

1. A method for reducing the risk of cardiovascular death in a patient with chronic kidney disease, the method comprising administering a pharmaceutically effective amount of empagliflozin to the patient.

2. A method for treating, reducing the risk of or slowing the progression of chronic kidney disease and reducing the risk of cardiovascular death in a patient with chronic kidney disease, the method comprising administering a pharmaceutically effective amount of empagliflozin to the patient.

3. The method according to claim 1, wherein the cardiovascular death is due to fatal myocardial infarction or fatal stroke.

4. The method according to claim 1, wherein the cardiovascular death is due to sudden death or heart failure death.

5. The method of claim 1, wherein the patient has moderately to severely decreased renal function.

6. The method of claim 1, wherein the patient has elevated albuminuria levels ≥200 mg/g.

7. The method of claim 1, wherein the patient has an estimated glomerular filtration rate (eGFR)≥20 to <45 mL/min/1.73 m2.

8. The method of claim 1, wherein the patient has an estimated glomerular filtration rate (eGFR)≥20 mL/min/1.73 m2 and a urinary albumin-to-creatinine ratio (UACR) ≥200 mg/g.

9. The method of claim 1, wherein the patient has an eGFR≥45 and <90 ml/min/1.73m2 and a urinary albumin-to-creatinine ratio (UACR)≥200 mg/g.

10. The method of claim 1, wherein the patient is treated with a renin-angiotensin-aldosterone system (RAAS) inhibitor.

11. The method of claim 1, wherein the patient is treated with an Angiotensin-Converting Enzyme (ACE) inhibitor and/or an angiotensin II receptor blocker (ARB).

12. The method of claim 1, wherein the patient is a non-diabetic patient.

13. The method of claim 1, wherein the patient is a non-diabetic and non-prediabetic patient.

14. The method of claim 1, wherein the patient is a patient with pre-diabetes or a patient with type 2 or type 1 diabetes mellitus.

15. The method of claim 1, wherein empagliflozin is administered at a dose in a range from 1 mg to 25 mg.

16. The method of claim 1, wherein empagliflozin is administered at a dose of
10 mg or 25 mg.

17. The method of claim 1, wherein empagliflozin is administered once daily to the patient.

18. The method of claim 2, wherein the patient has moderately to severely decreased renal function.

19. The method of claim 2, wherein the patient has elevated albuminuria levels ≥200 mg/g.

20. The method of claim 2, wherein the patient has an estimated glomerular filtration rate (eGFR)≥20 to <45 mL/min/1.73 m2.

21. The method of claim 2, wherein the patient has an estimated glomerular filtration rate (eGFR)≥20 mL/min/1.73 m2 and a urinary albumin-to-creatinine ratio (UACR) ≥200 mg/g.

22. The method of claim 2, wherein the patient has an estimated glomerular filtration rate (eGFR)≥45 and <90 ml/min/1.73m2 and a urinary albumin-to-creatinine ratio (UACR)≥200 mg/g.

23. The method of claim 2, wherein the patient is treated with a renin-angiotensin-aldosterone system (RAAS) inhibitor.

24. The method of claim 2, wherein the patient is treated with an Angiotensin-Converting Enzyme (ACE) inhibitor and/or an angiotensin II receptor blocker (ARB).

25. The method of claim 2, wherein the patient is a non-diabetic patient.

26. The method of claim 2, wherein the patient is a non-diabetic and non-prediabetic patient.

27. The method of claim 2, wherein the patient is a patient with pre-diabetes or a patient with type 2 or type 1 diabetes mellitus.

28. The method of claim 2, wherein empagliflozin is administered at a dose in a range from 1 mg to 25 mg.

29. The method of claim 2, wherein empagliflozin is administered at a dose of 10 mg or 25 mg.

30. The method of claim 2, wherein empagliflozin is administered once daily to the patient.

* * * * *